US009074210B2

(12) United States Patent
Collard et al.

(10) Patent No.: US 9,074,210 B2
(45) Date of Patent: *Jul. 7, 2015

(54) TREATMENT OF BRAIN DERIVED NEUROTROPHIC FACTOR (BDNF) RELATED DISEASES BY INHIBITION OF NATURAL ANTISENSE TRANSCRIPT TO BDNF

(75) Inventors: Joseph Collard, Delray Beach, FL (US); Olga Khorkova Sherman, Tequesta, FL (US); Carlos Coito, West Palm Beach, FL (US)

(73) Assignee: CuRNA, Inc., Miami, FL (US)

( * ) Notice: Subject to any disclaimer, the term of this patent is extended or adjusted under 35 U.S.C. 154(b) by 124 days.

This patent is subject to a terminal disclaimer.

(21) Appl. No.: 13/201,254

(22) PCT Filed: Feb. 12, 2010

(86) PCT No.: PCT/US2010/024075
§ 371 (c)(1),
(2), (4) Date: Sep. 13, 2011

(87) PCT Pub. No.: WO2010/093904
PCT Pub. Date: Aug. 19, 2010

(65) Prior Publication Data
US 2011/0319475 A1   Dec. 29, 2011

Related U.S. Application Data

(60) Provisional application No. 61/152,132, filed on Feb. 12, 2009.

(51) Int. Cl.
| C12N 15/11 | (2006.01) |
| C12N 5/00 | (2006.01) |
| C12N 15/113 | (2010.01) |
| A61K 31/7088 | (2006.01) |
| A61K 45/06 | (2006.01) |
| A61K 48/00 | (2006.01) |

(52) U.S. Cl.
CPC ........ *C12N 15/1136* (2013.01); *A61K 31/7088* (2013.01); *A61K 45/06* (2013.01); *A61K 48/00* (2013.01); *C12N 2310/11* (2013.01); *C12N 2310/113* (2013.01); *C12N 2330/10* (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |

(Continued)

FOREIGN PATENT DOCUMENTS

| CA | 2686933 | 4/2008 |
| EP | 335451 A3 | 3/1988 |

(Continued)

OTHER PUBLICATIONS

Ploughman et al, Brain-Derived Neurotrophic Factor Contributes to Recovery of Skilled Reaching After Focal Ischemia in Rats, 2009, Stroke, 40:1490-95.*
Acheson et al, A BDNF autocrine loop in adult sensory neurons prevents cell death, Nature, 1995, 374: 450-453.*
Page from sequence listing for US-2005/0255487.*
Farnebo; Wrap53, a novel regulator of p53; 2009, Cell Cycle 8:15, 2343-2346.*
Jackson et al, Expression profiling reveals off-target gene regulation by RNAi, 2003, Nature Biotechnology, vol. 21, 6: 635-637.*
International Search Report corresponding to PCT/US2010/024075 dated Oct. 28, 2010.
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5853-5858, (2006).
GenBank Accession No. NM_000559, *Homo sapiens* Hemoglobin, Gamma A (HBG1), mRNA, (2008).

(Continued)

*Primary Examiner* — Tracy Vivlemore
*Assistant Examiner* — Kate Poliakova
(74) *Attorney, Agent, or Firm* — CuRNA, Inc.; Monte R. Browder

(57) ABSTRACT

The present invention relates to antisense oligonucleotides that modulate the expression of and/or function of Brain derived neurotrophic factor (BDNF), in particular, by targeting natural antisense polynucleotides of Brain derived neurotrophic factor (BDNF). The invention also relates to the identification of these antisense oligonucleotides and their use in treating diseases and disorders associated with the expression of BDNF.

13 Claims, 16 Drawing Sheets

(56) References Cited

U.S. PATENT DOCUMENTS

| | | |
|---|---|---|
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |
| 6,100,090 A | 8/2000 | Monia et al. |
| 6,140,492 A | 10/2000 | Morelli et al. |
| 6,147,200 A | 11/2000 | Manoharan et al. |
| 6,165,712 A | 12/2000 | Foulkes et al. |
| 6,165,990 A | 12/2000 | Singh et al. |
| 6,169,176 B1 * | 1/2001 | Bruice et al. ................ 536/25.3 |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramassamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Hong et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tauguay |
| 7,235,653 B2 | 6/2007 | Bennett et al. |
| 7,238,858 B2 | 7/2007 | Marraccini et al. |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Seth et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bamcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Seth et al. |
| 7,745,609 B2 | 6/2010 | Bennett et al. |
| 7,749,978 B2 | 7/2010 | Sah et al. |
| 2003/0139359 A1 | 7/2003 | Dobie |
| 2003/0186920 A1 | 10/2003 | Sirois |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0137423 A1 | 7/2004 | Hayden et al. |
| 2004/0138155 A1 | 7/2004 | Baird et al. |
| 2004/0175803 A1 | 9/2004 | Meritet et al. |
| 2004/0180336 A1 | 9/2004 | Gilad et al. |
| 2004/0254137 A1 | 12/2004 | Ackermann et al. |
| 2005/0009771 A1 | 1/2005 | Levanon et al. |
| 2005/0026160 A1 | 2/2005 | Allerson et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0215504 A1 | 9/2005 | Bennett et al. |
| 2005/0222029 A1 | 10/2005 | Bartel et al. |
| 2005/0255487 A1 * | 11/2005 | Khvorova et al. ................ 435/6 |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0197459 A1 | 8/2007 | Milner |
| 2007/0213274 A1 | 9/2007 | Salonen |
| 2007/0213292 A1 | 9/2007 | Stoffel et al. |
| 2007/0231816 A1 | 10/2007 | Chaussabel et al. |
| 2007/0248590 A1 | 10/2007 | Milne et al. |
| 2008/0146788 A1 | 6/2008 | Bhat et al. |
| 2008/0221051 A1 | 9/2008 | Becker et al. |

(56) References Cited

U.S. PATENT DOCUMENTS

| | | | |
|---|---|---|---|
| 2008/0293142 | A1 | 11/2008 | Liu et al. |
| 2009/0191263 | A1 | 7/2009 | Reich et al. |
| 2009/0192106 | A1 | 7/2009 | Dobie et al. |
| 2009/0208479 | A1 | 8/2009 | Jaye et al. |
| 2009/0258925 | A1 | 10/2009 | Wahlestedt |
| 2009/0318536 | A1 | 12/2009 | Freier et al. |
| 2009/0326041 | A1 | 12/2009 | Bhanot et al. |
| 2010/0105760 | A1 | 4/2010 | Collard et al. |

FOREIGN PATENT DOCUMENTS

| | | |
|---|---|---|
| EP | 335451 A2 | 10/1989 |
| WO | WO-84/03564 | 9/1984 |
| WO | WO-91/19735 | 12/1991 |
| WO | WO-92/00091 | 1/1992 |
| WO | WO-92/08796 | 5/1992 |
| WO | WO-93/20242 | 10/1993 |
| WO | WO-94-26887 A1 | 11/1994 |
| WO | WO-94/28143 | 12/1994 |
| WO | WO-95-15373 A2 | 6/1995 |
| WO | WO-95/22618 | 8/1995 |
| WO | WO-95/25116 | 10/1995 |
| WO | WO-95/35505 | 12/1995 |
| WO | WO-96-27663 A2 | 9/1996 |
| WO | WO-97-39120 A1 | 10/1997 |
| WO | WO-99-14226 A1 | 3/1999 |
| WO | WO-99-39352 A1 | 8/1999 |
| WO | WO-00-57837 A1 | 10/2000 |
| WO | WO-00-61770 A2 | 10/2000 |
| WO | WO-01-00669 A2 | 1/2001 |
| WO | WO-01-21631 A2 | 3/2001 |
| WO | WO-01-25488 A2 | 4/2001 |
| WO | WO 0122972 A2 * | 4/2001 |
| WO | WO-01-51630 A1 | 7/2001 |
| WO | WO-02-062840 A1 | 8/2002 |
| WO | WO-02-068688 A1 | 9/2002 |
| WO | WO 02085309 A2 * | 10/2002 |
| WO | WO-2004-016255 A1 | 2/2004 |
| WO | WO 2004-024079 A2 | 3/2004 |
| WO | WO-2004-030750 A1 | 4/2004 |
| WO | WO-2004-041838 A1 | 5/2004 |
| WO | WO-2004-104161 A2 | 12/2004 |
| WO | WO-2005-045034 A2 | 5/2005 |
| WO | WO-2005-070136 A2 | 8/2005 |
| WO | WO-2005-079862 A1 | 9/2005 |
| WO | WO-2007-028065 A2 | 3/2007 |
| WO | WO-2007-071182 A1 | 6/2007 |
| WO | WO-2007-087113 A2 | 8/2007 |
| WO | WO-2007-138023 A1 | 12/2007 |
| WO | WO-2008-057556 A2 | 5/2008 |
| WO | WO-2008-066672 A2 | 6/2008 |
| WO | WO-2008-087561 A2 | 7/2008 |
| WO | WO-2010-002984 A1 | 1/2010 |
| WO | WO-2010-040571 A2 | 4/2010 |
| WO | WO-2010-054364 A1 | 5/2010 |
| WO | WO-2010-058227 A2 | 5/2010 |

OTHER PUBLICATIONS

Haussecker, D., et al., "Dicer-Dependent Turnover of Intergenic from the Human β-Globin Gene Cluster," Molecular and Cellular Biology, vol. 25, No. 21, pp. 9724-9733. (2005).

Modarresi, F., et al., "Inhibition of Natural Antisense Transcripts in Vivo Results in Gene-Specific Transcriptional Upregulation," Nature Biotechnology, vol. 30, No. 5, pp. 453-461, (2012).

Shen, T., et al., "Modification of Globin Gene Expression by RNA Targeting Strategies," Experimental Hematology, vol. 35, No. 8, pp. 1209-1218, (2007).

Ausubel. Current Protocols in Molecular Biology vol. 1, 1994, 6.0. 1-6.4.10.

Barak, et al., "A β-Arrestin/Green Fluorescent Protein Biosensor for Detecting G Protein-Coupled Receptor Activation," J. Biol. Chem. 272:27497-27500 (1997).

Barber, et al., "Delivery of membrane-impermeant fluorescent probes into living neural cell populations by lipotransfer," Neuroscience Letters 207:17-20 (1996).

Baum, "Solid-phase synthesis of benzodiazepines," C&EN News, Jan. 18, p. 33-34 (1993).

Bernstein, E., et al., "Role for a bidentate ribonuclease in the initiation step of RNA interference," Nature 409;363-366 (2001).

Boutla, A., et al., "Short 5'-phosphorylated double-stranded RNAs induce RNA interference in Drosophila," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biology vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480;2-16 (2000).

Chabala, J.C., "Solid-phase combinatorial chemistry and novel tagging methods for identifying leads," Curr Opin Biotechnol. 6:632-639 (1995).

Cech, J., "Ribozymes and Their Medical Implications," American. Med Assoc. 260:3030-3035 (1988).

Chen, et al., "Expression of ssDNA in Mammalian Cells," BioTechniques 34:167-171 (2003).

Chen, et al., "Analogous Organic Synthesis of Small-Compound Libraries: Validation of Combinatorial Chemistry in Small-Molecule Synthesis," J. Amer. Chem. Soc. 116:2661-2662 (1994).

Cheng, J. et al., "Transcriptional maps of 10 human chromosomes at 5-nucleotide resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120;5458-5463 (1998).

Cubitt, et al., "Understanding, improving and using green fluorescent proteins," Trends in Biochemical Science 20:448-455 (1995).

Curiel, D. T. et al., "Adenovirus enhancement of transferrin-polylysine-mediated gene delivery," PNAS 88:8850-8854 (1991).

Dai et al., "SIRT1 Interacts With p73 and Suppresses p73-Dependent Transcriptional Activity," J Cell Physiol 210(1):161-165 (2007).

Davidson.; et al., "A model system for in vivo gene transfer into the central nervous system using an adenoviral vector," Nat. Genet 3:219-223 (1993).

Davis. et al., "Direct Gene Transfer into Skeletal Muscle In Vivo: Factors Affecting Efficiency of Transfer and Stability of Expression," Hum Gene Ther 4:151-159 (1993).

De Mesmaeker, et al., "Antisense Oligoinucleotides," Acc. Chem. Res. 28:366-374 (1995).

Deng et al., "Small Interfering RNA Targeting the PINK 1 Induces Apoptosis in Dopaminergic Cells SH-SY5Y", Biochemical and Biophysical Research Communications, vol. 337, No. 4, pp. 1133-1138 (2005).

(56) References Cited

OTHER PUBLICATIONS

Dixon, et al., "Anthrax," New England J. Med. 341:815-826 (1999).
Dolle, "Discovery of Enzyme inhibitors through combinatorial chemistry," Mol Divers. 2:223-236 (1997).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-3904 (1999).
Hagihara, et al., "Vinylogous Polypeptides: An Alternate Peptide Backbone," J. Amer. Chem. Soc. 114:6568-6571 (1992).
Heller, et al., "Discovery and analysis of inflammatory disease-related genes using cDNA microarrays," PNAS U.S.A, 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad, Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of athisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, 1980 pp. 75-77.
Larson, et al., "Rapid DNA Fingerprinting of Pathogens by Flow Cytometry," Cytometry, 2000, 41:203-208 (2000).
Larsson, et al., "High-throughput protein expression of cDNA products as a tool in functional genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, properties, and activity as inhibitors of replication of human immunodeficiency virus in cell culture," PNAS 86:6553-6356 (1989).
Li et al., "Control of APP processing and Aβ generation level by BACE1 enzymatic activity and transcription," Faseb J 20: 285-292 (2006).
Li, et al., J. Neurochem 89 1308-1312 (2004a).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target: identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).

(56) References Cited

OTHER PUBLICATIONS

Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-171 (1989).
Morelli et al., "The antisense *bcl-2-IgH* transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 80:2981-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleolides directed against Ha-ras point mutation induce selective cleavage of the mRNA and inhibit T24 cells proliferation," EMBO J. 10:1111-1118 (1991).
Sanghvi, Y.S., in Crooke, S.T. And LeBleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgcnic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of β-amyloid. 1-42 mediate different effects on oxidative stress, neurodegeneration, and BACE-1 expression," Free Radic Biol Med 41:202-212 (2006).
Trakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measuremems in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, KY, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman. E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270;484-487 (1995).
Wahlestedt, "Natural antisense and noncoding RNA transcripts as potential drug targets," Drug Discovery Today 11 (11/12):503-508 (2006).
Wahlestedt, C., "Antisense oligonueleotide strategies in neuropharmacology," Trends Pharmacol Sci 15:2:42-46 (1994).
Walsh, et al., "The role of cell-derived oligomers of Aβ in Alzheimer's disease and avenues for therapeutic intervention," Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada et al., "Endothelial Nitric-Oxide Synthase Amisense (NOS3AS) Gene Encodes an Autophagy-Related Protein (APG9-like2) Highly Expressed in Trophoblast" J.Biol.Chem.280:18283-18290 (2005).

(56) References Cited

OTHER PUBLICATIONS

Yang, et al., "Cellular and Humoral Immune Responses to Viral Antigens Create Barriers to Lung-Directed Gene Therapy with Recombinant Adenoviruses," J. Virol 69:2004-2015 (1995).
EP Application No. 06850393.7 Examination Report dated Oct. 18, 2011.
International Search Report and Written Opinion for PCT Application No. PCT/US2010/033078 mailed Jun. 29, 2011.
PCT/US2010/026119 Search Report and Written Opinion mailed Feb. 7, 2011.
PCT/US2010/024079 Search Report and Written Opinion mailed Jan. 31, 2011.
PCT/US2010/027394 Search Report and Written Opinion mailed Nov. 5, 2010.
PCT/US96/10287 (WO97/000271) The Regents of the University of California Jan. 3, 1997.

* cited by examiner

FIG.2

(SEQ ID NO.1)

>gi | 219842286 | ref | NM_170735| Homo sapiens brain-derived neurotrophic factor (BDNF), transcript variant 1, mRNA.

```
CACACACACACACACACAGAGAGAACATCTCTAGTAAAAAGAAAAGTTGAGCTTTCTTAGCTAGATGTGTGTATTAGC
CAGAAAAAGCCAAGGAGTGAAGGGTTTTAGAGAACTGGAGGAGATAAAGTGGAGTCTGCATATGGGAGGCATTTGAAAT
GGACTTAAATGTCTTTTTAATGCTGACTTTTTCAGTTTTCTTCCTTACCAGACACATTGTTTTCATGACATTAGCCCCAGGCA
TAGACACATCATTAAAATGAACATGTCAAAAAATGATTTCTGTTTAGAAATAAGCAAAACATTTTCAGTTGTGACCACCC
AGGTGTAGAATAAAGAACAGTGGAATTGGGAGCCCTGAGTTCTAACATAAACTTTCTTCATGACATAAGGCAAGTCTTCT
ATGGCCTTTGGTTTCCTTACCTGTAAAACAGGATGGCTCAATGAAATTATCTTCTTCTTTGCTATAATAGAGTATCTCTGT
GGGAAGAGGAAAAAAAAAGTCAATTTAAAGGCTCCTTATAGTTCCCCAACTGCTGTTTATTGTGCTATTCATGCCTAGAC
ATCACATAGCTAGAAAGGCCCATCAGACCCCTCAGGCCACTGCTGTTCCTGTCACACATTCCTGCAAAGGACCATGTTGCT
AACTTGAAAAAAATTACTATTAATTACACTTGCAGTTGTTGCTTAGTAACATTTATGATTTTGTGTTTCTCGTGACAGCATG
AGCAGAGATCATTAAAAATTAAACTTACAAAAGCTGCTAAAGTGGGAAGAAGGAGAACTTGAAGCCACAATTTTTGCACTT
GCTTAGAAGCCATCTAATCTCAGGTTATATGCTAGATCTTGGGGGCAAACACTGCATGTCTCTGGTTTATATTAAACCACA
TACAGCACACTACTGACACTGATTTGTGTCTGGTGCAGCTGGAGTTTATCACCAAGACATAAAAAAACCTTGACCCTGCA
GAATGGCCTGGAATTACAATCAGATGGGCCACATGGCATCCCGGTGAAAGAAAGCCCTAACCAGTTTTCTGTCTTGTTTCT
GCTTTCTCCCTACAGTTCCACCAGGTGAGAAGAGTGATGACCATCCTTTTCCTTACTATGGTTATTTCATACTTTGGTTGCA
TGAAGGCTGCCCCCATGAAAGAAGCAAACATCCGAGGACAAGGTGGCTTGGCCTACCCAGGTGTGCGGACCCATGGGAC
TCTGGAGAGCGTGAATGGGCCCAAGGCAGGTTCAAGAGGCTTGACATCATTGGCTGACACTTTCGAACACGTGATAGAAG
AGCTGTTGGATGAGGACCAGAAAGTTCGGCCCAATGAAGAAACAATAAGGACGCAGACTTGTACACGTCCAGGGTGAT
GCTCAGTAGTCAAGTGCCTTTGGAGCCTCCTCTTCTCTTTCTGCTGGAGGAATACAAAAATTACCTAGATGCTGCAAACAT
GTCCATGAGGGTCCGGCGCCACTCTGACCCTGCCCGCCCAGGGGACGCTGAGCGTGTGTGACAGTATTAGTGAGTGGGTAA
CGGCGGCAGACAAAAAGACTGCAGTGGACATGTCGGGGACGGTCACAGTCCTTGAAAAGGTCCCTGTATCAAAAGG
CCAACTGAAGCAATACTTCTACGAGACCAAGTGCAATCCCATGGGTTACACAAAAGAAGGCTGCAGGGGCATAGACAAA
AGGCATTGGAACTCCCAGTGCCGAACTACCCAGTCGTACGTGCGGGCCCTTACCATGGATAGCAAAAGAGAATTGGCTG
GCGATTCATAAGGATAGACACTTCTGTGTATGTACATTGACCATTAAAAGGGGAAGATAGTGGATTTATGTTGTATAGAT
TAGATTATATTGAGACAAAAATTATCTATTTGTATATATACATAACAGGGTAAATTATTCAGTTAAGAAAAAAATAATTTT
ATGAACTGCATGTATAAATGAAGTTTATACAGTACAGTGGTTCTACAATCTATTTATTGGACATGTCCATGACCAGAAGGG
AAAACAGTCATTTGCGCACAACTTAAAAAGTCTGCATTACATTCCTTGATAATGTTGTGGTTTGTTGCCGTTGCCAAGAACT
GAAAACATAAAAGTTAAAAAAAAATAATAAATTGCATGCTGCTTTAATTGTGAATTGATAATAAACGTCCTCTTTCAGA
AAACAGAAAAAAACACACACACACACAACAAAAATTTGAACCAAAACATTCCGTTTACATTTTAGACAGTAAGTATCTTC
GTTCTTGTTAGTACTATATCTGTTTTACTGCTTTTAACTTCTGATAGCGTTGGAATTAAAACAATGTCAAGGTGCTGTTGTC
ATTGCTTTACTGGCTTAGGGGATGGGGATGGGGGGTATATTTTGTTTGTTTTGTGTTTTTTTCGTTGTTTGTTTGTT
TTTTAGTTCCCACAGGGAGTAGAGATGGGGAAAGAATTCCTACAATATATATTCTGGCTGATAAAAGATACATTGTATGT
TGTGAAGATGTTTGCAATATCGATCAGATGACTAGAAAGTGAATAAAAATTAAGGCAACTGAACAAAAAAATGCTCACA
CTCCACATCCCGTGATGCACCTCCCAGGCCCCGCTCATTCTTGGGCCGTTGGTCAGAGTAAGCTGCTTTTGACGGAAGGAC
CTATGTTGCTCAGAACACATTCTTTCCCCCCCTCCCCCTCTGGTCTCCTCTTTGTTTTGTTTAAGGAAGAAAAATCAGTT
GCGCGTTCTGAAATATTTTACCACTGCTGTGAACAGGTGAACACATTGTCACATCATGACACTCGTATAAGCATGGAG
AACAGTGATTTTTTTTAGAACAGAAAACAACAAAAAAATAACCCCAAAATGAAGATTATTTTTATGAGGAGTGAACATT
TGGGTAAATCATGGCTAAGCTTAAAAAAAAACTCATGGTGAGGCTTAACAATGTCTTGTAAGCAAAAGGTAGAGCCCTGTA
TCAACCCAGAAACACCTAGATCAGAACAGGAATCCACATTGCCAGTGACATGAGACTGAACAGCCAAATGGAGGCTATG
TGGAGTTGGCATTGCATTTACCGGCAGTGCGGGAGGAATTTCTGAGTGGCCATCCCAAGGTCTAGGTGGAGGTGGGGCAT
GGTATTTGAGACATTCCAAAACGAAGGCCTCTGAAGGACCCTTCAGAGGTGGCTCTGGAATGACATGTGTCAAGCTGCTT
GGACCTCGTGCTTTAAGTGCCTACATTATCTAACTGTGCTCAAGAGGTTCTCGACTGGAGGACCACACTCAAGCCGACTTA
TGCCCACCATCCCACCTCTGGATAATTTTGCATAAAATTGGATTAGCCTGGAGCAGGTTGGGAGCCAAATGTGGCATTGT
GATCATGAGATTGATGCAATGAGATAGAAGATGTTGCTACCTGAACACTTATTGCTTTGAAACTAGACTTGAGGAAACC
AGGGTTTATCTTTGAGAACTTTTGGTAAGGGAAAAGGGAACAGGAAAAGAAACCCCAAACTCAGGCCGAATGATCAAG
GGGACCCATAGGAAATCTTGTCCAGAGACAAGACTTCGGGAAGGTGTCTGGACATTCAGAACACCAAGACTTGAAGGTG
```

FIG.2 (Continued)

CCTTGCTCAATGGAAGAGGCCAGGACAGAGCTGACAAAATTTTGCTCCCCAGTGAAGGCCACAGCAACCTTCTGCCCATC
CTGTCTGTTCATGGAGAGGGTCCCTGCCTCACCTCTGCCATTTGGGTTAGGAGAAGTCAAGTTGGGAGCCTGAAATAGTG
GTTCTTGGAAAAATGGATCCCCAGTGAAAACTAGAGCTCTAAGCCCATTCAGCCCATTTCACACCTGAAAATGTTAGTGA
TCACCACTGGACCAGCATCCTTAAGTATCAGAAAGCCCCAAGCAATTGCTGCATCTTAGTAGGGTGAGGGATAAGCAAA
AGAGGATGTTCACCATAACCCAGGAATGAAGATACCATCAGCAAAGAATTTCAATTTGTTCAGTCTTTCATTTAGAGCTA
GTCTTTCACAGTACCATCTGAATACCTCTTGAAAGAAGGAAGACTTTACGTAGTGTAGATTGTTTGTGTTGTTTGAAA
ATATTATCTTTGTAATTATTTTAATATGTAAGGAATGCTTGAATATCTGCTATATGTCAACTTTATGCAGCTTCCTTTG
AGGGACAAATTTAAAACAAACAACCCCCCATCACAAACTTAAAGGATTGCAAGGGCCAGATCTGTTAAGTGGTTCATAG
GAGACACATCCAGCAATTGTGTGGTCAGTGGCTCTTTTACCCAATAAGATACATCACAGTCACATGCTTGATGGTTTATGT
TGACCTAAGATTTATTTTGTTAAAATCTCTCTCTGTGTGTTCGTTCTTGTTCTGTTTTGTTTTGTTTTTAAAGTCTTGCTGT
GGTCTCTTTGTGGCAGAAGTGTTTCATGCATGGCAGCAGGCCTGTTGCTTTTTATGGCGATTCCCATTGAAAATGTAAGT
AAATGTCTGTGGCCTTGTTCTCTCTATGGTAAAGATATTATTCACCATGTAAAACAAAAACAATATTTATTGTATTTTAGT
ATATTTATATAATTATGTTATTGAAAAAATTGGCATTAAAACTTAACCGCATCAGAACCTATTGTAAATACAAGTTCTAT
TTAAGTGTACTAATTAACATATAATATATGTTTTAAATATAGAATTTTTAATGTTTTTAAATATATTTTCAAAGTACATAAA
A

(SEQ ID NO.11)

>hg18_knownGene_uc009yjg.1 range=chr11: 27633018-27679176 5' pad=0 3' pad=0 strand=
- repeatMasking =none GTAAACCAATAGCCCCCATGCTCTGTGCGATTTCATTGTGTGCTCGCGTTCGCAAGCTCCGTAGTGCAGGAAGGTGCGGG
AAGGTGTGTCTGTGGCCCGGGAAACGCACGCCCTCTCCCAGAGAACTTGGGTGCTGGGATGGGGAGGAAGGGGAGAGTT
GAAAGCTAGGGGAGCGAGACCTCGGGGCGTGCGATTCTCACTCGCTCCCTCCCGCCCCAGCGCCCACAGCCGGGGTTTCT
GCAGAGGGCGCGGGACGCGGGCGTTCCCCGGGGCTGAGGCTGGGGCTGGAACACCCCTCGAAGCCGCGGGCGTCCTGTCC
AAGGCGCCCCAGGGAGGGGCGCAGGACTCGCAGGGGCGATGTCGCTGGGGCGCCCTAGGGGAGGGAGGAGGTGAGGACAGGCCCCGGG
GGAGCGGGGAGTTCCGGGCGCCCCTCGGTTCCCCGCGCGAGGAAAAGACGCGGCGTTCCCTTTAAGCGGCCGCCTCGAAC
GGGTATCGGTAGCGCCGGCGAGCGGGGAGCGGGCGGCGGGGGCGGGGGGGGGGGGGCGCGCCGTTGACCAATCGA
AGCTCAACCGAAGAGCTAAATAATGTCTGACCCGGGCGCAAGGCGCAGCCTGGAGCTCCGGGTCCCCGACGCTGCCGCC
GCCGGCCCGGGCCACCCCGCCCTCGCTGTCCCGCCCGCACCCCTAGGCGCCTCGGGCTCCGGGCCGGACAGAGGAGCC
AGCCCGGTGCGCCCCTCCACCTCCCTGCTCGGGGGCTTTAATGAGACACCCACCGCTGCTGTGGGGGCGCGGGGGAGCAG
CACCGCGACGGGGACCCGGGGCTGGGCGCTGGAGCCAGAATCGGAACCACGATGTGACTCCGCCGCCGGGGACCCGTGAG
GTTTGTGTGGACCCGAGGTAGGCAAGCGCTGGGAATGGGGCTTGGTGCAGGAGCTGCCCGTCCGCGGGAGAGAGTTGA
CTGGGGGATCCCCCACCCCAAAGTTGTGGGACGAGGCCAGTCTCCTTCTTTCCTCCCCTCCGGTAGAAGGGACGATTTGGA
GTTACTCTTGGGGAGTTTTCTCCCCCATCCCACAACCCAGAAGGTCAGCCGGCCACCACCAGGGAAAAGGGACCCGGGGA
AGTCACGAAGTAGAGGAGGGAAGGCCTGGAGGAGACCCAGAGCTGCGTGATGGGAGCAAAGACGGGCGACCCGGGGATC
CCTCGCAGCCCTCCCCCAGCCCAGGAGTAGTCGAGAGAGACTTAGGGGCCAGAGCTGTCGAGGGTCCTGACTGAGGGG
AGGGTGCTGGGGCTAGGCTAGGAATCCTTCCAGGGGGTGGGTGGTCCCCGCGCCGACTTGCGGGGGGAGTGGGAGGGAA
GCTTGCGCCTTCAGCCCGCATCCCTTCCCCGGAGCTGCACACGGCTACCTGCTCCCCAGGAATTGAGACTGAAGTGGACTT
ACAAGTCCGAAGCCAATGTAGCTTGGAAAACTTGGGAGGCGGAATTCCTACCGCTGGGAACTGAAAGGGTCTGCGACAC
TCTCGGGCAGGCCGAACCCACATCTCTACCCATCCTGCCGCCCCTCTTCTGAAGCGCCCTCCAGGGAAGTTAAGAGTTTTGA
CTTCGGGGAGTGGTTGGGATGTACGTGGGGGATTCTTGACTCGGGTTAGTCTCTGGGGATCCAGAGCCGGGAAGAGGAA
TGGGTGAGTGAGTTACTCCTGGAAAGAAATAGCTGAGGATTGGGGGCTCTGTGCCTGACGGGCAAGAAGAAGGGGAGAT
TACAGACTAGGGGCATCCCTAAGGAAGAAGCCTCGGGGCTGCGAGGGTGAACTGGAGGATGCAGTGTTTGTGTGTTGGG
GGTAGAGCGGGGATGAGGGGACCGGGGTGGAGGGGAGGCGAGGAGGAGGAGGGGACCCAGAGAACGAAGCTAGGGAAG
GTAGAGGGTGCCCTCTGCCGGCCATGCTGCCAAGAGCAGCTACTGGGGCGGGAGGCTGGGGGTGGGAAGTGGTAAAG
GAAGGTTTGCGGGATCCCTTAGAGAGCTGGTAGGAGGGACTTGTTGAATGGTGCTGCTGACTCCAGCTCGGTGGGGCGT
GCGACTCGTCGTCGGTGGATTTGACTCCTCGTTCTTGTTGGCTTCTATGCAAGTTTCCTTCGCGCTGGGGAGCTTTGAT
AAGCCTCGATTGGCGGTGTGTTAGGGCTTCTTGGATCTTATTTTAGGGTCTCTAGTTATCCTGCACTTACTCCTTAATGTC
AGTAGCAACCAAAGAACATTTTCCGACAAGCACGCAGGAATGTTCTTGGCCAGAAGCAAAGAAAGGCATATTTCTGAGT
GTTTATTAATCCTCCTAGTAATCTTTTAAAGCAAAGTAATATGTAATTGGGAACGTTGATTTCTAACTGCATAAAAGG
CGACATGATATTAAATGAGACCCCTCCCTACTGACTCAATATCCTGCAAAATCTCTCTCTCCCCTTTATTATATGGAAAA
ATCTATTTTTATATGAGTTTGTTGTAAGGTCAAAAGCCATTTGGTCTTACAATTGATATGTCTTTACATTTAACTTATTG
AGGCATAATTACAGATTTAATTTGTATGAACGTGTGTGCCTTCAATGCTTATCTCATGCAACATAATTTTAGGTTGGAGA
TTTCTGATGTTATGGCATGTAGCCGTTTCAAGGCATTACACATAATAGGTAACATAGCATGTTGAAATTACACCACAAAGTT

FIG.2 (Continued)

```
TTGACCCTGGGAACAGCACCTTTTAAAAACAATCACTAAACTCCTGTTCCTGTTTTCTGATTTTGCAAATGCCTTGCTTAAG
ACTTTTTTTTTTTTTTTTTTTTTTTTTGGGAAATTTACCTCTGGGTTAGCAGGAGAGGTAAAAAAAAGGAAAGAGAC
ACTTGTTGAAATGTAACCATAACCTTTACTGGAATTTAAAACATGTTGGTCACCATTACTGGAATTCCAGGGCCATAAAGT
CGTTGTCTTTTTTTCTTCTACTTCATTTTGTAAAATGTGATAAATGTTGGTAAATATAGACCAGTAGTAAGTATTATGACA
CTAAAAGCATTATGTATGTGGAACTATTTTAAGTTATTACAGAACATTTCTATTTATAAATGATATAAGCAGAAAGAAAT
GATTTCCAGATAAACAAGGCTTACGTACATGTTTTGAAGCATTAGAACATTGCAGACACTCTTAGACATCACATTTTTTAA
AGCAAAATAACAGTAATTTTTCACATACCTTTGGAGCCTTTCATAGCCCATTCAGAGCTGAGTTAGTAGCTGGAAGTTTCC
TTTATTTTAAGGTGATATTTTAAAACCATTTAACATGTATAGTAGGTCAACATTGGTGCATCCAGAAAATGAAGCATTTAG
GAAATCTGTTTCAGTGTCTTTTCAATGTGTGTAACTTTTACTTGCAAACCAATGGAACCAAGAAAGTCATCATTTGCCTAA
AATGCAGTCATCACCTCAAATGATTCATTTATACTATGTGAGTTAATTGCCTTCATCTCATTAATGGCCAAGGAGGGAAGG
GAGGTCCTGGGGTATTTCTTGTTCATTTTGACTCACCAGGAGGGAAAATCCTGTAAAAAAAGAAATGCAAATTTCTAAAA
TCCTGGCTCAAAGTCCGTGGGTTTCCTGTTTAAAAGGGGCGCCATGAAAATGTAAGCTATTCCCTTTTTCCTGGAATCTTT
AAGAGTCCCAGCTTTCAATAGTCAAATGTAGATGATTGATATCATTTCTTATATGAATAGCACTGGTTGTAGTTCAGC
ACGCACAGTGAGCTGGGCACGCCCACCTGATAGTATAGCAGAGAACTTGTTACATTCTTTTTACATTCATCTTCTAAAAC
CTGGGGTGCTCTCTCTCTCTCTCTCTCTCTCTCTCTCTCTGTGTGTGTGTGTGTGTGCGTGCACGTGCCGTGTGTGTA
GAGGGGGAGAGAGAGAGAGAGAGAACTGTGAACTGTGAAATATAACACAGCCAGCAGCTTGGGTCTCAATCGTAGACT
TACTCTTAAGGAAATTTACAGAATGGAAAGGTCATGTTCAAGTAGTTTATTAACATTTGAGATGTAGGAAATTAATCCCG
GAGTACAGAAGAACAATTTCAGACTTCCTGAATAAAAACAGACAGCATAGAGAGTGGATGATAGCTAAACTCTGAATAT
CTTTTGAGAAGAAAGGCACTCCCATTTCAGGTGCCCATAATATGGATTGATTTTAGTGATTAAAACATTAATTTTCAACT
TGCATCTCCCTGTGTGGAAGAGTTCAATTTGTGTGAGGGGTCTCGCCTATCCAACAAAAGTGAATATGTCCCTTTTATAGG
GTAATTGCTAACTTGTCTCAACTTGTTTCAAACAATTGTTATAGAGCACTCAGTTTCCACTAATTGCAAAATTGTTGCTTA
ATTGAAGGACTCTCAGCCATCTAGTGCAGCCATTCAGCCACTGGCAGGCTCTGTGATCTCAAACTGTGAATTGCATTTAA
AGAGGAATCGAGGAGAGAATTCTGTGGAATTCTAGGTTTTAAGTGCTGGCTGTTGTTCAATGGAAGAGGAAATCATTTGA
ACAAGAATCGCATCAAGTTGTGTTGTGATAAATTTTCTTATTAGGATGAATAACATGCACAGATGAGCTTCAAAAGTGA
ATGAGCAAACTTACTGGTTACACTCTGCATCCATTTACTCTGTTTAGTATGGAGTAATGTTAGGCAATAAATGATGCTGGC
AAATGAAATCCGTATGTTATTTGCATGTGGTATTTAAACCTAGGAAACATAGAGTGGCTTTGGTATTTGTAGGCTTAGTCA
TGTGTGTCCTAAACGTCCTCTTAAACTTCTACTTAAGGCATAGAATTATTTAATCCTAAATAATTTTATACTTAAGTGCCTC
ACTGGATTTCCAGAATATTTACACTGTAAAGATTTAGAAAGGTCATGAACCCAATTATTGACTATATGGAATCATTATTGA
TGGCAGATGCAAAATGGAGCTCACTAATGTACTGACATTGAAAACCTTTTGCAGGGGAGAGGAGGGGGAGTGGTAAATG
TGTGTGTTCTTTAAGTGGAACAGGAAGGTATTCTCTTTTCTGTAGAAAAATTTGAGTATCTGGTCAGATAAGTGTGGAAGC
TTTCATTTAAATTAAGTATTTAAGTTCAAGTAGAAGCTCTAGGGCACTTATCCTCTTGATGAGACAAATCTTATCAAATAT
ACTAGATGCTAAGAAGTGGCTCATTGCCCTGATGTCTCATTTATAGATTGATGTTTGAGGATGGGTTGCATTAAGTGAGTT
AGGGGGGCTGAGTGTGGGACAGGAGAACGATTGGAAGGAAGCAAAGTAAATTTACAAGCTTTAGTGACAGCCATAATAAA
GTAAAAGTTTATTCCAGAGAGCCTAGAGAGTAAGGAACGGTTCATTATAGTTTTCCCCAAAGGTTCACTTGAAAGAACTTTC
ATTGGTTGTCATGGTAGTAATGTCCTGATTTTGAAATCTCCCAGAACCTAGTAGCTCTTAAACATGCTTTCATCTTGGTTCC
TTTGGTCTGACGGAAACTTTATGACGACCCTCTGTGTTTTTGACATGCCTCTGCATTTTGGAGAGAGGAGGTCAGGCAAG
GGAGGATTTCTTAAAACTAAGACAGTATAGTAAGGAAACATAAAATTATATGATAAAAATCACTGAACTTCAAATTGAC
TTACTGAAATAAAACCTAGAAGGCAACCTGTCGTTTAATTACAACTAGCTTGTATAAAATTAAAATTTATAAAATGGGAA
TTCAAAGAAAATAACGGGCAGTTCCAAGTAATTTAAGCAACTCACCAAAAATTGAAGTAATAGTGCCACCTAGAGAAC
AAAATCACCAGCTTTACTAGCCAAATGGCTTATTTCCATATGAACCATTTTTCCAACGCTACAGTTACTAGGATTCCTTGT
TACCATATTCAGATCTTGTGAGTGTGTATGGGGGTGGGGGTTGCATGTGGAATTACAGATGAAATTTTAAAACAAGCAGA
TCCACAATTTGATATATGCACTAAATCCTTTTAACGTTGTAATGTAGCCAAATGTAGAATAGCATGCCAGGAATCAACGGC
TAGCATCCTTTTTAACATTTATTATTTTCATGGATATGTACCAAACCGAACCATTGAGTATAAAGGTTCTGATTTTATTTAT
TTGCTACAGGCAATTCATTATACTTTCTGAGATACAATAACACCAAATAATTTGAGTAGAGAGACCTTTAAGAATGTTTTC
GATTTATGATCTACCTTTAACTTTAATGTACTCAGAAGATGTGAGAATAAAATAAAGTCAAATATAAGCAAGATTTTAAA
CACACACACAAAAAACAAACAAACAAGAAAAAGGAAGAAAATTATAAGGATTGCCTTAACCTTAGAATAGATGAAGGTA
TACATCTGAGCCAGCACCAAAAAAAAAAAAAAAAAAAAGTTATGGAACCAGGAACCAATAATTACAAATTGACTTAAAAT
TCTTGGATGACAAAAATCTATATTTAGTTCATTTTTGCATGCCCCACAACAGCATCCAAAACAGTTCTGGGGAGGCACTT
TGATAAATGTTGCTGAATGCACTAATAGATTGATTAATGGCTGCTTCAGATTATCACTAGTGATGTAGACAGAAACTTCAT
GAAAATGGTTTGTCTTGCTGGAAGAAAGGCAGAAATTGGAGGAAAAGGTTTAATAATATTTTCCCCAGTACCTATTATA
AAAGTCATTTAGTTGGCTTAGTTCTATAATTTCTTATGTGTAATTTGATTCACTTATGAAATGTGAATATATGAAATGTTA
AAGTTGATTTAGACAGCAACTATAAGCTTGTGGATTTTCTTTTAAATGTCTTCAAATTTTTAAATGCCAGTGGAGATGCCA
GCGACTGTGCTTCAGGGAGTAGAATATAGTATATCTTAAATTTGTGCCAATTTCTGGTAAGCAGAGAAAAAATTGCATGA
TAACCAAAGAAAGTCATATTGTTTGTGCTTTGTGTTATTCATGGAAGCAATCAGGTGCAGAAAACTTTCTTTTTCAGAAAA
AAAAAATTACTAAAATAAAGGTGCGTGTGTGTATGCACATATATCTAAAGGGAGAGAGGGAGAAGGAAACTTACTAA
ATAAAATTTTTGCCACATGGGATTTAGTCTAATCAGTCTTGGTTTGGAGTTGCTATCATCAGTAGTTCCATTTTGTGATTC
TTTCTTTCTGCCTTCATGTGCCTTTGAAAACTGAAACTATGCCCAAATTAAAACAAGTTTTTCTGTCTTTTCACATGTTCAC
TTATTTCTTGAATGTGTTTTTAAACACAGACAAACTTCTTTTACATCATGTAGAATCTGAAGGTCGAGAAATTTGCAGTCA
```

FIG.2 (Continued)

```
TTTTGCTGGAGAGAGATGCTTGGCGGAGTCCCAGGCCACATTCCTAGGCCAAACTCTCGAAGGTATTCCTCTTATGCAACA
TTGGGAAAATACATCCAGCACCGACATGTTGGCTGATAATGTGTCTGAAGGCACAGACGATATGCTTATCATATGAAACA
TAAAGCCAGCAGATATTGCAGACATTCTGTTGAATGATAGAATCTGGATCATTTACATTTACTTAAATGTAAAATACTATG
ATTAAGTACAAAAAAATCAATTTAGGAGAGAATAGAGAGTTGCGGGCACGGTTTTAGGGGATGACTTATCAGCAGATTGT
AGAAAGGAAGCTTGAATGTTTTAAATTAACTGCAAGTTCAGTATAAGCCAGTGGTGTGACAAGAGGCTGTTATCATAGCT
ACTGAAATTTTGGGCTGCACTGCTAGAAATATAATACTGAAATGGAGAAGCTAATAATTCTTCACTTTTTAAATAGACTGT
ATCTAGAATATTATCATCAGTTCAAGGAAATGAAATAAGTTGTTTTAGGTACATCATCGATAAATTAGTGTACATTCAAAT
CACTGTGACCAGGATGCATAGGGAATTTGAAAGCATTGCATGTGAGCAATGGTTGAGGGGACTTGGAATGCATGACTTAG
GGACAAGAAAACTTAGGCTGGAATGGCAAGTGGTTTTGAATGTGGGTTGAGAAGAATTCTAAAACTGTGAAGGATTAG
TAAAAATAACATTCAGATTGCTAATGCCTACTGTGGCTGGGAGATTAGAGTGTCAACATGTGTGATGTATTTTTGACATCC
TTATTTTGAGGATGGGCTTCAAAGATTTGACGAACTGTCATAAGTGTAATTTGTGTTGCTTCAGACAGCAGTTCTAGAACC
AATGATGTAAATTTAGATACTCTACATGGTAGTTAGAAAACTTTCCATTAATTTAATTTAGCAAATATTGAATGCTCACTG
CATACAGAGCACTTTATTAGAGGAATATATAATAAAGAAAAAAGAGGTCTGGTGTGGTGGCTCATGCCTGTAATCCCAGC
ACTCTGGGAGGCTGAGGTGGGAGGATCACTTGAGCCCAGGAGATCATTACGAGTCTGGACAACATAGCAAGACCCCATCT
TTACAAAAGACAAAAAAAATTATCCAAGCCTGGTGACAGGCACTTGTAGTCCCAGCTACTTGGGAGGCTGAGGCAGTAG
GATCGTTTGAGCCCAGGAGGTTGGGGCTGCAGTGAGCCGTGATTGTCCCACTGCTCTTCAGCCTGGGTGACAGAGTGAGA
CCCCGTTGGAGGGAAGGAAGGGAAGGAAGGAAGAAAGGTAGGAAGGCTGAAATGAAACCCTTTTAGAAATGACACTAA
AATGGGAGGTTGGAGTAAGGTATTTCTGAAGTGCCTTTGTACTTGTTTTTTCTAATGCATTGGCCATAAGTCTGCTCCTT
ATTTATAGTCCATAAACAATCCTAATGAGAACAGTTATATATTTCTGCCTTTGAATCATCTACTTGAAGTGTTTAGCATCAT
GAATTGAGTATCAGAAATCCCTCCCCATTTCTTTGCAAAGCGCTGTATTTTTACTTTTCCTTATTTGTATACAGATTCTCAAAA
TTGGCTATTTTTCCTTTGGGTTAGACAGAACAGAATGTCTGGAAAAAAAAGTTCTTATCAAATTCAGGTGCCCAAATTGCT
TAAGAAATTAACTTTTGAGGTTATATTTTTTTAGGGTTCAGTAGCTAAACTAAGAAAACTTCTCACCGTTCACCTTCACTTT
TGGAAACCACAAAATCTTCAGATATTACAGTTTTCCAAAGAGTTTCTCTTTTAAATATAAACTAAAAGGAATTGACTCCT
CCCCCAACTCCCTCAGGCCTCAGCATGGATAGAGTTACTTTTTTTCTTAATAATTTATTTATAACTTATTTTGCTCTTCTGT
AGAACAGCTGGAGATTAAGCAACATGGCCATGACATAAAATGCCAAGTTAGACCATAAGATGAGCAGCCCACTCCAAGTA
TGAATGAGTACTTATTCTTTGTGATCTCTCATACTGCTTTTAGGTATTAATAGTGTCAGTCAGCAAAGCAAACAGTTTAAT
ATTTACATCTCCTTTAGGATATCATATAGTTTATAGTTTGTATGTGTTCTTGCGTGTATGTTTCTTCTGTTTCAAATTCTTTT
TTCTTAAAGTAAGAATGTTATATGTAGCAAATGGTTCTTTCATTAATTCATTTGTTAATTCACCGTTGCATTAATTGAGTGCC
CAGTGAGTGTCAGGCACTGGGCTACTTGGATTTCTTTTCCCTGTATTGATCCATATATCTTCAGGTGCTCCTTGATATGGCT
CTCCATTGACTCTCTCATATAAGGCTTTCATTACCTATTCACATACTCCCTCCCAAAGAGGACTGGTCCAAAAGTAAAATC
TTGAGCAAGTTCTCTGAGTTATTTCAGAACTTCTTGCCCCCAAACTGTATTTTAATTATTGACTGGTAGCATTTTGGAATA
ACTTACCTCTCTTTTTAAAGATTGAAGTTCTTTATCCTCTCTGATTTTCAGGGTGTCAGTTTGTGTACAAATTGAGACAATA
AAAATGTTGTTAGACATTTTCTTAAAGCATTTGCTATGTGAGAATCTTTCATGAAGAACTCTTTTAACAATGACTCTAT
AGCAGAAGCCACAGTAGAGGGGAACTACTGAATCAAAGATGCGTGTTTGAGTCTATGATTTTATGATGGATTTTTTTTTT
TTTACATACAAGGATATGCATGGGTCTTTTAGTATTCAGGAATCTGTTCTTCACTTGACAGTATTTATAAATTGTGTGTTTC
CCCCTAAAAAAACTTAAATTGTGAGAATGCTTCCATTTACTAGAAGTTGGTTAATGATTATGCCAAATAAGGAAAATAAG
ACAGAAAAATCAGTTTAGTGAATACTATTTGCCTTTAAATTTAGTAATTTAGTAACAGTATCTCTTTGGGGTTTACTAGA
AACCACTTTTAATCCAATAGGTCTCTTTCATTGTGAAGTCAGGAGGGATTTTGCTTAAATGTGTAGTATAGGAATCTAT
ATGTGGTGTTCAAGGATCATGTAAATATGCTGATATAATCGGAGCACAGTTTGGCATCATTAACTCAGAAATATTTAAACT
CTTGCTATACAACATGGAAGCAAACTTGTGCATAGTTTGTGTGTGTGTGTGTGTGAATCTCAAAAAAAGAAAAAAATC
ACAGGATCAGGAAGTCGGAATAGGTCCCACTTTTCTTCTAGTACCAAACCTACAGCCATGTTCCTAGCCTTCTCTTTTACT
CCCAAGCAAGACAGACAGGCAAATGACCATCCTGCTGCCCATTCTGTGTATATTCACTTGCATTGAGAGTTGTATTCACC
TGCTTGTTGAGAGTATTCACAAGTGCTGATTCCTACGTGATTTCATGTCATGTAGACAAGATTGCACACTTCAATAATAATCTTGTCCA
TTTAGAAATAATCATGTATAAATGGTTGAATATTAATACAGGATTGCCTTATCAAGTATTTATTAATCATTAAAATGTGG
TGTCATTAATACAATTTATTTTAAGTGCTTTCCTAAAATACCAGATTATTTTCTGATTTTCACATCCCTGACAATGACTTT
CTTAAACTTGGTAGCCAGGAACAGAAAACCTAACACTGCATGTTCTCACTCATAAGTGGGAGCTGAACAGAGAGAACAC
ATGGACTCAGGGAGGGGAACCACACACTGGGGCCTGGAGCAGGGAAGGGGAAGGGGAGAGGGAGTGCGTCAGGACAA
ACAGACAAATAGCTAATGCATGCGAGCCTTAATACCTAGGTGATGGGTTGATAGGTGCAGCAAACCACCATGACACATAT
TTACCTATGTAACAAACCTGCACATTCTGCACATGTATCCCGGAACTTAAAGTAAAATAAAAAATAATAATAAAATAAAA
TAAACTTAGTAGCATCTATTGTTCCAGAGCCTGTAATTGCTCTTCAGGCAGTCTCACATAAAAACCTAGGAGAACCTTCAC
TGTCACTGTTCCATGAGGTGTTAGGAAAACTTGCTCTACTGCAGTGCCCCAGTAGGCCATTGGTACTGAGACCAAATTCAG
CTGGTTTGTTGTTAGTACGATTCCTACGTGATTTCACTTGCATGTAGACAAGATTGCACACTTCAATAATAATCTTGTCCA
AATGTGTGGTATTCCATACATTTTTAAAATGCATTCACATATCTCATTCCATTTGATCCTACAAATAACTCTATAAAAAAG
ATTGGCAGACATTATTTCTATATAACAGAGGAGGAAACTGGAGCTTAGAGAAGCTAAATAGCAATCCAAAATGCACAGCT
GTAGAACCAGAGCAAGGATGATAGCCCAGTGACTTCACCTAACCTAGTCCCCTTACCACCACTCCAGCTGTCTATAACCA
AAACCTGCAGTATTCAAGTAAGAAACCATATCTTGCCCTTGATGCATTAATGTGAGACCTGGAGCAGGAACAGGCTGATA
TTGTCACCCTGGCCTACTGTCCACCTTTGTCTCCAGCAGAGACTGGTACCCTTCTGTGTGCCAAGGAATAAAGTGGTAATG
GGAAGATTAAAAATGTTTTTCCAAGGAGTTTTTAATTTAATTTTTTAAAAAAGAAAAAACTCTTAGAGGGAAAAATGA
ATATATGACTTTTGATGTATTGTTCCTTAGTAACTTAGTTATAATTTTACTTAAACCTGAGACTCTTGCTAAGTGAATGATT
```

FIG.2 (Continued)

```
AGAAATATTAGGTGGCTGGCCAGATGGCAAATAGGAACAGCTGCAGTCTGCAGCTCCCAGAGAGATCAATGCAGAAGGT
GGGTGATTTCTGCATTTCCAACTGAGGTACCGGGCTCATCTCATGGGACTGGTTAGACAGTGGGTGCAGCCCATGGAGG
GTGAGCCAAAGCAGGGTGGAGCATTGCCTCACTCAGGAAGCGCAAGGGGTCAGGGGAACTCCCTCCCCTAGCCAAGGGA
AGCCCTGAGGGACTGTGCCATGAGGGACAGTGCTATCTGGCCCAGATACTACACATTTCCTACAGTCTTTGCAGCCGGCA
GACCAGGAGATTCCCTTGGGTGCCTACACCACCAGGGCCCTGGGTTTCAAGTACAAAACTGGGTGGCCATTTGGGCAGAC
ACCCAGTTAGCTGCAGGAGTTTTTTCTCATACCCCAGTGGCACCTGAAATTCCAGTGAGACAGAACCATTCACTCCCCGG
AAAGGGGGCTGAAGGCCAGGCAGCCAAGTGATCTAGCTCAGCAGATCCCACCCCCATGGAGCACGGCAAGGTAAGATCTG
CTGGTTTGAAATTCTCACTGCCAGCACAGCTGCCTGAAGTCAACCTGGGATGCTCCAGCTTGGTCGGGGGAGGGGCATCC
GCCATTACTGAGGCTTGAGTAGGCTGTTTCCTCTCACAATGTAAACAAAGCCACTGGGAAGTTGAACTGGGTGGAGCC
TACCACAGCTCAGCAAAGCCCCTGTAGCCAGATTGCCTCTCTAGATTCTCCCTCTCTGGGCAGGGCATCTGGGAAAGAAA
GGCAGCAGCCCCAGTCAGGGGCTTATAGATAAAACTCCCATCTCATGGGACAGAGCACCTGGGAGAGGGGTGGCTGTG
GGCCCAGCTTCAGCAGACTTAAATGTTCTTTGCCTGTTGGCTGTGAAGAGCAGTGGATCTCCCAGCACAGCACTTGAG
CTCTGCTAAGGGACAGACTGCCTTCTTAAGCAGGTCCCTGACCCTCGTGATTCCTGAGTGGGAGACACCTCCCAGCAGGG
GTCGACAGACACTTCATACAGGAGAGCTCTGGCTGGCATCTGGTGGGTGCCCCTCTGGGACAAACCTTCCAGAGGAAGGA
ACAGGCAGCAGTCTTTGCTGTTCTGCAGCTTCTGCTGGTGATACCCAGGCAAACAGGGTCTGGAGTGGACCTCCACCAAA
TTCCAGCAGACCTGCAGCAGAGGGGGCCTGACTGTTAGAAGGAAAACTAACAAACAGGAATAGCATCAACATCAACAAAA
AGGATGTCCACACGGAAACCCCGTACAAAGGTCGCCAACATCAAAGATCAAACATAGATAAATCCACAAGGATGAGGAA
AATCCAGCACAAAAAGGCTGAAAATTCCAAAAACCAGAATGCCCTCTTCTCCTCCAAGGGAGCACAACTCTTTGCCAGCAA
GGGAACAAAACTGGATGGAGAATGAGTTTGATGAATTGACAGAAGTATGCTTCAGAAAGTGGGTAAAAACAGACTCCTC
CAAGCTAAAGGAGCATGCTCTAACCCAATGCAAAGAAGCTAAGAACCTTGAAAAAAGGTTGGAGGAATTGCTAACTAGA
ATAACTAGTTTAGAGAAGAACATAAATGACCTAATGGAGCTGAAAAACACAGCACGAGAACTCTGTGAAGCATACACAA
GCTTCAATAACTGAATCGATAAAGCAGAGGAAAGGATATCAGAGATTGAAGATCAATTTAATGAAATAAAGCATGAAGA
CAAGATTAGAGAAAAAAAGAATGAAAAGGAAGGAACAAAGCCTCCAAGAAATGTGGGACTATGTGAAAAGACCAAACC
TACATTTCATTGGTGTACCTGAAAGTGGCGGGGACAATGGAACCAAGTTGGAAAACACTCCTTAGGATATTATCCAGGAG
AACTTCCCCAAACTAGCAAGACAAGCCAACATTCAAATTCAGGGAAATACAGAGAACACCACAAAGATACCCCTCAAGAA
GAGCAAACCCAAGACATGTAATTGTCAGATTCACCAAGGTTGAAATGCAGGAAAAAAAGTTAAGGGCAGCGAGAGAGAA
AGGTCGGGTTACCCAAAAAGGGAAGCCCATCAGACTAACAGTGGATCTCTCAGCAGAAACCCTACAAGCCTACAAGCCA
GAAGAGAGTGGGGGCCAATATTCAACATTCTTAAAGAAAAGAATTTTCAACCCAGAATTTCATATCCAGCCAACTAAGCT
TCAGAAGTGAAGTAGAAATAAAATCCTTTACAGACGAGCAAATGCTGAGAGATTTTGTCACCACCAGGCATGCCTTACAA
GAGCTCCTGAAGGAAGTACTAAATAAGGAAAGGAAAACCCGTACCAGCCACTGCAGAAACATACCAAATTGTAAAGAC
CATTGAAACTATGAAGAAACTGCATCAACTAATGGGCAAAATAACCAGCTAACATCATAATGACAGGATCAAATTCACAC
ATAACAATATTAACCTTAAATATAAATGGGCTAAATGCCCCAATTAAAAGACCACAGACTGGCAAATTGGATAAAGAGTC
AAGACCCATCAGTGTGCTGTGTTCTGGAGACCCATCTCACATGCAAAGACACACATAGGCTGAAAATAAAGGGATGGAG
GAAGATCTACCAAGCAAATGAAAGCAAAAAAAAACAGGGGTTGCAATCCTAGTCTCTGATAAAACAGACTTTAAACC
AACAAAGATCAAAAGAGACAAAGAAGGCCATTACATAATGATAAAGGGATCAATTCAACAAGAAGAGCTAACTATCCTA
AACATATATGCACCCAATACAGGAGCACCCAGATTCATAAAGCAAGTTCTTAGAGACCCACAAAGAGACCAAGACTCCC
ACACAATAATAGTGTGAGACTTTAACACCCCAATGTCAATATTAGGTCAACGAGACAGAAAATTAACAAGCATATTCAGG
ATTTGAACTCAGCTCTGGACCCAGTGGAACTAATAGACATCTACAGAACTCTCCACCCCATATCAACAGAATATACATTCT
TCTCAGCACCACATCACACTTATTCTAAAATTGACCACATAATTGGAAGTAAAACACTCCTCAGCAAATGCAAAAGAATG
GAAATCATAACAAACAGTCTCTCAGACCAAAGTGCAATTAAATTAGAACTCAGGATTAAGAAACTAACTCAAAACCATAC
AACTACAGTGGAAACTGAACAACCTGCTCCTGAATGACTACTGAGTAAATAACAAAAAGAAGGCAGAAATAAATACATT
ATTTGAGACCAATGAGAATAAAGATACAACATACCAGAATCTCTGGGACACAGCTAAAACAGTGTTTAGGGGAAATTCAT
AGCAATAAATGCCCACAGGAGAAAGCAGGAAAGAGCTAAAATCAACACTCTAACATCACAATTAAAGGAACTAGAGAA
GCAAGAGCAAACACATTCAAAAGCTAGCAGAAGACAGAGAAATAACTAAGATCAGGCAGCAGAATGTGAAGAGGATTAGAGA
CACAAAAAACCCTTCAAAAAATCAGTGAATCCAGAAGCTGGTTTTTTGAAAAGATTAACAAAATAGATAGAATGCTAGC
CAGATTGATAAAGAAGAAAAGAGAGAAGAATCAAATAGACGCAATAAAAGATGATAAAGAGGATATCACCACTGATCC
CACAAAAATACAATCTACCATCAGAGAACACTATAAACACCTCTATGCAAATAAACTAGAAAATCTAGAAGAAATGAAT
AAATTCCTGGACACATACACCCCTCCTAAGACTAAAGGAAGAAGTCAAATTCCTGAATAGACCAATAATAAGTTCTGAAAT
CGAGGCAGTAATTAACAGCCTACCAACCAAAAAAAGCCCAGGACCAGACGGATTCACAGCTGAATTCTACCAGAAGTAC
AAAGAAGAGCTGGTACCATTCCTTCTGAAACTATTCCAATCAATAGAAAAGGAGGGAATCCTCCCTAACTCATTTTATGA
GTCCGGCATCATCCTGATACAAAAACCTGGCAGAGACACAGCAAAAAAATAAAATTGTAGGCCAATATCCCTGATGAAC
ATTGATGCAAAAATCTTCAATAAAAAACTGGTAAACTGAATCCAGCAGCACATCAAAAAGCTTATCTACCATGATAATTT
GGCTTCATCCTGGGATGCAAGGCTGGTTCAACATATGCAAATCAATAAGATAATCCATCACATAAAGAGAACCAATGA
CAAAAACCACATGATTATTTCAATAGATGCAGAAAAGGCCTTTCATAAAATTCAACAGCCCTTCATGCTAAAAACTCTCA
ATAAACTAGGTATTGATGGAACATATCTCAAAATAATAAGAGCTATTTATGAGAAACCCACAGCCAATATCATACTGAAT
GGGCAAAAGCTGGAAGCATTCATTTGAAAACCGGCACAAAACAAGGATGCCCTCTGTCACCACTCCTATTCAACATAGTA
TTGGACGTTCTAGCCAGGCAATCAGGCAATAGAAAGAAACATAAAGCATATTCAAATAGGAAGAGGAGGAAGTCAAATTGT
CTCTGTTTGCAGATGACATGATTGTATATTTAGAAAACCCCATCATCTCAGCCCAAAATCTCCTTAAGCTGATAAGCAACT
TCAGCAAAGTCTCAGGATACAAAATCAATGTGCAAAAATCACGAGCATTCCTATACACCAATAATGACAAACAGCCAAGT
```

FIG.2 (Continued)

```
CATGAGTGAACTCCCATTCACAATTGCTACAAAGAGAATAAAATGCCTAGGAATACAACTTACAAGGGATGTGAAGGAC
CTCTTTAAAGAGAACTACAAACCACTGCTCAATGAAATAAGAGAGGACACAAACAAATGGAAGAACATTCCATTCTCATG
GATAGGAAGAATCAATATCGTGAAAATGGCCATACTGCCCAAAGTAATTTATAGATCCAATGCTATCCCCATCAAGCTAC
CATTGACTTTCTTCATAGAATTAGAAAAAACTACTTTAAATTTCATATGGAACCAAAAAACAGCCCGTATAGCCAAGACA
ATCCTAAGCAAAATGAACAAGCTGGAGGCATCATGCTACCTGACTTCAAACTATACTACAAGGCTACAGTAACCAAAACA
TCATGGTACTGGTACATAAACAGATAGATAGACCAATGGAACAGAGCCTCAGAAATAACGCCACACATCTACAA
CCATCTGATCTTTGACAAACATGACAAAAACAAGCAATGCAGAAAGGATTCCCTATTTAATAAATGGTGTCGGGAAAACT
GGCTAGCCATTTGCAGAAAACTGAAACTGGACCCCTTCCTTACACGTTATACAAAAATTAACTCAAGATGGATTAAAGAC
TTAAACATAAAACATAAAACCATAAAAACCCTAGAAGAAAACCTAGGCAATACCATTCAGGACATAGGCATGGCAAAGA
CTTCATGACTAAAATACCAAAAGCAATGGCAACAAAAGCCAAAATTGACAAATGGGATCTAATTAAACTAAAGAGCTTCT
GCACAGCAAAAGAAACTAACATCAGAGTGAACAGGCAACCGACAGAATGGGTGAAATTTTTTGCAACGTATCCATCTGA
CAAAAGGCTAATATCCAGAATCTACAAGGAACCTAAACAAGTTTACAAGAAAAAAAACAACCCCATCAAAAAGTGGGCG
AAGGGTATGAACAGATGCTTCTCAAAAGAAGAAATTTATGCTGCCAACAAACATACGAAGAAAAGCTCATCATCACTGGT
CATTAGAGAAATGCAAATCAAAACCACAGTGAGATACCATCTTATGCCAGTTAGAATGGCGATCATTAAAAAGTCAGGA
AACAACAGATGCAGGAGAGGATGTAGAGAAATAGGGAACACTTTTACACTGTTGGTGGGAGTGTAAATTAGTTCAACCATT
GTGGAAGACAGTGTGGTGATTCCTCAAGGATCTAGAACCAGAAATATCTTTTGACCCAGCCATCCCATTACTGGGTATAT
ACTCAAAGGATTATAAATCATGCTACTATAAAGACACATGCACATGTATGTTTATTGTGGCACTATTCACAATAGCAAAG
ACTTGGAACCAATCCGAATGCCCATCAATGATAGACTGGATAAAGAAAATGTGACACACATACACCATGGAATACTATGC
AGCCATAAAAAAGGATGAGTTCATGTCCTTTGCAGGGACATGGATGAAGCTGGAAACCATCATTCTTGGCAAGGTAACAC
AGGAACAGAAAACCAAACACCACATGTTCTCACTCATAAGTGGGAGTTGAACAGTGAGACACATGGACACTGGGAGGA
GAACATCACACACTGGGGCCTGTCAGGGTGTAGGAGGCTAGGGGAGGGATAGCATTAGGAGAAATACCTAATGTAGATG
ACAAGTTGATGAGTGCAGCAAACCACCATGGCATCTGTATACCTAGGTAACAAACCTGCACGTTCTGCACATGTACCCCA
GAACTTAAAAGTATTATTATTATTATTATAATAATAATAATAAAAGAAATACAATAAAATAGAATGCAGCATACAGCAGT
GATTCTCAAACACATTCAGCATCAGAATTACCCTTGAATCTCTTTAAAATATATATACATATGAGATCTTAGTCTCCAAGATT
TGTAAGTTTGGTATTGGGTCCCTGGGCCTATGTTGGGTTTAGAAACTTCTACAGATGGTTTGGATGTATGGGACAGTTTAA
GAATCGCTGAACTAAAATCAAATAAACTGAATATCCTGTGATTAGAGAGACTTATCGTTTATTTCACTATCCAAGTACTT
GCATTAGAGCGTGGCTAGAAGGGATTTGCAGCCTTGTAAATAATCAGAAATTCAGACATTTTGAGATGAGAGAACTGCTG
AAGATTTTATTCTGACTTGAAATAAATTTCTAATTAGAAACTTCCAGGTGAGAGCAAAGGCCTGGAACAATATTCCTGAG
CCAGAGGAGGATCGAGTTTGACTCCAGGCCTAACACTTACTAGGTCTATGACCTTGGGTCAGTAATTTAAATTCTCTGTAT
CTCAACCTCTCAACAGGGTATTGGTAGGGATTAAATGTGTTAGTGTCTGTGAAGTGCTTAGAGCAGTGCTTGGCATAGTAA
ATGCTTAATGAATTTCAGCCACTGTTTTATTTTTAGTACTTTCCAGCTCCCCCAAAAAGATACTTTTTTAGACTTGTATTA
AGACAATAAAAAGTTTAATCAGCATGCTTCATACCTAAATATGCTTCACTTTATAGCAAAGTTTACAAGACTAAAACTGTT
TTGTGTGTAATTCTCTGAGTCTCATGTGTTTATTAATGATTTTTTCTGCTGTTTATTCATCTGAATTCTACTCATTCTTCAAGA
CCTAGCTGGAATCCTGTTTCTAGAAAGACTCTTGCCCATAATAATAAACCTGCCCTATCTGAGTTCCTAGGTGGGTCTGTAC
CTCATAATTTGGTAATTAATTGTATATGCACTTATATAACAAAACATTATTGTGTGTCTTTGCTGTATCAGATTCTAGGCTG
GAAGTTGTAGATATGATGTTTTTGTCTAGAAAAATGTTCTAGAATGTCCTACTCAGGACAGTCTGTTGACTTAAAGACAC
ATTTCCTAAACAGACACTTCATGAGGCAGCCCCAGCCTGCTACCTGTGTTCCTGGACCTGATGATCAAGTTTGATTTAAGCC
TCACCACTTACTAGCTCTGTGATTTTGGGCAAGTTACTTGAACTCTTCTGTGTGTAGATAGAACAATGTTGAGGGAAATCCC
TTTCCCCCATCCTTGTGTTTCCACAAGGGAACTTGCTTCCTAATAAGTAACACTTTCAGGGGAATATTCTAGGCCCTTCTCT
TATCCCCATTACTTGTTCTTTCTGTGAAAAGAGGAGAGGGTTAATCTGATGGATGAAATCCTAATCTTTCATCTTCTGGACT
GTAGAGCCTGTGAACCAAAGCAATGGACCACTTGCACTGAAATTGAGGCTGACCCTGTATTTTGATTCTTATTTGGCAACT
TATTTCTATTCTGTTCCCAATTCAAAATCCCAAGGGGAGAAGGAAGGAAAATAATTGATTACCAGAAGTATGTAAATGGTGGTAG
GAAGTTGAATAAATGGTAACTTTTTAAAAGTTGCATGAGATATAGTCCTTATCCCAGAGAAGCTAAGTTTGCTTTTCTTTC
CTCTCATGTATTTAGTATTATTTCTACAATTAGATTGTAAACCCTTAAAAGCAAGAATATTTCTACATTTTCTTACTCCT
GATAGCACACAGTAGACTGCTGGGCACATACATAGTAGGTGGCTCTGTAGGTACTTGCTAAATGATTCAACATGTTTTTCC
CTCATGGAAAAGAAAGATTTCAGTATTGTTCTTATCAGCTAGGAAGGCACTCTGAATAGGAAATCAGTTCTAGGCAGGTA
TCCATAAATGGGTTATGATTTCCAACTTACTTGCCCCAGAGGCTCGCTAATGTTGAACTCTTCATGGGTACTTTGTCTTGCT
TCATGAGCTATACATGCTAAGGGGTTAGCAGATCATATAAACTTTTGATCTACAAAATATGATCTTTATTGAACAAAAACT
TGGGCCAAAGGCCTTTCTCCTTTGCCACCTTCCTCCCTCTTTCATTCTCTTTTTGGGAATGCCCTTTGTGCATGTTAGTTA
CAGCATGTACCACATTGCACTGTATTGTTGGTTTTGGGTCTAACCCACCCCTTAACACTGCAGTCCCCAAGGGGCAGAAATT
CAGTCTCATTCATTTTGATGTCCTCAGTGCCTGTGCTCAGAGAATATCTATTATTTGAAAAAATAGTGCAAAAGTAAATTT
TAGGAGACTACATCACACTCATCTAAACTGCAAGTTTGACAAGTTGACATCCAAAAGAAAGGCTCTCCTAAATAACCTCG
CCACAGAAATTTGGGTGACCTTTGTAGCTCTGGAGAAAGCAGAGGCAAAATGAAACCTAAAAATTATTGTGGGTTTTT
AAAAAATGTTTCTCATGGAGTAAAGGTCTACAGCTGAGTTCTTTCATATGAGGGAATGACAGAAACACAGCTGGTTCT
GACTTTCAGCTTCAACTGAGCGACCAGAGCTCTGCTGGTGAAACAGGAACTTGTATTGTGCCCTGACGTGCACCTTGAA
GGGTCAGCTCAGTGTCCCTTTGTCACATAAATAGTTTTTAAGAATGTTTTTGATCTTGTGAGCCTCTAACTAAATGAT
TAACCATGCAAAGTTGGCCATTTGGGGTAATACTGAAGCACTTCTCTTGAGGGCTATTGACAGGTGGGAATGTGCCCACC
TCCTTGGGTCTCTGGTTTTCATGTCATACTTGCAAATCAGTGACAGTTTAAACTTGGGGCAATCACTTAGCAAGTCTATTG
```

FIG.2 (Continued)

```
AGTTACCAAGTTAATTATTCCCACTTTGCATGAAGCAACCTTGAAAATGATTTTCCTAAAGCAAAGTACATCCAAACTCAG
TACCTTCTTAATAACCTTTGCTGAATGAATAAATGACTAATTCATAAAAAATGTAACATATCTTTAATTCTTACTTACGGG
CAGTTTAAGCCTCTTGTGTAAGAGGAGGGCCTCGGCTTGAGATAACATAGGATAGTAAGCCTCCTAGAGAAATTTCTATAT
GGAAACATGGTCTGCTATGAAGCTAGAAGTGAGAGGACATTATATTTGACCATTATATTTGGCTTCAGAGCTTCTCAACAT
GGGGGCCCAAAGTCAAGGTCCCTTGTTTCATTAAGAGGAGGTCCAGGAGTGCATGACACCCATCAGACTACTGAGACCCAG
CTGGAACTAGGCACCTTGCACAGGGGCCTTGCCTAATCAAAATAGTTCTTATTTTTTCTGAGTTCCAAGTAACTAGTTTCCT
AACCCAGTGTCTCGATAGTAGTGCCAAGTGGGAGTACCTTCAATGAACTTCCTCATGAGGTTATTTCTAGCCTATTGGAAT
GTTTCGTTTTAGGAGGGTGAGGAAGGGAAGTCTTGAATTTTTGTGCTTAGTTTAATGTTGTGATACAGCTTTGACCATCCG
TTTAATGGGAGATCTGTTTTCCAGATGACTATACATGTGGAAAGGAGAAGTTTTTTGAGTGTTTTTTTAACCCCTTTTAAA
GAATGGTTTTCATTTAGTCTCTACATTTGGGGGTAAAAGGTCCTCTAGGGAGACTTTTCAAAAGTATTTGAAGTTGCAT
CTGATTTCAGAGGTGAGTTGGAGGCCTATCTGTGTATGACAGACACATGTCTCCAACAACTATATGTTCACAAGGACTAA
GAGCCATCCTTTTGGGTCCATCATTCAACATTGATCTCACATTCGTGTTCGTATCAGTATCTTTACAGTGCGCTCCCAGTA
CATCTCCCTAATTTCCCTTAGTAGGCTTCACAGAATTTGCAGTGTATGCAATGGCAGATGACCACATGTGGAGTCATTTAA
CCACATCTTCCACTGCAAGTCAGCCCGCTCTTGATGTCTGTTTATGTTAGATTCCATCTTTTGGAAGATTTCATTCCTCTG
CACTATCTCAGTATCTCAGATGCTTTTGAGACTGGGTCCTTTTCCCCTCCTATGTTTGGCCATGGCCACCCCCTCAGGGTTG
TGTTGTGTTCACAGCTGCTGTTTGTAGGGTTGACCTTTACAATGTACAAAGTCTTTCCCATATGTTGACAATCCCTGGTG
TGATGCTGTGAGTTAGGCAGGGTGTGTATACGTGCCTCATCATATTACAGTGGTAAGGCAACAGGGTTTTTGAATTTGAT
CACCCATGAATTTGTCTAATTTGTTGGTAAAAAATGGTCATGTATCAGCCGTTTCACAGGGGTCAGCTTAATAGAAAGTGGG
AGTTAGGCAGGACCAGAATTCAGGACTTCAGCCCCCGGTCCCAGGGACTATTCTCTATACCCAATTGTCCCACCTTGAATC
AGTTTCTTCTAGGGAAATATCTCCAAAACTGAGATGGCACCCACAGGACTTCTTAATTGTAGTCATTACCAGGAAAAACA
AGCAAAGGAACTGGTGTAAATCTCTGTTTTTGGTGATTGGTGAGATTTGGAGATTGTCTTGTGTCAAAAGTAAAGCCACT
AGATTAAATGTTTTGTTAATAAATTGGTTATTTTTAATTTAATTATTTGACAGTTAATTTACATTATTCAAAAATCAAAATA
AAATTTAAAAGAAGTTTACACTGAAAAGTCTTGCCCCACTTATACCCTGCTCACCTCAGTATCCCCAATACATACCATCT
ATAAGGTGATCATTTGTATTAGTTTCTTGTGAATCCTTGATAGTGTGTTTTATATAGATACAGGTAAATATGAGTATGTACT
ATTATTTCCCCCCCCACCCCACCCTGTTTTTTTTTTGAGACGGAGTCTCGCTCTGTCGCCCAGGCTGGAGTGCAGTGGCACGA
TCTCGGCTCACCGCAAGCTCCACCATTTTCCCCCATTTTAAAACAAAAGGTAGTAGCCATATATACACTATTTACACCCTT
GTTTTATCACTTACTAATATATACCAGAGAGCTTTCCATCATTTTGTACATATGCACCTATATCTGTCAATTATTCCCAGAA
GTGGAATTGCTGGGTCAGCAGGAAAAATCATGTATAATTTTGATAGGTATTGCCTAATTGTCCTGCACAGGGCTTGAATTG
TTTGTACTCCCACCTTTAGTGTATGAGAAGACCTGTTTCTCCATAGCCTCATCAAACAGAGTGTGTGAGATTAGATGAGAA
ATAGGAGGTGAGCAGTCTTTTACCCCATCCGTAGTTTGCAGTGGGAACACTGCACAGTTGCAAGAGCTGGTGCAGGTATC
AGATTAGTTCCAGTGGAAACGCTGCCTCACCATGGCCATGGGCTTGCGCCAGCTCTAGTGACACACACGGAATGGACCCA
CGTTGCCACTTGCAGAATTTCCTGTAGCAGAAAGTTGAACATGCATTCATTATTCATCTAACTAGCCATGCTGGATCTAAA
GAGCACAACAGTGTTTTTAGAACCAAAAAGAAAATTGTTTCACTACAACACACTGTGTATAAGGCTTTCAATGCTCTTTT
CTCAGCTATTAACATTATTTCAGGACTGAGTTCAAGAGATGTATCCCAAATCACAGGGATGTCTTGCTAAGCTTGGAACT
TTCATACTCAAGGGATGCTTTTTTGAGGGAATGATTTTACACTTACTCAACATTTGTAATTAAATAATTAGTACTTTATAAGA
TAAATTTAAACTGTCCAAGTACAATATAAACATTGAACTATGATGCATTATTGCTAGACTTTTTCCTTAAAGTTGCCAAGT
GGTTTCCTGCATTAGGCAAATAGGGGATCATATAAAAATGCCATGATTTACGGCCTAGATAACATCTCCACCATTTGAGC
AGCATATATTCCAGGTCATCCCCACATAACTCCTTACCATTCTCATTAGAAAGGTTGATTCTTAGTCTTATTTTCTCTGAG
GACAGCAAAAAAAAAATCCCCTTCAGTCCACTGCATAGAAAAGTGTGGTAAATGGAGCCGGGCACAGTGGTTATTTAA
TTTAAATGGACAATATTTTTATAGAATTTTGACAGGGGCCACTGTATAGGGGAAAGTCACTCCTCTTCCCCTTTATAGAAG
AGTTGCACCTGGACAGTGCATTGATGACTGTATCCAGTCTACAACAAGAGGTCATTCCTGGGCATAAGAATGGACTGCCA
AAATCTAGCTGAAACACCATTGACAAATAGACATTTTCTTTTGTTAATAATACCTGTGAAGGCTTCATAACAGACATTTC
CAGTTTTGTTCTCAGGCTCCTTGCAGCTGCTCCTCTAAAAGTGTGCTCTCTTCCAAGAGCTGACAATGGCCAGAAGCAAGG
TGTTCTGTCTTTTGTGCCATCATCATCTAACTTGCCACACACATTAGGGTGCAGGATGTCAGCCTGGTATAGGTTTTGTATCCACTC
AGTATGGCTTGTGGGTCTGGTTGCCTTTGTTATTCATGCTGAGGGCCTCTGGGCATCAGTTTGGTGTGAGAGAACCCATTC
CATGACCCTCCTTCCTTGGCTGTTTGACTCGATGGCTCTTGTTGGCACAGTCTGTGAGTGTCTGATGCTCTATCCATGCC
GGACCATCTGTTCTGCTGTCTCTGTGGTCTGAAGTCGTTTTCTGAACTATTCCTTGATAATAAATTTGAGATGATCTTGTTC
TACCTTTCTTTCAAGTCACATCTTAGCCCCTTAGCCACACATTCCCGAAGAACATGACAAATGGATGGGTCACAAGTCACGT
AGCATAGGGTGTCAGACCACGAGGCTTTGAAGGGATTCTGTTGGGTGCTAAAAAGAAAGATTTTGTGTCACCACGATTTT
TTTTAAAGGCATGTTGACACTTAGGCCTTAATTGAAAGCGTTCTTACTCAAGTAGAGTTGACAGAGGAGTATTTGGTAGTC
GCGGTTGCTGGTCTGAAGAGCATGTGGTTCTGTTTCAATGCCCAATGAGATCTTCTCACGGGAAAATGTTCTGACATCTCA
AACAAATGACCTTCATGCATAGTTTTGACAAAATACCCTATTAAGTATGCATATATGGTTGGTACCTTGTGGTAATAATTC
AATACTGAAGGTAGCAACAAAGAAACATTAGGGTTATATTTAACCTCTGTGGAATTAGTGTGTAAACAAACTGCT
TATCAGAAATGCTCATATGGGGCTTTGTTTAAATAAATAAGAAACTGGCATATAGGGTCTGCAGGATATTCTGCCAAGT
AGACCTCCCTCACATTATAAGACACCACATCTATGTCTGACCCCATATGGAAAGAGGCATAGCCAAGCCAGCACTGGTTCA
TATTCCCTCTCCACCACATAATGGGTATGTGATCTTAGGGAATCCACCGAAACTCTCTGGGCCTCAGTTCCTTCAGCTATA
AATGGTGGATAATCAAATTATTTACCTCACCATTAATAAATGTTAGCTATTATTTTTTATCAAGTTTAATACAAAGAGAAA
```

FIG.2 (Continued)

```
CATTTACTTATTTTTCCAGCTATCCAGAGCATCTTCCAAAATCCTATCACCAACAAATACTGTATTGTATTTATTATAGCA
ACTATGTAAAAATGGAGTCCCTGTCCTATGCTTAGATGAAATATGTTGGTATTTGAGTTTGCATGTCTTCTATAGGAATCA
GTGTTTAGTGAAAACGGGTGGAGATAAACAGATGTTTTCACAGTCCTGTTGTTCACAGTACCGCCAAATTGAATGTTCCA
TATAGGTGCATTCTAATGGCTTAAATGATGCAGATATTTCTGGCCAGCCATATGGATCTTTTGTCATCTAAGATGTTAAT
ATTTTCCTTATATTTTATAGTAGTTCTGGAGTACAGCCAGTTTCTTGAATAGGGTCCACATGGCTCATTATGCACAGGGCCT
GGAAACTGCCTTACTCGTGCTGTTGAAATGAACCGTGACACTTCAGAAGAGCTGGGAGCTGGGGTAGAGCAGTGGCTAGG
AGAACATATTCAATTATATTTCCTCCTGCATTAAGCTACAAGTAATGAGCACTTTCCTGTGCTTTACAGTTAAGTAATTAA
AAGAAATTATAGAGTGGGATGCAAAAATAACCCGAAGGACAACTGGATGTGTGGAGCCACCAGTTTCTCCATGAGTGC
ACAAGGTTAATCCTTGTTACTACTCAGAATGCTGAGTTTCTACAGAAAGGGTTGCAGGTCCACACATGTTTGGCGTCTAC
CCACACGCTTCTGTATGGCATGACTGTGCATCCCAGAAGAAGGGCTGTGCTGTGTACCTCCACGTTTCAGTGGAATTTAAC
AAACTGATCCCTGAAAATGGTTTCATAAAGGTGAGTAACAGAGAGCTAATAGCCTTCTCTTGCTAATTTTATCTTTCCCCC
AAGATTTCTTGATAATAGTTTGAAAAGGAGTGTTATTCTTTGGTCTCTAGAGGCAACTTACCTTTCCAGTTTCTTCCATCAC
CTGTTTCATCTCTCTTGTTTTTTAAATTTAATGCTGTATGTATTTCAGAGGATAGGATCTAATCTAGTGCGGTCCCTTCAT
CAGGTGAGAATTATTCATCTCATTTTCATTTTAGCCCTTCTGAATTAATGACATTGAAGCCCGGCAGTTTGGTCCTAAGAT
GGGTTTAATTATGTACAGATACTCTTTCTATAATGGAAATTGCTCAGATAACTAATTAACCACAAGAATACACTGTCTATG
GAAAATTTCAGGAGCACCGTCTGTGGAAAAACTGGGAAGGGCATGCTGTCACCACAGCTCTGGGGTCTATTAAAAGTGTG
GTTATGCAGCACTGGTGTCTAGTGGGGTGTTGGCTCTCAACTGCCAGAATTCCCATAGCATTTCATGGCAGAAAGTCAAG
GTGTCCAGCAATACTCTGAAAGTGACCTGTTGATTAAAGTCGTCAATTCTGAAGAAAGAGACTGAAATAAGACAAATGGG
TCTTAACTTTTTCTCTTTCTCTCTCTTGTAAAAATGTGTGATTGTTCTGGCATGTTCCCAATCCCACATAATGCCAACAT
CTTTTCTTAAAGGGGGATTCCCTTTATCCTTGGATCTGAGAATTATTGCATGTTCTCCCTTTAGGGACAATGAATGCAGTTG
CATCACCCTTGCTTTTTTTTTTTTTTTTGTACACAGCATGCTTATTCTTGGATGCAGGGACTTGAAAGACAAAGCCCCACCT
GGCTTTCACAACATCTCCTATTAGTAGGGTGTCTGTGTAATTGAAGGAGGCGGTCCCTTAGCTGTGTTACACTGT
ACTTTTAAATGTGGGGCTGAAGGTAGAATCAACCATACTTAAGATGCCACCTGGGAAAATAGGGTTCTGTGTCATCTCAG
CCCCCACCCATTTGCAAATGACTTAACAGCAGCACTATTAGGGTTCCTAGTGTGAGTCATTTGCATTTGGACTGGTGAACTT
GGTGACTTCTTGGTGTTTGGAAACAAACAACCTTTGCAGTCTTTCGTAAAAAGCCTGAACAGTGGACCAGTCTCCAGTTCT
ACTTGCAAAGCTGCCCCCATCAAATCCCTCATAATGTTCAACTTAAAAAATGTTACACTTTTCTCTGGAAATCTAACCTTTT
TTCCTTTTTAAAAGCCATTTTAAGTACTTCAGTCTTGAATCAAATGATCCCCAAATATTGGACACCAACCTAGAAATTGGG
TTACCTCCTGGGAACTTTATCGAAGAAGAGAGATTTTGGTTGAGAGGGGGTTTTGATGTTTGATACTTATATTTACTATT
TTAATATTTCATTGTTGTTGTTGCTGCTGCTGCTGTATTATTTTGCGAGTTTCGTTTGTTAAATTTCATGGTATTTGGTAGG
AGAGAGCTGGATCTGTTGGTTTCAGGACAAGTCTAGAAATAAGAAATCTGCCTTGAGTGAGTGAGTTGGTTCCCTCTGTTG
CTATTTCACCATTAAGGACGAAAGGAACTCACAAGGACCAGAGACATCTGGCTGAAAGCAATACTAGTGTGACTGGACAT
CTACTACCTGCCATAGTTGGTCATATCGTTTCCAGTATGATTCTGATTGAGTGAGTGATATTAGGCTATGTTCAGGGATCA
GGGAGGCTAATTATGCTTATATTGCCTTGTAGCATTTGGTAAGAATTAATGATTGTGTAGATGTCCAGATTAGGTCAGC
AATATTCTAAAAGTTCTCATTGAACTAATCATGTTTATAAGTAGCCTGTACTTTCTATCATAATAACAATAGTGGAAAAGC
TAGTTGACATAAAAGGAGCCCAGATTTTACTTAAGTAAAAACAACAAAAGCAAAGATATTTCCCACATAAATTACAAAKG
CAAAGATATTTCCCCACATAAATGTCCCCATAAAACAAGTTGAACCAAAGAGGAAAGATGACAGGTAACCGTATGACAC
GCTAAGAAAGTATCATAATACTTAAGTTAACTTCAACCTTTTATTTCCTATCCTAAGCAGCCTCTTTTCTCTTTATCATTTA
GTCCTGTGCTTCTCAACTTTGATAAGTAAAAAAGTTATTGCACTAAATAAATCTTATTGAAATGCAGGATCTGATTGAGTG
GGTGGGGTAGGTGGAATGAGGGTGGGGAAGTTGAGATTCTGCATTTCTTAGAAGTTTCTACTTTATGTTAAAATGGCTAAT
CCATCTCAACATTGAGAAGTAAGGTTTCACTTAATTTCAGCCTGTGTAAGTTTATCCCCATATGTACATTTCCTAAAACTCTA
ATCTCAGGCCCCAGGAATTTCTCCCTTTAGTTAAAATATTTTTAGGGAATAAATTTGAATTGCATTAATACACAATTTATAAA
TTTAACACAAAAATTATTTGAAGTTTGAGACTTTAGGTTGCATGAAATCAATTTCATACTTGAAAATTTTCTATAAATTC
AAAAGTCTGTGTATTTAAATACAATTTAAATACCTGTGTTACAGTGACATTTGTTTTCTGTCTCTCTCTCCACCATTTCCA
GAGTCATCATCCCTGTACAGAAAATTTTCCCACACATGATTTCACCATAAATTCATTAAATATGATGCTTACTTGATAATT
CTCCAGGTTCTTTTTTTTTTTAATTATACTTTAAGTTCTAGGGTACATGTGCACAACCTGCAGGTTTGTTACATATGTATAC
ATGTGCCATGTTGGTGTGCTGCACCCATTAACTCGTCATTTACATTAGGTATATCTCCTAATGCTATCCCTCCCCCCTACCC
CTACTCCATGACAGGTCCCAGTGTGTGATGTTCCCACCCTGTGTCCAAGTGTTCTCATTGTTCAGTTCCCACCTATGAGTG
AGAACATGCGGTGTTTGGTTTCTGTCCTTGCGATAGTTTGCTCAGAATGATGTCCTTGCTCACTGATGGACATTGGTTGG
CTCCAAGTTATTTGCTATTGTAAATAGTGCCGCAATAAACATACGTGTGCATGTGTCTTTATAGTAGCATGATTTATAATCC
TCTGGGTATATACCCAGTAATGGGATGGCTGGCTCAAATGGTATTTCTAGTTCTAGATCCTAGAGGAATCGCCACACTGTC
TTCCACAATGTTTGAACTAGTTTACAGTCCCATCAACAGTGTAAAAGTGTTCCTATTTCTCTACATCCTTCCAGCACCTGT
TGTTCCGGACTTTAATGATCGCCATTCTAACTGGTGTGAGATGGTATCTCATTGTGGTTTTGATTGCATTTCTCTGATGGC
CAGTGATGATGAGCATTTTTCATGTGTCTTTGGCTACATAAATGTCTTCTTTTGAGAAGTGTCTGTTCATATCCTTCACC
CACTTTTTGATGGGGTCATTTGATTTTTCTTGTAAATTTGTTTAAGTTCTTTATATCTGGATATTAGCCCTTTGTCAGAT
GGGTAGATTGTAAAAATTTTCTCCCATTCCGTAGGTTTCCTATTCACTCTGATGGTAGTTTCTTTTGCTGTGCAGAAGCTCT
TTAGTTTAATTAGATCCCATTTGTCAATTTTGGCTTTTGTTGCCATGCTTTGGTGTTTAGTCATGAAGTCCTTGTCCATG
CCTATGTCCTGAATGGTATTGCCTAGGTTTTCTTCTAGGGTTTTTATGGTTTTAGGTCTAACGTGTAAGTCTTTAATTCATCT
TGAATTAATTTTTGTATAAGGTGTAAAGAAGGGATCCAGTTTCAGCTTTCTACATATGGCTAGCCAGTTTTCCCAGCACCA
```

FIG.2 (Continued)

```
TTTATTAAATAGAGAATCCTTTCCCCATTTCTTGTTTTTGTCAGGTTTGTCAAAGATCAGATGGTTGTAGATGTGTGGTATT
GTTTCTGAGGGCTCTGTTCTGTTCCATTGGTCTATATCTCTGTTTTGGTACCAGTACCATGCTGTTTGGTTACTGTAGCCTT
GTAATATAGTTTGAAGTCAGGTAGCGTGATGCCTCCAGCTTTGTTCTTTTGGTTTAGGATTGTCTTGGCGATGCGGGCTCTT
TTTTGGTTCCATATGAACTTTAAAGTAGTTTTTTTCCAATTCTGTGGAGAAAGTCATTGGTAGCTTGATGGGGATGGCATTG
AATCTATAAATTACCTTGGGTAGTATGGCCATTTCATGATATTGATTCTTCCTACCCATGAGAATGGAATGTTCTTCCATT
TGTTTGCGTCCTCTTTTATTTCCTTGAGCAGTGGTTTGTAGTTCTCCTTGAAGAGGTCTTCCACATCCCTTGTAAGTTGGATT
CCTAAGTATTTTATTCTCTTTGAAACAATTGTGAATGGGAGTTCACTCATGATTTGGCTCTCTGTTTGTCTGTTATTGGTGT
ATAGGAATGCTTGTGATTTTTGCACATTGATTTTGTATCCTGAGACTTTGCTGAAGTTGCTTATCAGCTTAAGGAGATTTTG
GGCTGAGATGATGGGGTTTTCTAAATATACAATCATGTCATCTGCAAACAGAGACAATTTGACTTCCTCTCTTCCTATTTG
AATATCCTTTATTTCTTTCTATTGCCTGATTGCCCTGGCTAGAACGTCCAATACTATGTTGAATAGGAGTGGTGACAGAGG
ACATCCTTGTTTGTGCCAGTTTTCAAAGGGAATGCTTCCAGCTTTTGCCCATTCAGTATGACATTGGCTGTGGGTTTGTCG
TGAATAGCTCTTATTATTTTGAGATATGTCCCATCAATACCTAGTTTATTTAGAGTTTTTAGCACAAAGGCTGTTGAATTTT
GTCAAAGGCCTTTCTGCATCTATTGAGATAATCATGGTTTTGTCTTTGATTCTGTTTATATGATGGATTATATTTATTGAT
TTGCATATGTTGAACCAGCCTTGCATCCCAGGGATGAAGCCAACTTGATCATGGTGGATAAGCTTTTTGATGTTCTGCTGG
ATTCGGTTTGCCAGTATTTTACTGAGGATTTTTCCATCGATCTTCATCAGGGATATTGGCCTGAAATTCTCTTTTTTGTTGT
GTCTCTGTCAGGCTGTGGTATCAGGATGATGCTGGCCTCATAAAATGAGTTAGGGAGGATTCCCTCTTTTCTATTGATTA
GAATAGTTTCAGAATGGTACCAGCTCCTCCTTATACCTCTGGTAGAATTCAGCTGTGAATCCATCTGGTCCTGATGGATTT
TTTTGGTTGGTAGGCTATTAATTATTGCCTCAATTTCAGAGCCTGTTATTGGTCTATTAAGAGATTCAACTTCTTCCTGGTT
TAGTCCTGGGAGGGTGTGTGTGTGTCCAGGAATTTATAAATTTCTTTTAGGTTTTCTAGTTTATTTGCATAGAAGTGTTTATAG
TGTTCTCTGATGGTAGTTTGTATTTCTGTGGGATTGGTGGTGATATCCCCTTTATCACCTTTTATTGCATCTATTTGATTCTT
TTCTCTTTTCTTCTTTATTAGTCTTGCTAGTGATCTATCAATTTTGTTGATCTTTTAAAAAACCAGCTCCTGGGTTCATTGA
TTTTTTGAAGGAGTTTTTCTGTCTCTATCTCCTTCAGTTCTACTCTGATCTTAGTTATTTCTTGTCTTCTGCTAGCTTTGAAT
GTGTTTGCTCTTGCTCTCTAAATTGTGATGTTAGGGTGTCAATTTTAGATCTTTCCTGCTTCTCTTGTGGGCATTTAGTGC
TATAAATTTCCCTCTACACACTGCTTTAAATGTGTCCCAGAGATTCTGGTATGTTGTGTCTTTGTTCTCATTGGTTTCAAAG
AACATCTTTATTTCTGCCTTCACTTCGTTAAGTACCCAGTAGTCACTCAGGAGCAGGTTGCTCAGTTTCCATGTAGTTGAGT
GGTTCTGAGTGAGTTTCTTAATCCTGAGTTCTAGTTTGAAAGCACTGTAGTCTGAGAGGCAGTTTGTTATAATTTCTGTTCT
TTTACATTTGCTGAGGAGTGCTTTACTTCCAACTATGTAGTCAATTTTTGGAATAAGTGTGATGTGGTGCCGAGAAGAATG
TATATTCTGTTGATTGGAGTGGAGAGTTCTGTAGATGTCTATTAGGTCCCGCTTGGTGCAGAGCTGAGTTCAATTTCTGGA
TATCTTTGTTAATTTCTGTCTTGTTGATCTGTCTAATTGACCGTGGGGTGATAAAGTCTCCCATTATTATTGTGTGGGA
GTCTAAGTCTCTTTGTAGGTCTCTAAGGACTTGCTTTGTGAATCTGGTGCTCCTGTATTAGGTGCATATATTTTAGGATAG
TTAGCTCTTCTTGTTGAATTGATCCCTTTATCATTATGTAATGGCCTCTTTGTCTCTTTGATCTTTGTTGGTTTAAAGTCT
GTTTATCAGAGACTAGGATTGCAACTCCTGCTTTTTTTGCTTTCCATTCCTTGGTAGATCTCCTCCATCCCTTTATTTT
GAGCCTATGTGCGTCTCTGCACATGAGATGGGTCTGCTGAATACAGCACACTGATGGGTCTGACTCTTTATCCAATTTGC
CAGTCCATGTCTTTTAACTGGAGCATTTAGCCCATTTACATTTAAGGTTAATATTGTTGTGAATTGATCCTGTCATT
ATGATGTTAGCTGGTTATTTTGCTCGTTAGTTGATGCAGTTTCTTCCTAGCCTCAATGATCTTTACAATTTGGCATGTTTTTG
CAGTGGCTGGTACTGGTTGTTCCTTTCCATGTTTAGTGCTTCCTTCAGGAGCTCTTGTAAGGCAGGCCTGGTGGTGACAAA
ATCTCTCAGCATTTGCTTGTCTGTAAAGGATTTTATTTCTCCTTCACTTATGAAGCTTAGTTTGGCTGGATATGAAATTCTG
GGTTGAAAATTCTTTTCTTTAAGAATGTTGAAATATTGGCCCCCACTCTCTTCTGGCTTGTAGAGTTTCTGCCGAAAGATGCT
GTTAGTCTGATGGACTTCCCTTTGTGGTAACCTGCCCTTTCTCTCGCTGCACTTAATGTTTTTCCTTCATTTCAACTTT
GGTGAATCTGACAATTATGTGTCTTTGAGTTACTCTTCTTGAGGAGTATCTTTGCGGCATTCTCTGTATTTCCTGAATTTGA
ATGCTGGCCTGCCTCACTAGATTGGGGAAGTTCTCCTGGATAATATCCTGCAGAGCGTTTTCCAACTTGGTTCCATTCTCCC
CATCACTTTCAGGTACACCAATCAGATGTAGATTTGGTCTTTTCACATAGTCCCATATTTCTTGGAGGCTTGTTCATTTCT
TTTTACTCTTTTTTCTCTAAACTTCTCTTCTTGCTTCATTTCATTCATTTGATCTTCAATCCCTTCTTCCACTTGATTGAATC
AGCTACTGAAGCTTGTGCATGTGTGCACATAGTTCTCGTGCCATGTTTCAGCTCCATCAGGTCATTTAAGGTCTCTCTAT
GCTGTTTTTTCTAGTTAGCCATTCGTCTAATGTTTTTTCAAGGTTTTTAGCTTCTTTGCTAAAAGGTTCAAACATCCTCCTT
AGCTCGGAGGAGTTTGTTATTACTGATCATCTGAAGCCTTCTTCTCTCAACTTGTGAAAGTCATTCTCTGTCCAGCTTTGTT
CCATTGCTGGCGAGGAGCTGCATTCCTTTGGAGGAGAAGACGTGCTCTGATTTTTAGAATTTTCAGCTTCTCTGCTCTGGTT
TCTCCCCATCTTATTGGTTTTATCTACCTTTGGTCTTTGATGATGGTGACGTACAGATGGGGTTTTGGTGTGGATGTTCTTTC
TCTTTGTTAGTTTTCCTTCTAACAGTCAGGACCCTCAGCTGCAGGTTGTTGGGAGTTTGCTGGAGGTCCACTCCAGACCCTG
TTTGCTTGGGTATCACCAGCAGAGGCTGCAGAACAGCAAATATTGCAGAACGGCAAATGTTGCTCCCTGATTGTTCCTCTG
GAAGCTTCGTCTCAGAGGGGCACCTGGCCGTATGAGGTGTCAGTCGGCCCCTACTGGGAGGTGCCTCCCAGTTAGGCTAC
TCAGGGGTCAGGAACCCACTTGAAGAGGCAGACTGTCCATTCTCAGATATCATATTCCATGCTGGGAGGACCCCTACTCTT
TTCAAAGCTGTCAGACAGGGACATTTAAGTCTGCAGAAGTTTCTGCTGTCTTTTGTTCAGCTGTGCCCTGCCCCTAGAGGT
GGAGTCTACAGAGGGCAGGCAGGCCTCCTTGAGCTGCGGTGGGCTCCACCCATTTCGAGCTTCCTGGCTGCTTTGTTTACCT
ACTCAAGTCTCAGCAATGGTGGACACCCCTCCCCCACCTCGCTGCTGCTTTGCAGTTCGATCTCAGACTGCTGTGCTAGC
AGTGAGCCAGGCTCCGTGGGCATGGGACCCTCCGAGCCAGGCCTGGGACATAATCTCCTGGTGTGCCGTTTGCTAAGACC
ATTGGAAAAGCACAGTATTAGGGTGGGGAGTGTCCTGATTTTCCAGGTACCGTCAGTCATGGCTTCCCTTGGCTAGGAAA
GGGAATTCCCCAACCCCTTGTGCTTCCTGGGTGAGGTGATGCCCCACCCTGCTTTGGCTCATGCTCCGTGGGTTGTACCCA
```

FIG.2 (Continued)

```
CTGTCTGACAAGCCCCAGTGAGATGAACCCGGTACCTCAGTTGGAAATGCAGAAATCACCCGTCTTCTGCATCACTCACG
CTGGGGGCTGTAGACTGGAGCTGTTCATATTTGGCCATCTTGGAACCTCCCTTTCCAAGTTCTTTATTACAGAGTGGGTCA
CTGAAACTTCATGGAACAAATTGGAAATTATCTTCTTAATTAATGTCACTGTCTACCATGTATGGGAATTTGGTAAATATT
ATATGGTTTCAATAACATAGTAGATAGAACATTGTCAAATCTAAACTTCAGTGAATTGTAACAGATCCCACCTGAAATTCT
AAAGAAAACAGAATTCTAATTGAAGAGGTTAAACTTTTACAGGGAATGTCAACTGCCATTTGGGTCCTGTAAACAAAAAA
CTGTTTTTAAAAAAGTAAACTTTAAAAGTATTTCAGATGACCTCATTTGCTATCCCAAGTGGCTTGAGTATGCTTGATGCT
AAGACTTCTTTGTTACAGACTGGAGATGTGTGCTACTGGGGCAGTGTTGCTCTGTGACAAGGAGGCAGAGGATGAGGGCA
AGGTTCGATGTGACTGTGAATTCTGGGTGGCTCTGGCTATCGGGAGCCTTCATTGATTACAGCAAAACAGTTGCTTTCCTA
GGGCAATAGTGTCTCTGTCACCCAGGCTGGAGTTCAGTGGCATGATCAATCGCTCACTGTAGCCTCAACTTCTTAGACTCA
AGTAATCCTCCCACCTCAGCCTCCCAAGTAGCTGAAACTACAGGTGTGCACCACCACACCTAATTTTTTTAATTTTTAAGT
TTTTGTAGAGACATGGTCTCACTGTGTTGCCCAGGTTGATCTCGAATTCCTGGGCTCTAGTGATCCTCCCGCCTCGGCCTCC
CAAAGTGTTGGGATTACAAATGTGAGCCACTGCACCTGGCCCTTTGCAACCTTCTTGACAATGCATTCCTTTATTCCCTAA
CTGGAAGTAACTTCTTTCTCTTTATAAAATTGTATCTGTACCTTTTCTGGGTCATTTCTACCTTTATATTCTAGTTACGTATG
TCCTACCTCCCTCCTAGGGAGGGAGGTAAGTAAGACTGGAAAGTAGACTTCATGTGTGATGAATGAATGAACAAAAGGA
AGTCTAACATATGGATATAGTCAACTGGATGCAAATTAAAAATTTTTAAATATTGATTTGCAAGATTTCATTAAGGTCAAC
TCTTAATAGTTTGTATCATATATATGTTAGGAACCAAATATTAATAACTTCTTCAGCATTACCATTATCTTTATAGGACTGTCT
AAAATGAGCAGCCATATCTTTAAACTGTGTTTTCTCTGATTACACGCTCACAGGTAAAACCCAAAGGGGCTGGGAACAAA
CAAGACTTTTTTTTTTTTCTGTATGCCTGAATTATCTGTACTGTTGCTTGTTTTCCCACCTTTGGCCATAGAAACTTAGTTCT
AACATGCTACAATTTTTGCAGTTCTTTCTCTTAGAAAAAGACCACATTGTCTGAAATTTCATCCATTAAGTAATCAAGCCT
TAAAGTTGAAGGATCTTGGTCATGATTAATCTAGACCTACAAAGTAGTATCTTAATGGCACTCCTTTAGAAAGTTAGGTT
CCAGGACACACATAGCTGCAGTGTCCACATTTTGTAAGCTCCTTCGTTGTCACAGCCACTCTCTCTTCTCTGTGGCTGATATTC
TAAAACTGGCAACACATCCTGATGGTAAAAGCTTGGTTCACGGAGACAGGTGACCTACTAGCTTTATGGCATTTGACAGGT
TACCTAACCTCTCTGACGCATAATTGCCTCATCTATATAAATGGGGATAATAATACCCATCCTGTCTCCTTGTAAAAATCAA
ATTAGATGACGCCTGTGAATGTTCTATAGTCTCTTAGACAAATGTAAGTTATGACTACAGCAAGAGTAAAAGAGCATGTT
GTTATGGACATTCTTTCAGTGAAATGTCTAAGACTTGTGAGTCACACTTAAAGCTAAACTTGATATCTACTTCATTGATTTT
CTTTTTAGTTCTATGTACTATATTGAATTTCCTGACAGTGGGGCTATGAAAAGCCTTCCTAGCATTTATAGATGTGGTTGAA
TTAATGGCTGTAAGCCTTAAAGCAGAATTTAAGACGACATCAATGAATTTATTAAAGTATAATAATATATAATCTGCTTAGC
AATATTCACAGACCTCTTTATCTTATGTGTGATAAAGAGTCATCCGAAGGTTGAAAATGAAGAATTGTCCTGGAAGCTCTT
ACTTAATCTTTTATTATTTCCTAATACAGTATATAAAATTACTCATTGAAAGCTTAGCAGAATAAGAAACAAGAAGTTAAA
AGGCTGAAAACTACAAATTTTGCTATTATTATTGTTATTACTTCCCAAGTCTCTTATTGATCTGTTAGAAATAGAGCTACAC
AGGAAATTGTAGGACAGTTAGTATGTGGTAGTGTTATCTGCTTTTTAATTATTCAAGTAAGGTTTTATTCCATTAGGGAA
CTCAAGAAAGTTGGTCATAATTGCTATCTGTCAAATTCCTTAGACAGGGATCCGCAACACCCAGGCCATGGAT
TGTTACCAGTCCCTGGCCTGTTAGGAACCAGGCTGCACAGTAGGAAGTGAGCGGCGGGTGAGCAAACATTGCCATCTGAG
CTCTGTCTCCTTTCAGATCAGCAGCAGCATTAGATTCTCATAGAAGCATGAGCCCTGTTGTGAACTGCACATGCAAGGGAT
CTAGGTTGTGTGCTCCTTATGAGAATCCAATTCCTTATGATAATTTAACTGATGATCTAAGGTGGAACCATTTCATCCCAA
AACCATCCACCCTGCTACTCCCAGACCGTGGAAAAATTGTCTTCCACAAAACTGGTTCCTGCTGCCAAAAAGGTTGGGAC
CACTGCCTTAGAGTTTATAATTTGGGGTTAGCACAGCCTATATTTACCTGAGATTTCAATGGGTTCACTGATCTTTCCAA
ATGAAAAGGCTTCTTACGAAAATTATATCCAAACTGTCTTTTCTCTTAGTTTAATAAACCTATCAGTAAGTTTTTACTGAGT
ACTGCTATTACATTTTCTCTGTTAAGCATTATGGGGGCTCAGACATGATCCATTCCCTCAAAGAACTTACCTTTCAGCTGA
AGACTGACTAGAATGAGCAAATACGGTTAACAATTAACAAGTGAGTAGGCCAGCTCGGCCAACATGGTGAAACCCTGTCT
CTACTAAAAATACAAAAATTAGCCGGGCATGGTGGTGGGCGCCTGTAATCCCAGCTACCTCCTGCTGAGGCAGGAGAATT
GCTTGAACCCCAGGAGGTGGAGATTGCAGTGAGCCGAGATTGCACTCCAGCCTGGGCGACAGAGCAAGACTCT
GTCTTGGGCAAAAAAACAAAACAAAGTGAGAAGGGAATCAAGTACTACGTAAGATGTAATGTGGAATTTTAGGGAA
GGAAGGCAGTGTATGCTGGAGTAATTAGAGAAAGGGGCATGCATGATTTGATGCTTGAACTGGATCATGAAGGATAAGC
AAGATTTTGGCAGCAAGTGAGAGGGAGAGAGGGAGTTTGTCAGAGGAATGGAACAAGTCAGGAGGCAGTAATGTGTACGG
CACTCCAAGGACTCTGTCCTGATCGGAGCAGAAGTGATGAAGCATTGAGTAGTTTGAGAAAGTTAGCTAAGAAGGGTGA
GGGCAGATGTTGGAGAGAGTTGAGTATCAGAGAAGAACATTAGATTTGAGCAGATAGAACAAAAATGCCATTGCCAGT
TTTTGTGTAAGAGAATAGTATTAGGGTGGTTACCCAGGAAGTGGTCATCAGAGTTGAATGGACAGAAAGAGTGTCTGAT
ACAGCATCGGGACGTTGTGGTCACAAAATGAGGTGGTGAGGGCTGAGCCAAGATGGTGGCAGTGGGATGGATAAAAAGG
GATGGCCAGGACAAATATTTTAAAGGAAAAATTAACAGGACATCTTTACTGACTGGATTGGAAGGCTATGCAGGAAATAT
ATTGTCAAACTTGATTCCAGGATTTCTATCCTATGCCTGGGTTGCCCAAAATATCAGGGAACCATTGTTAGAAAAGGTAGG
AGATACCACTGTTCCAACAAAAAGTATTGAGTTTGGTGTTGCACCCACTTAACTTCAAGGCCTTACAAGTGAGTAGACAG
TTAGTTAGAATTGCAGAAGTGCCCACTCAGAGAGCAGGGCTTGCAATGTGGGGTTGGACTTTGTCACCATTGTGTTAATTCC
TAATTCTATGCAGATGCTCAGCTTGAGGAATACCCATGTTTGGGCTTCAGAATGAAAGCCAAGTAATATTTACTCAGATGC
CAATTTTCCCTCTGAAATATTTGCTCATGGAACTGAGAGAACAATATATAAAGCATTAATTATTTTTCTCATAAAGTTATT
AATAAAAGATAAGATCAGTGAAAGGCAGAGTAAACTAGAAGCCAAGTATAGAAAATGGTATCATTCAAAGACTCATTA
CTGTAGTGGTGAAAACAAAACAATTTTCCAACAGCTTAAGATGCCTCAGTATTTTGGACCATTTTAAGTAGTTAGTGTGG
GCACTTAGTAAATATGTATTAAACTATAGTTCATTAATTCTTTTTTTTTTTTTTGAGATGGAGTTTCACTCTGGTCACCCA
```

FIG.2 (Continued)

```
GGCTGCATTTTTGCTTTCTTAGTGATATATAAAATGTCGAGTTTCACAATGATGGTATCTTAGATTTGATTAAATATGGTAT
TAAAAAATAGCTGATCACAGAAAGTCTCTACCAGTGTGATGTAGATGGCTAAAGTATTCCACATTTGCAAACTTTTATTGA
CCTAAATAAGGAGGTGCCCCTTGGGTTGTTTTTATTTGGACTGGGAATATTAGGAGAAAGCTTTTTCATTCAGTGTGTAAGT
ACAATCTACCAGAAATAGAAACCCCCATGGACGATCTATTTCTTTGATGGTACAGGACTCAGAACATTCACAAAGATTTA
GTTGTTAGCGGAATAGACATCTGTATTTTATTCAAACCAATTTTCCCTTCCTAATCTGAGAACATTGTGCAATCTAAGCAG
TTCTAAGCATGTTTGCTATTCGTGCAAAGTGAGAGTAAATCTAAAAGAAATTTTTTGTGTGTTTAGGGATGGTAATAAAG
TCTCTTAGTGGTTGAAAATGTTATTTCTTACAAAAGTGGAGAACATTTGCTTTTCAATACCAGAGTTTTCAGCCATTTCTGC
ATTCTGACCTATTGACTGGAGGTAGGTTGCCTTTGAATTCAGTAAAACTTCATGGGCAGAAAACACAGTTCCTTTTCCTACT
TATTTGGATATCATGATGGCCATTGCATGTATGTGTCTTTTTGTAAGTCCATGCCTCAGAACTGAGAAGTAGGAATAAAAT
TAGGGTCAGGGCTGGGGATGCTACTCTTGCTGCTGAGAAACACAATGCTTCAGGTAAGTGATTCTGAAGTCCTTCACCAC
CTGACGGTAACCTTGGGTTGGTCCATAGGTATGTTTCATTTGCTTGTTCATCCATTTAATGGCTTCCTAGAGCATGCT
TGTAGATGTAGAGCCAAATTTAGAGTAGAGCAACCCTCTGGCAAACAGGAAGAGATTAATTTTGTGGTATGCTTTTAAGG
GACTTCCCAGGAAACTTCAAAAGCAGAAAAAGAAGCACTAGCTGCCTATTCCAAAATGTGTAAAACACCACTCAGCTTTT
TAAAAGTAGGATAAACTCAGAGCGCGCGCACACGCGCGCGCGCACACACACACACACACACAGAGAGAACATCTCTAGT
AAAAAGAAAAGTTGAGCTTTCTTAGCTAGATGTGTGTATTAGCCAGAAAAAGCCAAGGAGTGAAGGGTTTTAGAGAACT
GGAGGAGATAAAGTGGAGTCTGCATATGGGAGGCATTTGAAATGGACTTAAATGTCTTTTTAATGCTGACTTTTTCAGTTT
TCTCCTTACCAGACACATTGTTTTCATGACATTAGCCCCAGGCATAGACACATCATTAAAATGAACATGTCAAAAAATGAT
TTCTGTTTAGAAATAAGCAAAACATTTTCAGTTGTGACCACCCAGGTGTAGAATAAAGAACAGTGGAATTGGGAGCCCTG
AGTTCTAACATAAACTTTCTTCATGACATAAGGCAAGTCTTCTATGGCCTTTGGTTTCCTTACCTGTAAAACAGGATGGCT
CAATGAAATTATCTTTCTTCTTTGCTATAATAGAGTATCTCTGTGGGAAGAGGAAAAAAAAAGTCAATTTAAAGGCTCCTT
ATAGTTCCCCAACTGCTGTTTTATTGTGCTATTCATGCCTAGACATCACATAGCTAGAAAGGCCCCATCAGACCCCTCAGGC
CACTGCTGTTCCTGTCACACATTCCTGCAAAGGACCATGTTGCTAACTTGAAAAAAATTACTATTAATTACACTTGCAGTT
GTTGCTTAGTAACATTTATGATTTTGTGTTTCTCGTGACAGCATGGCAGAGATCATTAAAAATTAAACTTACAAAGCTGC
TAAAGTGGGAAGAAGGAGAACTTGAAGCCACAATTTTTGCACTTGCTTAGAAGCCATCTAATCTCAGGTTTATATGCTAG
ATCTTGGGGGAAACACTGCATGTCTCTGGTTTATATTAAACCACATACAGCACACTACTGACACTGATTGTGTCTGGTGC
AGCTGGAGTTTATCACCAAGACATAAAAAAACCTTGACCCTGCAGAATGGCCTGGAATTACAATCAGATGGGCCACATGG
CATCCCGGTGAAAGAAAGCCCTAACCAGTTTCTGTCTTGTTTCTGCTTTCTCCCTACAGTTCCACCAGGTGAGAAGAGTG
ATGACCATCCTTTTCCTTACTATGGTTATTTCATACTTTGGTTGACAAGGCTGCCCCCATGAAAGAAGCAAACATCCGA
GGACAAGGTGGCTTGGCCTACCCAGGTGTGCGGACCCATGGGACTCTGGAGAGCGTGAATGGGCCCAAGGCAGGTTCAA
GAGGCTTGACATCATTGGCTGACACTTTCGAACACGTGATAGAAGAGCTGTTGGATGAGGACCAGAAAGTTCGGCCCAAT
GAAGAAAACAATAAGGACGCAGACTTGTACACGTCCAGGGTGATGCTCAGTAGTCAAGTGCCTTTGGAGCCTCCTCTTCT
CTTTCTGCTGGAGGAATACAAAAATTACCTAGATGCTGCAAACATGTCCATGAGGGTCCGGCGCCACTCTGACCCTGCCC
GCCGAGGGGGAGCTGAGCGTGTGTGACAGTATTAGTGGGGTAACGGCAGCAGACAAAAAAGACTGCAGTGGACATGTC
GGGCGGGACGGTCACAGTCCTTGAAAAGGTCCCTGTATCAAAAGGCCAACTGAAGCAATACTTCTACGAGACCAAGTGC
AATCCCATGGGTTACACAAAAGAAGGCTGCAGGGGCATAGACAAAAGGCATTGGAACTCCCAGTGCCGAACTACCCAGT
CGTACGTGCGGGCCCTTACCATGGATAGCAAAAAGAGAATTGGCTGGCGATTCATAAGGATAGACACTTCTGTGTATGT
ACATTGACCATTAAAAGGGGAAGATAGTGGATTTATGTTGTATAGATTAGATTATATTGAGACAAAAATTATCTATTTGTA
TATATACATAACAGGGTAAATTATTCAGTTAAGAAAAAATATTTATGAACTGCATGTATAAATGAAGTTTATACAGT
ACAGTGGTTCTACAATCTATTTATTGGACATGTCCATGACCAGAAGGGAAACAGTCATTTGCGCACAACTTAAAAAGTCT
GCATTACATTCCTTGATAATGTTGTGGTTTGTTGCCGTTGCCAAGAACTGAAAACATAAAAAGTTAAAAAAAAATAATAAA
TTGCATGCTGCTTTAATTGTGAATTGATAATAAACTGTCCTCTTTCAGAAAACAGAAAAAAAACACACACACACAACA
AAAATTTGAACCAAAACATTCCGTTTACATTTAGACAGTAAGTATCTTCGTTCTTGTTAGTACTATATCTGTTTACTGCT
TTTAACTTCTGATAGCGTTGGAATTAAAAACAATGTCAAGGTGCTGTTGTCATTGCTTTACTGGCTTAGGGGATGGGGATG
GGGGGTATATTTTGTTTGTTTGTGTTTTTTTTCGTTTGTTTGTTTGTTTTTAGTTCCCACAGGGAGTAGAGATGGGGA
AAGAATTCCTACAATATATATTCTGGCTGATAAAAGATACATTTGTATGTTGTGAAGATGTTGCAATATCGATCAGATGA
CTAGAAAGTGAATAAAAATTAAGGCAACTGAACAAAAAAATGCTCACACTCCACATCCCGTGATGCACCTCCCAGGCCCC
GCTCATTCTTTGGGCGTTGGTCAGAGTAAGCTGCTTTGACGGAAGGACCTATGTTGCTCAGAACACATTCTTTCCCCCC
CTCCCCCTCTGGTCTCCTCTTTGTTTTGTTTTAAGGAAGAAAAATCAGTTGCGCGTTCTGAAATATTTACCACTGCTGTGA
ACAAGTGACACATTGTGTCACATCATGACACTCGTATAAGCATGGAGAACAGTGATTTTTTTTAGAACAGAAAACAAC
AAAAAATAACCCCAAAATGAAGATTATTTTTTATGAGGAGTGAACATTTGGGTAAATCATGGCTAAGCTTAAAAAAAACT
CATGGTGAGGCTTAACAATGTCTTGTAAGCAAAAGGTAGAGCCCTGTATCAACCCAGAAACACCTAGATCAGAACAGGA
ATCCACATTGCCAGTGACATGAGACTGAACAGCCAAATGGAGGCTATGTGGAGTTGGCATTGCATTTACCGGCAGTGCGG
GAGGAATTTCTGAGTGGCCATCCCAAGGTCTAGGTGGAGGTGGGGCATGGTATTTGAGACATTCCAAAACGAAGGCCTCT
GAAGGACCCTTCAGACGTGGCTCTGGAATGACATGTGTCAAGCTGCTTGGACCTCGTGCTTTAAGTGCCTACATTATCTAA
CTGTGCTCAAGAGGTTCTCGACTGGAGGACCACACTCAAGCCGACTTATGCCCACCATCCCACCTCTGGATAATTTTGCAT
AAAATTGGATTAGCCTGGAGCAGGTTGGGAGCCAAATGTGGCATTTGTGATCATGAGATTGATGCAATGAGATAGAAGAT
GTTTGCTACCTGAACACTTATTGCTTTGAAACTAGACTTGAGGAAACCAGGGTTTATCTTTTGAGAACTTTTGGTAAGGGA
AAAGGGGAACAGGAAAAGAAACCCCAAACTCAGGCCGAATGATCAAGGGGACCCATAGGAAATCTTGTCCAGAGACAAG
```

FIG.2 (Continued)

```
ACTTCGGGAAGGTGTCTGGACATTCAGAACACCAAGACTTGAAGGTGCCTTGCTCAATGGAAGAGGCCAGGACAGAGCT
GACAAAATTTTGCTCCCCAGTGAAGGCCACAGCAACCTTCTGCCCATCCTGTCTGTTCATGGAGAGGGTCCCTGCCTCACC
TCTGCCATTTTGGGTTAGGAGAAGTCAAGTTGGGAGCCTGAAATAGTGGTTCTTGGAAAAATGGATCCCCAGTGAAAACT
AGAGCTCTAAGCCCATTCAGCCCATTTCACACCTGAAAATGTTAGTGATCACCACTTGGACCAGCATCCTTAAGTATCAGA
AAGCCCCAAGCAATTGCTGCATCTTAGTAGGGTGAGGGATAAGCAAAAGAGGATGTTCACCATAACCCAGGAATGAAGA
TACCATCAGCAAAGAATTTCAATTTGTTCAGTCTTTCATTTAGAGCTAGTCTTTCACAGTACCATCTGAATACCTCTTTGAA
AGAAGGAAGACTTTACGTAGTGTAGATTTGTTTTGTGTTGTTTGAAAATATTATCTTTGTAATTATTTTAATATGTAAGGA
ATGCTTGGAATATCTGCTGTATGTCAACTTTATGCAGCTTCCTTTTGAGGGACAAATTTAAAACAAACAACCCCCCATCAC
AAACTTAAAGGATTGCAAGGGCCAGATCTGTTAAGTGGTTTCATAGGAGACACATCCAGCAATTGTGTGGTCAGTGGCTC
TTTTACCCAATAAGATACATCACAGTCACATGCTTGATGGTTATGTTGACCTAAGATTTATTTTGTTAAAATCTCTCTCTG
TTGTGTTCGTTCTTGTTCTGTTTGTTTTGTTTTTAAAGTCTTGCTGTGGTCTCTTTGTGGCAGAAGTGTTTCATGCATGGC
AGCAGGCCTGTTGCTTTTTATGGCGATTCCCATTGAAAATGTAAGTAAATGTCTGTGGCCTTGTCTCTCTATGGTAAAG
ATATTATTCACCATGTAAAACAAAAAACAATATTTATTGTATTTAGTATATTTATATAATTATGTTATTGAAAAAAATTG
GCATTAAAACTTAACCGCATCAGAAGCCTATTGTAAATACAAGTTCTATTTAAGTGTACTAATTAACATATAATATATGTT
TTAAATATAGAATTTTTAATGTTTTTAAATATATTTCAAAGTACATAA
```

FIG.3

Natural antisense sequence (NR_002832.1): SEQ ID NO: 2

>gi |84872122 | ref | NR_002832.1| Homo sapiens BDNF opposite strand (non-protein coding) (BDNFOS ), non-coding RNA

```
CNGCNNAAAGATTTCTTCACAGGGTCCTTTAAACTGTCNNTTTNTAAGAGGTCCTTCCACTACAGGTAAAGGGAAATTCCC
TCTACCCTAGGGCCCCTCAGGANCCCTTCCTCTCTCACACGTTTCTTCGACTGCTNNNGATTTAAGCATTCAGCTGGCCAC
GCAACGCAAGAAGCAATAAGAACACAAAAACCCTACCCTGTTCNTCCTCTATCCGTGGCCTTTGCCACCACCTCCACAAC
CTAGTTCAGATTCCCTCTTCTTTTCTCAAGGGAACGTCTAAAGCTCTCAAGTCCGTTTGGCAGGGCGATTTTGTAAGTCTGA
ANCATTCAGTGTGTCTCTCGATCTCAGGCAGCTCAAAAGAAAAGATCTGCTGGCTGCGTGAAGGTGCATTAGAAACCTG
CTGCTACCTTGCAGCCTGGGCTGAGCATATGCTCCGGAACTTGCTTCTCTCCAACATCCTGCACCTCAGGGTTGCACGCT
CTGGTTCCCAAGCCCCCGGCCGCTGGCTTATGCAAATCACTTAGGTACATGCAAAAGTATCCCTTCTCCCGGAGCGCCATT
GGGCCGGGGAGGTCTCGAGGTCTCATTACTATGCAGAGAGGAGAGCCCCCATTGGCCAAGAGGAGGAGCCAGAGGGGCGTGT
TTCTCGGGCAAATTGGATCTCCTAAAATTGGATGACCTGGGCTGAAAGACAACTTAAAGACCCCCAGAAAACTCTGGTTTT
ATAGATAAGAAATCTGAGGCTCGAGAGAGAGTGTGTTCTGCCCAACATCATCACGGAACAGCTCCTGGGCTCCTGGCTCC
TAATCTGTCATCGCTGTCTGGAACAGCGATGACTCGATCGCGAGATCAGGAAGGTGGCCGAGTGTGTCGCCGCGGCCATC
AGGCACTTCTCCTTCCTGCCCTTGTATGAAGAAGGATGTGTTTGCTTCCCCTTGTGCCATGATTGTAAATTTCCTGAGGCCT
CCTCAGCCCTGCAGAACTGGGGTTATAGCCATGTGACTGATCTTCGTCCAAGAATATGTAAAGAAAAAGTGTTGAGTGG
CTTTTAGGGCTAGAGCAATGTATCTTAGGCTCACTTAAGGAAGCTGTAGAGATGAGCCCAAGGAGGGAAACCAGAAGAG
CCCCCCAGGCTCACCAGTTGTTTGTTGGCTCCCTACAAACATGTCATTCAAGTGGCTAATCTTACAACAGCACAAATTCAT
CTAACCAGAAAGAGAAGAGGAGGCTCCAAAGCACTTGACTACTGAGCATCACCCTGGACGTGTACAAGTCTGCGTCCTT
ATTGTTTTCTTCATTGGGCCGAACTTTCTGGTCCTCATCCAACAGCTCTTCTATCACGTGTTCGAAAGTGTCAGCCAATGAT
GTCAAGCATCTTGAACCTGCCTTGGGCCCATTCACGCTCTCCACATGGGTCCCGCACACCTGGAGATACTCTATTA
TAGCAAAGAAGAAAGATAAATTTCATTGAGCCATCCTGTTTTACAGTATTGAATTATTACCACAAGGTACCAACCATATATG
CATACTTAATAGGGTATTTTGTCAAAACTATGCATGAAGGTCATTGTTTGAGATGTCAGAACATTTTCCCGTGAGAAGAT
CTCATTGGGCATTGAAACAGAACCACATGCTCTTCAGACCAGCAACCGCGACTACCAAATACTCCTCTGTCAACTCTACTT
GAGTAAGAACGCTTTCAATTAAGGCCTAAGTGTCAACATGCCTTTAAAAAAAATCGTGGTGACACAAAATCTTTCTTTTA
GCACCCAACAGAATCCCTTCAAAGCCTCGTGGTCTGACACCCTATGCTACGTGACTTGTGACCCATCCATTTGTCATGTTC
TTCGGGAATGTGGCTAAGGTGGCTAAGATGTGACTTGAAAAGAAAGGTAGAACAAGATCATCTCAAATTTATTATCAAGGA
ATAGTTCAGAAAACGACTTCAGACCACAGAGACAGCAGAACAGATGGTCCGGCATGGATAGAGCATCAGACACTCACAG
ACTGTGCCAACAAGAGCCATCGAGTCAAAACAGCCAAAGGAAGGAGGGTCATGGAATGGGTTCTCTCACACCAAACTGA
TGCCCAGAGGCCCTCAGCATGAATAACAAAGGCAACCAGACCCACAAGCCATACTGAGTGGATACAAAACCTATACCTA
```

FIG.3 (Continued)

```
GGCTGACATCCCAAATGTGTGTGGCAAGTTAGATGATGATGGCACAAAAGACAGAACACCTTGCTTCTGGCCATTGTCAG
CTCTTGGAAGAGAGCACACTTTTAGAGGAGCAGCTGCAAGGAGCCTGAGAACAAAACTGGAAATGTCTGTTATGAAAGC
CTTCACAGGAAATTCTGCAAGTGGCAACGTGGGTCCATTCCGTGTGTGTCACTAGAGCTGGCGCAAGCCCATGGCCATGG
TGAGGCAGCGTTTCCACTGGAACTAATCTGATACCTGCACCAACTCTTGCAACTGTGCAGTGTTCCCACTGCAAACTACGG
ATGGGGTAAAAGACTGCTCACCTCCTATTTCTCATCTAATCTCACACACTCTGTTTGATGAGGCTATGGAGAAACAGGTCT
TCTCATACACTAAAGGTGGGAGTACAAACAATTCAAGCCCTGTGCAGGACAATTAGGCAATACCTATCAAAATTATACAT
GATTTTTCCTGCTGACCCAGCAATTCCACTTTTGGGAATAATTGACAGATATAGGTGCATATGTACAAAATGATGGAAAGC
TCTCTGGTATATATTAGTAAGTGATAAAACAAGGTGTGTGTATATATGGCTACTACCTTTTGTTTTAAAAATGGGGGAAAA
TGGTGGAGCTTGCGGTGAGCCGAGATCGTGCCACTGCACTCCAGCCTGGGCGACAGAGCGAGACTCCGTCTCAAAAAAA
AAACAGGGTGGGGTGGGGGGGAAATAATAGTACATACTCATATTTACCTGTATCTATATAAAACACACTATCAAGGATTC
ACAAGAAACTAATACAAATGATCCCCTTATAGATGGTATGTATTGGGGGATACTGAGGTGAGCAGGGTATAAGTGGGGC
AAGACTTTTCAGTGTAAACTTCTTTTAAATTTTATTTTGATTTTGAATAATGTAAATTAACTGTCAAATAATTAAATTAAA
AATAACCAATTTATTAACAAAAAAAAAAAAAAAAAAAATA
```

FIG.4

| Sequence ID | Sequence |
| --- | --- |
| SEQ ID NO :3 | CTTGAATTGT TTGTA |
| SEQ ID NO :4 | AGTTGCAAGA GTTGG |
| SEQ ID NO :5 | ATCTGTTCTG CTGTC |
| SEQ ID NO :6 | CATATTCTTG GACGA |
| SEQ ID NO :7 | TGTGCTGTTG TAAGA |
| SEQ ID NO :8 | TGACAGAGGA GTATT |

FIG.5

| Sequence ID | Sequence |
| --- | --- |
| SEQ ID NO :9 | GCACACCTGG AGATACTCTA TTATA |
| SEQ ID NO :10 | CCTGCAGAAT GGCCTGGAAT TACAA |

SEQUENCE LISTING

<160> NUMBER OF SEQ ID NOS: 11

<210> SEQ ID NO 1
<211> LENGTH: 4755
<212> TYPE: DNA
<213> ORGANISM: Homo sapiens
<300> PUBLICATION INFORMATION:
<308> DATABASE ACCESSION NUMBER: NM_170735
<309> DATABASE ENTRY DATE: 2010-07-18
<313> RELEVANT RESIDUES IN SEQ ID NO: (1)..(4755)

<400> SEQUENCE: 1

```
cacacacaca cacacacaca gagagaacat ctctagtaaa aagaaaagtt gagctttctt      60
agctagatgt gtgtattagc cagaaaaagc caaggagtga agggttttag agaactggag     120
gagataaagt ggagtctgca tatgggaggc atttgaaatg gacttaaatg tcttttaat     180 gctgactttt tcagttttct ccttaccaga cacattgttt tcatgacatt agccccaggc     240
atagacacat cattaaaatg aacatgtcaa aaaatgattt ctgtttagaa ataagcaaaa     300
cattttcagt tgtgaccacc caggtgtaga ataaagaaca gtggaattgg gagccctgag     360
ttctaacata aactttcttc atgacataag gcaagtcttc tatggccttt ggtttcctta     420
cctgtaaaac aggatggctc aatgaaatta tctttcttct ttgctataat agagtatctc     480
tgtgggaaga ggaaaaaaaa agtcaattta aaggctcctt atagttcccc aactgctgtt     540
ttattgtgct attcatgcct agacatcaca tagctagaaa ggcccatcag acccctcagg     600
ccactgctgt tcctgtcaca cattcctgca aaggaccatg ttgctaactt gaaaaaaatt     660
actattaatt acacttgcag ttgttgctta gtaacattta tgattttgtg tttctcgtga     720
cagcatgagc agagatcatt aaaaattaaa cttacaaagc tgctaaagtg ggaagaagga     780
```

```
gaacttgaag ccacaatttt tgcacttgct tagaagccat ctaatctcag gttatatgct      840
agatcttggg ggcaaacact gcatgtctct ggtttatatt aaaccacata cagcacacta      900
ctgacactga tttgtgtctg gtgcagctgg agtttatcac caagacataa aaaaaccttg      960
accctgcaga atggcctgga attacaatca gatgggccac atggcatccc ggtgaaagaa     1020
agccctaacc agttttctgt cttgtttctg cttttctccct acagttccac caggtgagaa    1080
gagtgatgac catccttttc cttactatgg ttatttcata ctttggttgc atgaaggctg     1140
cccccatgaa agaagcaaac atccgaggac aaggtggctt ggcctaccca ggtgtgcgga     1200
cccatgggac tctggagagc gtgaatgggc ccaaggcagg ttcaagaggc ttgacatcat     1260
tggctgacac tttcgaacac gtgatagaag agctgttgga tgaggaccag aaagttcggc     1320
ccaatgaaga aaacaataag gacgcagact tgtacacgtc cagggtgatg ctcagtagtc     1380
aagtgccttt ggagcctcct cttctctttc tgctggagga atacaaaaat tacctagatg     1440
ctgcaaacat gtccatgagg gtccggcgcc actctgaccc tgcccgccga ggggagctga     1500
gcgtgtgtga cagtattagt gagtgggtaa cggcggcaga caaaaagact gcagtggaca     1560
tgtcgggcgg gacggtcaca gtccttgaaa aggtccctgt atcaaaaggc caactgaagc     1620
aatacttcta cgagaccaag tgcaatccca tgggttacac aaaagaaggc tgcaggggca     1680
tagacaaaag gcattggaac tcccagtgcc gaactaccca gtcgtacgtg cgggccctta     1740
ccatggatag caaaaagaga attggctggc gattcataag gatagacact tcttgtgtat     1800
gtacattgac cattaaaagg ggaagatagt ggatttatgt tgtatagatt agattatatt     1860
gagacaaaaa ttatctattt gtatatatac ataacagggt aaattattca gttaagaaaa     1920
aaataatttt atgaactgca tgtataaatg aagtttatac agtacagtgg ttctacaatc     1980
tatttattgg acatgtccat gaccagaagg gaaacagtca tttgcgcaca acttaaaaag     2040
tctgcattac attccttgat aatgttgtgg tttgttgccg ttgccaagaa ctgaaaacat     2100
aaaaagttaa aaaaaataat aaattgcatg ctgctttaat tgtgaattga taataaactg     2160
tcctctttca gaaacagaa aaaacacac acacacacaa caaaaatttg aaccaaaaca       2220
ttccgtttac attttagaca gtaagtatct tcgttcttgt tagtactata tctgtttttac    2280 tgcttttaac ttctgatagc gttggaatta aaacaatgtc aaggtgctgt tgtcattgct     2340
ttactggctt aggggatggg ggatgggggg tatattttg tttgtttgt gttttttttt       2400 cgtttgtttg ttttgttttt tagttcccac agggagtaga gatggggaaa gaattcctac     2460
aatatatatt ctggctgata aaagatacat ttgtatgttg tgaagatgtt tgcaatatcg     2520
atcagatgac tagaaagtga ataaaaatta aggcaactga acaaaaaaat gctcacactc     2580
cacatcccgt gatgcacctc ccaggcccg ctcattcttt gggcgttggt cagagtaagc      2640
tgcttttgac ggaaggacct atgtttgctc agaacacatt ctttcccccc ctcccctct      2700 ggtctccctct ttgttttgtt ttaaggaaga aaaatcagtt gcgcgttctg aaatatttta    2760
ccactgctgt gaacaagtga acacattgtg tcacatcatg acactcgtat aagcatggag     2820
aacagtgatt ttttttaga acagaaaaca acaaaaaata accccaaaat gaagattatt      2880
ttttatgagg agtgaacatt tgggtaaatc atggctaagc ttaaaaaaaa ctcatggtga     2940
ggcttaacaa tgtcttgtaa gcaaaggta gagccctgta tcaacccaga aacacctaga     3000
tcagaacagg aatccacatt gccagtgaca tgagactgaa cagccaaatg gaggctatgt     3060
ggagttggca ttgcatttac cggcagtgcg ggaggaattt ctgagtggcc atcccaaggt    3120
ctaggtggag gtggggcatg gtatttgaga cattccaaaa cgaaggcctc tgaaggaccc     3180
```

-continued

```
ttcagaggtg gctctggaat gacatgtgtc aagctgcttg gacctcgtgc tttaagtgcc    3240
tacattatct aactgtgctc aagaggttct cgactggagg accacactca agccgactta    3300
tgcccaccat cccacctctg gataattttg cataaaattg gattagcctg gagcaggttg    3360
ggagccaaat gtggcatttg tgatcatgag attgatgcaa tgagatagaa gatgtttgct    3420
acctgaacac ttattgcttt gaaactagac ttgaggaaac cagggtttat cttttgagaa    3480
cttttggtaa gggaaaaggg aacaggaaaa gaaaccccaa actcaggccg aatgatcaag    3540
gggacccata ggaaatcttg tccagagaca agacttcggg aaggtgtctg gacattcaga    3600
acaccaagac ttgaaggtgc cttgctcaat ggaagaggcc aggacagagc tgacaaaatt    3660
ttgctcccca gtgaaggcca cagcaacctt ctgcccatcc tgtctgttca tggagagggt    3720
ccctgcctca cctctgccat tttgggttag gagaagtcaa gttgggagcc tgaaatagtg    3780
gttcttggaa aaatggatcc ccagtgaaaa ctagagctct aagcccattc agcccatttc    3840
acacctgaaa atgttagtga tcaccacttg gaccagcatc cttaagtatc agaaagcccc    3900
aagcaattgc tgcatcttag tagggtgagg gataagcaaa agaggatgtt caccataacc    3960
caggaatgaa gataccatca gcaaagaatt tcaatttgtt cagtctttca tttagagcta    4020
gtctttcaca gtaccatctg aatacctctt tgaaagaagg aagactttac gtagtgtaga    4080
tttgttttgt gttgtttgaa atattatct ttgtaattat ttttaatatg taaggaatgc    4140
ttggaatatc tgctatatgt caactttatg cagcttcctt ttgagggaca aatttaaaac    4200
aaacaacccc ccatcacaaa cttaaaggat tgcaagggcc agatctgtta agtggtttca    4260
taggagacac atccagcaat tgtgtggtca gtggctcttt tacccaataa gatacatcac    4320
agtcacatgc ttgatggttt atgttgacct aagatttatt ttgttaaaat ctctctctgt    4380
tgtgttcgtt cttgttctgt tttgttttgt tttttaaagt cttgctgtgg tctctttgtg    4440
gcagaagtgt ttcatgcatg gcagcaggcc tgttgctttt ttatggcgat tcccattgaa    4500
aatgtaagta aatgtctgtg gccttgttct ctctatggta aagatattat tcaccatgta    4560
aaacaaaaaa caatatttat tgtatttag tatatttata taattatgtt attgaaaaaa    4620
attggcatta aaacttaacc gcatcagaac ctattgtaaa tacaagttct atttaagtgt    4680
actaattaac atataatata tgttttaaat atagaatttt taatgttttt aaatatattt    4740
tcaaagtaca taaaa                                                      4755
```

```
<210> SEQ ID NO 2
<211> LENGTH: 3175
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (104)..(104)
```

<223> OTHER INFORMATION: n is a, c, g, or t
<220> FEATURE:
<221> NAME/KEY: misc_feature
<222> LOCATION: (137)..(139)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t

<400> SEQUENCE: 2

| | | | | | |
|---|---|---|---|---|---|
| cngcnnaaag | atttcttcac | agggtccttt | aaactgtcnn | tttntaagag | gtccttccac | 60 |
| tacaggtaaa | gggaaattcc | ctctacccta | gggcccctca | ggaccccttc | ctctctcaca | 120 |
| cgtttcttcg | actgctnnng | atttaagcat | tcagctggcc | acgcaacgca | agaagcaata | 180 |
| agaacacaaa | aacccatccc | tgttcntcct | ctatccgtgg | cctttgccac | cacctccaca | 240 |
| acctagttca | gattcctctt | cttttctcaa | gggaacgtct | aaagctctca | agtccgtttt | 300 |
| ggcagggcga | ttttgtaagt | ctgaancatt | tcagtgtgtc | tctcgatctc | aggcagctca | 360 |
| aaagaaaaga | tctgctggct | gcgtgaaggt | gcattagaaa | cctgctgcta | ccttgcagcc | 420 |
| tgggctgagc | atatgctccg | gaacttgctt | ctcttccaac | atcctgcacc | tcagggttgc | 480 |
| acgctctggt | tcccaagccc | ccggccgctg | gcttatgcaa | atcacttagg | tacatgcaaa | 540 |
| agtatccctt | ctcccggagc | gccattggcc | cggggaggtc | tcgagctcat | tactatgcag | 600 |
| agaggagagc | cgccattggc | caagaggagg | accagagggg | cgtgtttctc | gggcaaattg | 660 |
| gatctcctaa | attggatgac | ctgggctgaa | agacaactta | agacccccca | gaaaactctg | 720 |
| gttttataga | taagaaatct | gaggctcgag | agagagtgtg | ttctgcccaa | catcatcacg | 780 |
| gaacagctcc | tgggctcctg | gctcctaatc | tgtcatcgct | gtctggaaca | gcgatgactc | 840 |
| gatcgcgaga | tcaggaaggt | ggccgagtgt | gtcgccgcgg | ccatcaggca | cttctccttc | 900 |
| ctgcccttgt | atgaagaagg | atgtgttgc | ttccccttgt | gccatgattg | taaatttcct | 960 |
| gaggcctcct | cagccctgca | gaactgggt | tatagccatg | tgactgatct | tcgtccaaga | 1020 |
| atatgtaaag | aaaaagtgtt | gagttggctt | ttagggctag | agcaatgtat | cttaggctca | 1080 |
| cttaaggaag | ctgtagagat | gagcccaagg | agggaaacca | gaagagcccc | ccaggctcac | 1140 |
| cagttgtttg | ttggctccct | acaaacatgt | cattcaagtg | gctaatctta | caacagcaca | 1200 |
| aattcatcta | accagaaaga | gaagaggagg | ctccaaaggc | acttgactac | tgagcatcac | 1260 |
| cctggacgtg | tacaagtctg | cgtccttatt | gtttctttca | ttgggccgaa | ctttctggtc | 1320 |
| ctcatccaac | agctcttcta | tcacgtgttc | gaaagtgtca | gccaatgatg | tcaagcatct | 1380 |
| tgaacctgcc | ttgggcccat | tcacgctctc | cagagtccca | tgggtccgca | cacctggaga | 1440 |
| tactctatta | tagcaaagaa | gaaagataat | ttcattgagc | catcctgttt | tacagtattg | 1500 |
| aattattacc | acaaggtacc | aaccatatat | gcatacttaa | tagggtattt | tgtcaaaact | 1560 |
| atgcatgaag | gtcatttgtt | tgagatgtca | gaacattttc | ccgtgagaag | atctcattgg | 1620 |
| gcattgaaac | agaaccacat | gctcttcaga | ccagcaaccg | cgactaccaa | atactcctct | 1680 |
| gtcaactcta | cttgagtaag | aacgctttca | attaaggcct | aagtgtcaac | atgcctttaa | 1740 |
| aaaaaatcgt | ggtgacacaa | aatctttctt | tttagcaccc | aacagaatcc | cttcaaagcc | 1800 |
| tcgtggtctg | acaccctatg | ctacgtgact | tgtgacccat | ccatttgtca | tgttcttcgg | 1860 |
| gaatgtggct | aaggggctaa | gatgtgactt | gaaaagaaag | gtagaacaag | atcatctcaa | 1920 |

```
atttattatc aaggaatagt tcagaaaacg acttcagacc acagagacag cagaacagat   1980
ggtccggcat ggatagagca tcagacactc acagactgtg ccaacaagag ccatcgagtc   2040
aaaacagcca aaggaaggag ggtcatggaa tgggttctct cacaccaaac tgatgcccag   2100
aggccctcag catgaataac aaaggcaacc agacccacaa gccatactga gtggatacaa   2160
aacctatacc taggctgaca tcccaaatgt gtgtggcaag ttagatgatg atggcacaaa   2220
agacagaaca ccttgcttct ggccattgtc agctcttgga agagagcaca cttttagagg   2280
agcagctgca aggagcctga gaacaaaact ggaaatgtct gttatgaaag ccttcacagg   2340
aaattctgca agtggcaacg tgggtccatt ccgtgtgtgt cactagagct ggcgcaagcc   2400
catggccatg gtgaggcagc gtttccactg gaactaatct gatacctgca ccaactcttg   2460
caactgtgca gtgttcccac tgcaaaactac ggatggggta aaagactgct cacctcctat   2520
ttctcatcta atctcacaca ctctgtttga tgaggctatg gagaaacagg tcttctcata   2580
cactaaaggt gggagtacaa acaattcaag ccctgtgcag gacaattagg caatacctat   2640
caaaattata catgattttt cctgctgacc cagcaattcc acttttggga ataattgaca   2700
gatataggtg catatgtaca aaatgatgga aagctctctg gtatatatta gtaagtgata   2760
aaacaaggtg tgtgtatata tggctactac cttttgtttt aaaaatgggg gaaaatggtg   2820
gagcttgcgg tgagccgaga tcgtgccact gcactccagc ctgggcgaca gagcgagact   2880
ccgtctcaaa aaaaaacag ggtggggtgg ggggaaata atagtacata ctcatattta   2940
cctgtatcta tataaaacac actatcaagg attcacaaga aactaataca aatgatcccc   3000
ttatagatgg tatgtattgg gggatactga ggtgagcagg gtataagtgg ggcaagactt   3060
ttcagtgtaa acttctttta aattttattt tgattttga ataatgtaaa ttaactgtca   3120
aataattaaa ttaaaaataa ccaatttatt aacaaaaaaa aaaaaaaaa aaata         3175
```

```
<210> SEQ ID NO 3
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 3
cttgaattgt ttgta                                                       15

<210> SEQ ID NO 4
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 4
agttgcaaga gttgg                                                       15

<210> SEQ ID NO 5
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 5
atctgttctg ctgtc                                                       15
```

```
<210> SEQ ID NO 6
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 6
catattcttg gacga                                                        15

<210> SEQ ID NO 7
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 7
tgtgctgttg taaga                                                        15

<210> SEQ ID NO 8
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 8
tgacagagga gtatt                                                        15

<210> SEQ ID NO 9
<211> LENGTH: 25
<212> TYPE: DNA
<213> ORGANISM: Artificial Sequence
<220> FEATURE:
<223> OTHER INFORMATION: Assay sequence

<400> SEQUENCE: 9
gcacacctgg agatactcta ttata                                             25

<210> SEQ ID NO 10
<211> LENGTH: 25
<212> TYPE: DNA
<213> ORGANISM: Artificial Sequence
<220> FEATURE:
<223> OTHER INFORMATION: Assay Sequence

<400> SEQUENCE: 10
cctgcagaat ggcctggaat tacaa                                             25

<210> SEQ ID NO 11
<211> LENGTH: 46159
<212> TYPE: DNA
<213> ORGANISM: Homo sapiens

<400> SEQUENCE: 11
gtaaaccaat agcccccatg ctctgtgcga tttcattgtg tgctcgcgtt cgcaagctcc       60
gtagtgcagg aaggtgcggg aaggtgtgtc tgtggcccgg gaaacgcacg ccctctccca      120
gagaacttgg gtgctgggat ggggaggaag gggagagttg aaagctaggg gagcgagacc      180
tcggggcgtg cgattctcac tcgctccctc ccgccccagc gcccacagcc ggggtttctg      240
cagagggcgc gggacgcggg gttccccggg gctgaggctg ggctggaac accccctcgaa      300 gccgcgggcg tcctgtccaa ggcgccccag gagggcgcag gactcgcagg gcgatgtcgc      360
```

```
ggggccctag gggaggaggt gaggacaggc cccggggggag cggggagttc cgggcgcccc      420
tcggttcccc gcgcgaggaa aagacgcggc gttcccttta agcggccgcc tcaacgggt       480 atcggtagcg cgggcgagcg gggagcgggg ggcggggggc ggggggggggg gggcggcgcc     540 gtttgaccaa tcgaagctca accgaagagc taaataatgt ctgacccggg cgcaaggcgc      600
agcctggagc tccgggtccc cgacgctgcc gccgccgcgc ccgggcgcac ccgcccgctc      660
gctgtcccgc gcaccccgta gcgcctcggg ctcccgggcc ggacagagga gccagcccgg      720
tgcgcccctc cacctcctgc tcggggggct ttaatgagac acccaccgct gctgtggggc      780
cggcggggag cagcaccgcg acggggaccg gggctgggcg ctggagccag aatcggaacc      840
acgatgtgac tccgccgccg gggacccgtg aggtttgtgt ggaccccgag gtaggcaagc      900
gctgggaatg gggcttggtg caggagctgc ccgtccgcgg gagagagttg actgggggat      960
cccccacccc aaagttgtgg gacgaggcca gtctccttct ttcctcccct ccggtagaag     1020
ggacgatttg gagttactct tggggagttt tctcccccat cccacaaccc agaaggtcag     1080
ccggcaccac cagggaaaaa gggacccggg gaagtcacga agtagaggag ggaaggcctg     1140
gaggagaccc agagctgcgt gatgggagca aagacggcga cccggggatc cctcgcagcc     1200
ctcccccagc ccaggagtag tcgagagaga cttaggggc cagagctgtc gagggtcctg      1260
actgagggga gggtgctggg gctaggctag gaatccttcc aggggtggg tggtccccgc      1320 gccgacttgc gggggagtg ggagggaagc ttgcgccttc agcccgcatc ccttccccgg      1380
agctgcacac ggctacctgc tccccaggaa ttgagactga agtggactta caagtccgaa     1440
gccaatgtag cttggaaaac ttgggaggcg gaattcctac cgctgggaac tgaaagggtc     1500
tgcgacactc tcgggcaggc cgaacccaca tctctaccca tcctgcgccc ctcttctgaa     1560
gcgccctcca gggaagttaa gagttttgac tttcggggag tggttgggat gtacgtgggg     1620
gattcttgac tcgggttagt ctctggggat gcagagccgg gaagaggaat gggtgagtga     1680
gttactcctg gaaagaaata gctgaggatt gggggctctg tgcctgacgg gcaagaagaa     1740
ggggagatta cagactaggg gcatccctaa ggaagaagcc tcggggctgc gagggtgaac     1800
tggaggatgc agtgtttgtg tgttgggggt agagcgggga tgagggaccg gggtggaggg     1860
gaggcgagga ggaggagggg acccagagaa cgaagctagg gaaggtagag ggtgccctct     1920
gccggccatg ctgccaagag cagctactgg gggcgggagg ctgggggtgg ggaagtggta     1980
aaggaaggtt ttgcgggatc ccttagagag ctggtaggag ggacttgttg aatggtgctg     2040
ctgactccag ctcggtgggg cgtgcgactc gtcgtcggtg gattttgact cctcgttctt     2100
gtttggcttc tatgcaagtt ttcctcgcgc tgggggagct ttgataagcc tcgattggcg     2160
gtgtgttagg gcttcttgga tcttatttta gggtcctcta gttatcctgc acttactcct     2220
taatgtcagt agcaaccaaa gaacattttc cgacaagcac gcaggaatgt tcttggccag     2280
aagcaaagaa aggcatattt ctgagtgttt attaatcctc ctagtaatct tttaaagcaa     2340
agtaatatgt aattgggaac gttgattttc taactgcata taaaaggcga catgatatta     2400
aatgagaccc ctcccctactg actcaatatc ctgcaaaatc tctctctccc ctttattatt     2460
atggaaaaat ctatttttat atgagtttgt tgtaaggtca aaagccattt ggtcttaca     2520 atttgatatg tctttacatt ttaacttatt gaggcataat tacagattta atttgtatga     2580
acgtgtgtgc cttcaatgct tatctcatgc aacataattt ttaggttgga gatttctgat     2640
gttatggcat gtagcgtttc aaggcattac acataatagg taacatagca tgttgaaatt     2700
```

```
acaccacaaa gttttgaccc tgggaacagc accttttaaa aacaatcact aaactcctgt    2760
tcctgttttc tgattttgca aatgccttgc ttaagacttt tttttttttt tttttttttt    2820 ttttttggg aaatttacct ctgggttagc aggagaggta aaaaaaagga aagagacact    2880
tgttgaaatg taaccataac ctttactgga atttaaaaca tgttggtcac cattactgga    2940
attccagggc cataaagtcg ttgtcttttt tttcttctac ttcattttgt aaaatgtgat    3000
aaatgttggt aaatatagac cagtagtaag tattatgaca ctaaaagcat tatgtatgtg    3060
gaactatttt aagttattac agaacatttt ctatttataa atgatataag cagaaagaaa    3120
tgatttccag ataaacaagg cttacgtaca tgttttgaag cattagaaca ttgcagacac    3180
tcttagacat cacattttt aaagcaaaat aacagtaatt tttcacatac ctttggagcc    3240
tttcatagcc cattcagagc tgagttagta gctggaagtt tcctttattt taaggtgata    3300
ttttaaaacc atttaacatg tatagtaggt caacattggt gcatccagaa aatgaagcat    3360
ttaggaaatc tgtttcagtg tcttttcaat gtgtgtaact tttacttgca aaccaatgga    3420
accaagaaag tcatcatttg cctaaaatgc agtcatcacc tcaaatgatt catttatact    3480
atgtgagtta attgccttca tctcattaat ggccaaggag ggaagggagg tcctggggta    3540
tttcttgttc attttgactc accaggaggg aaaatcctgt aaaaaaagaa atgcaaattt    3600
ctaaaatcct ggctcaaagt ccgtgggttt cctgtttaaa aggggcgcca tgaaaatgta    3660
agctattccc ttttcctgg aatctttaag agtcccagct tttcaatagt caaaatgtag    3720
atgattgata tcatttctta tatgaatagc actggtttgt agttcagcac gcacagtgag    3780
ctgggcacgc ccacctgata gtatagcaga gaacttgttt acattctttt tacattcatc    3840
ttctaaaacc tggggtgctc tctctctctc tctctctctc tctctctctg tgtgtgtgtg    3900
tgtgtgtgtg cgtgcacgtg cgcgtgtgtg tagaggggga gagagagaga gagagaactg    3960
tgaactgtga aatataacac agccagcagc tttgggtctc aatcgtagac ttactcttaa    4020
ggaaatttac agaatggaaa ggtcatgttc aagtagttta ttaacatttt gagatgtagg    4080
aaattaatcc cggagtacag aagaacaatt tcagacttcc tgaataaaaa cagacagcat    4140
agagagtgga tgatagctaa actctgaata tcttttgaga agaaaggcac tcccatttca    4200
ggtgcccata atatggattt gattttagtg attaaaacat taattttcaa cttgcatctc    4260
cctgtgtgga agagttcaat ttgtgtgagg ggtctcgcct atccaacaaa agtgaatatg    4320 tccctttat agggtaattg ctaacttgtc tcaacttgtt ttcaaacaat tgttatagag    4380
cactcagttt ccactaattg caaaattgtt gcttaattga aggactctca gccatctagt    4440
gcagccattc agccactggc aggctctgtg atctcaaact gtgaattgca ttttaaagag    4500
gaatcgagga gagaattctg tggaattcta ggttttaagt gctggctgtt gttcaatgga    4560
agaggaaatc atttgaacaa gaatcgcatc aagttgtgtt gtgataaatt ttctttatta    4620
ggatgaataa catgcacaga tgagcttcaa aagtgaatga gcaaactac tggttacact    4680 ctgcatccat ttactctgtt tagtatggag taatgttagg caataaatga tgctggcaaa    4740
tgaaatccgt atgttatttg catgtggtat ttaaacctag gaaacataga gtggctttgg    4800
tatttgtagg cttagtcatg tgtgtcctaa acgtcctctt aaacttctac ttaaggcata    4860
gaattattta atcctaaata attttatact taagtgcctc actggatttc cagaatattt    4920
acactgtaaa gatttagaaa ggtcatgaac ccaattattg actatatgga atcattattg    4980
atggcagatg caaaatggag ctcactaatg tactgacatt gaaaaccttt tgcagggag    5040 aggaggggga gtggtaaatg tgtgtgttct ttaagtggaa caggaaggta ttctcttttc    5100
```

```
tgtagaaaaa tttgagtatc tggtcagata agtgtggaag ctttcattta aattaagtat    5160
ttaagttcaa gtagaagctc tagggcactt atcctcttga tgagacaaat cttatcaaat    5220
atactagatg ctaagaagtg gctcattgcc ctgatgtctc atttatagat tgatgtttga    5280
ggatgggttg cattaagtga gttaggggggc tgagtgtggg acaggagaac gattggaagg    5340
aagcaaagta aatttacaag ctttagtgac agccataata aagtaaaagt ttatttccag    5400
agagcctaga gagtaaggaa cgttatatag ttttccccaa aggttcactt gaaagaactt    5460
ttcattggtt gtcatggtag taatgtcctg attttgaaat ctcccagaac ctagtagctc    5520
ttaaacatgc tttcatcttg gttcctttgg tctgacggaa actttatgac gaccctctgt    5580
gtttttgaca tgcctctgca ttttttggaga gaggaggtca ggcaagggag gatttcttaa    5640
aactaagaca gtatagtaag gaaacataaa attatatgat aaaaaatcac tgaacttcaa    5700
attgacttac tgaaataaaa cctagaaggc aacctgtcgt ttaattacaa ctagcttgta    5760
taaaattaaa atttataaaa tgggaattca agaaaataa acgggcagtt ccaagtaatt    5820
taagcaactc accaaaaatt gaagtaatag tgccacctag agaacaaaat caccagcttt    5880
actagccaaa tggcttattt ccatatgaac cattttccca acgctacagt tactaggatt    5940
tccttgttac catattcaga tcttgtgagt gtgtatgggg gtgggggttg catgtggaat    6000
tacagatgaa atttttaaaac aagcagatcc acaatttgat atatgcacta aatccttta    6060 acgttgtaat gtagccaaat gtagaatagc atgccaggaa tcaacggcta gcatccttt    6120 taacatttat tattttcatg gatatgtacc aaaccgaacc attgagtata aaggttctga    6180
ttttatttat ttgctacagg caattcatta tactttctga gatacaataa caccaaataa    6240
tttgagtaga gagacccttta agaatgtttt cgatttatga tctacccttta actttaatgt    6300 actcagaaga tgtgagaata aaataaagtc aaatataagc aagattttaa acacacacac    6360
aaaaaacaaa caaacaagaa aaaggaagaa aattataagg attgccttaa ccttagaata    6420
gatgaaggta tacatctgag ccagcaccaa aaaaaaaaaa aaaaaaagtt atggaaccag    6480
gaaccaataa ttacaaattg acttaaaatt cttggatgac aaaaatctat atttagttca    6540
tttttgcatg cgcccacaac agcatccaaa acagttctgg ggaggcactt tgataaatgt    6600
tgctgaatgc actaaatgat tgattaatgg ctgcttcaga ttatcactag tgatgtagac    6660
agaaacttca tgaaaatggt ttgtcttgct ggaagaaagg cagaaattgg aggaaaaggt    6720
ttaataatat ttttcccag tacctattat aaaagtcatt tagttggctt agttctataa    6780
tttcttatgt gtaatttgat tcacttatga aattgtgaat atatgaaatg ttaaagttga    6840
tttagacagc aactataagc ttgtggattt tcttttaaat gtcttcaaat ttttaaatgc    6900
cagtggagat gccagcgact gtgcttcagg gagtagaata tagtatatct taaatttgtg    6960
ccaatttctg gtaagcagag aaaaaattgc atgataacca agaaagtca tattgtttgt    7020 gctttgtgtt attcatggaa gcaatcaggt gcagaaaact ttcttttca gaaaaaaaaa    7080 attactaaaa taaaggtgcg tgtgtgtgta tgcacatata tctaaaggga gagagggaga    7140
aggaaactta ctaaataaaa ttttttgccac atgggattta gtctaatcag tcttggtttt    7200
ggagttgcta tcatcagtag ttccattttg tgattctttc tttctgcctt catgtgcctt    7260
tgaaaactga aactatgccc aaattaaaac aagttttcct gtcttttcac atgttcactt    7320
atttcttgaa tgtgttttta aacacagaca aacttctttt acatcatgta gaatctgaag    7380
gtcgagaaat ttgcagtcat tttgctggag agagatgctt ggcggagtcc caggccacat    7440
```

```
tcctaggcca aactctcgaa ggtattcctc ttatgcaaca ttgggaaaat acatccagca   7500
ccgacatgtt ggctgataat gtgtctgaag gcacagacga tatgcttatc atatgaaaca   7560
taaagccagc agatattgca gacattctgt tgaatgatag aatctggatc atttacattt   7620
acttaaatgt aaaatactat gattaagtac aaaaaaatca atttaggaga gaatagagag   7680
ttgcgggcac ggttttaggg gatgacttat cagcagattg tagaaaggaa gcttgaatgt   7740
tttaaattaa ctgcaagttc agtataagcc agtggtgtga caagaggctg ttatcatagc   7800
tactgaaatt ttgggctgca ctgctagaaa tataatactg aaatggagaa gctaataatt   7860
cttcactttt taaatagact gtatctagaa tattatcatc agttcaagga aatgaaataa   7920
gttgttttag gtacatcatc gataaattag tgtacattca aatcactgtg accaggatgc   7980
atagggaatt tgaaagcatt gcatgtgagc aatggttgag gggacttgga atgcatgact   8040
tagggacaag aaaacttagg ctggaatggc aagtggtttt tgaatgttgg gttgagaaga   8100
attctaaaac tgtgaaggat tagtaaaaat aacattcaga ttgctaatgc ctactgtggc   8160
tgggagatta gagtgtcaac atgtgtgatg tattttttgac atccttattt tgaggatggg   8220
cttcaaagat ttgacgaact gtcataagtg taatttgtgt tgcttcagac agcagttcta   8280
gaaccaatga tgtaaattta gatactctac atggtagtta gaaaactttc cattaattta   8340
atttagcaaa tattgaatgc tcactgcata cagagcactt tattagagga atatataata   8400
aagaaaaaag aggtctggtg tggtggctca tgcctgtaat cccagcactc tgggaggctg   8460
aggtgggagg atcacttgag cccaggagat cattacgagt ctggacaaca tagcaagacc   8520
ccatctttac aaaagacaaa aaaaattatc caagcctggt gacaggcact tgtagtccca   8580
gctacttggg aggctgaggc agtaggatcg tttgagccca ggaggttggg gctgcagtga   8640
gccgtgattg tcccactgct cttcagcctg ggtgacagag tgagacccg ttggagggaa   8700 ggaagggaag gaaggaagaa aggtaggaag gctgaaatga aacccttta gaaatgacac   8760 taaaatggga ggttggagta aggtattttc tgaagtgcct ttgtacttgt tttttttctaa   8820 tgcattggcc ataagtctgc tccttattta tagtccataa acaatcctaa tgagaacagt   8880
tatatatttc tgcctttgaa tcatctactt gaagtgttta gcatcatgaa ttgagtatca   8940
gaaatccctc ccatttcttt gcaaagcgct gtattttact tttccttatt tgtatacaga   9000
ttctcaaaat tggctatttt tcctttgggt tagacagaac agaatgtctg gaaaaaaaag   9060
ttcttatcaa attcaggtgc ccaaattgct taagaaatta acttttgagg ttatattttt   9120
ttagggttca gtagctaaac taagaaaact tctcaccgtt caccttcact tttgaaacc    9180 acaaaatctt cagatattac agttttccaa agagtttctc tttttaaata taaactaaaa   9240
ggaattgact cctcccccaa ctccctcagg cctcagcatg gatagagtta cttttttttct   9300 ttaataattt atttataact tattttgctc ttctgtagaa cagctggaga ttaagcaaca   9360
tggccatgac ataaaatgca agttagacca taagatgagc agcccactcc aagtatgaat   9420
gagtacttat tctttgtgat ctctcatact gcttttaggt attaatagtg tcagtcagca   9480
aagcaaacag tttaatattt acatctcctt taggatatca tatagtttat agtttgtatg   9540
tgttcttgcg tgtatgtttt cttctgtttc aaattctttt ttcttaaagt aagaatgtta   9600
tatgtagcaa atggttcttt cattaattca tttgttaatt caccgtgcat taattgagtg   9660
cccagtgagt gtcaggcact gggctacttg gatttctttt ccctgtattg atccatatat   9720
cttcaggtgc tccttgatat ggctctccat tgactctctc atataaggct ttcattacct   9780
attcacatac tccctcccaa agaggactgg tccaaaagta aaatcttgag caagttctct   9840
```

```
gagttatttc agaacttctt gcccccaaac tgtattttta attattgact ggtagcattt    9900
tggaataact tacctctctt ttttaaagat tgaagttctt tatcctctct gattttcagg    9960
tgtcagtttg tgtacaaatt gagacaataa aaatgtttgt tagacatttt cttaaagcat   10020
tttgctatgt gagaatcttt catgaagaac tcttttttaac aatgactcta tagcagaagc   10080
cacagtagag ggagaactac tgaatcaaag atggtgtttg agtctatgat tttatgatgg   10140
atttttttt ttttacata caaggatatg catgggtctt ttagtattca ggaatctgtt   10200
cttcacttga cagtatttat aaattgtgtg ttcccccta aaaaaactta aattgtgaga   10260
atgcttccat ttactagaag ttggttaatg attatgccaa ataaggaaaa taagacagaa   10320
aaatcagttt agtgaatact attttgcctt taaatttagt aatttagtaa cagtatctct   10380
ttggggttta ctagaaacca ctttttaatc caataggtct ctttcattgt gaagtcagga   10440
ggtgattttg cttaaatgtg tagtatagga atctatatgt ggtgttcaag gatcatgtaa   10500
atatgctgat ataatcggag cacagtttgg catcattaac tcagaaatat ttaaactctt   10560
gctatacaac atggaagcaa acttgtgcat agtttgtgtg tgtgtgtgtg tgtgaatctc   10620
aaaaaaagaa aaaaatcaca ggatcaggaa gtcggaatag gtcccacttt tcttctagta   10680
ccaaacctac agccatgttc ctagccttct cttttactcc caagcaagac agacaggcaa   10740
atgaccatcc tgctgcccat ttctgtgtat attcacttgc attgagagtt gtattcacct   10800
gcttgttgag agtattcaca aatggtacct gataaagtag atacttcttt aaacatgtga   10860
atttttttgc attgtataat gtttagaaat aatcatgtat aaatggttga atattaatac   10920
aggattgcct tatcaagtat tttattaatc attaaaatgt ggtgtcatta atacaattta   10980
ttttaagtgc ttttcctaaa ataccagatt atttttctga ttttcacatc cctgacaatg   11040
actttcttaa acttggtagc caggaacaga aaacctaaca ctgcatgttc tcactcataa   11100
gtgggagctg aacagagaga acacatggac tcagggaggg gaaccacaca cactggggcc   11160
tggagcaggg ggcaggggaa gggagagagt gcgtcaggac aaacagacaa atagctaatg   11220
catgcgagcc ttaataccta ggtgatgggt tgataggtgc agcaaaccac catgacacat   11280
atttacctat gtaacaaacc tgcacattct gcacatgtat cccggaactt aaagtaaaat   11340
aaaaaataat aataaaataa aataaacttta gtagcatcta ttgttccaga gcctgtaatt   11400
gctcttcagg cagtctcaca taaaaaccta ggagaacctt cactgtcact gttccatgag   11460
gtgttaggaa aacttgctct actgcagtgc cccagtaggc attggtactg agaccaaaat   11520
tcagctggtt tgttgttact acgattccta cgtgatttca cttgtcatgt agacaagatt   11580
gcacacttca ataataatct tgtccaaatg tgtggtattc catacatttt taaaatgcat   11640
tcacatatct cattccattt gatcctacaa ataactctat aaaaaagatt ggcagacatt   11700
atttctatat aacagaggag gaaactggag cttagagaag ctaaatagca atccaaaatg   11760
cacagctgta gaaccagagc aaggatgata gcccagtgac ttcacctaac ctagtcccct   11820
taccaccact ccagctgtct ataaccaaaa cctgcagtat tcaagtaaga aaccatatct   11880
tgcccttgat gcattaatgt gagacctgga gcaggaacag gctgatattg tcaccctggc   11940
ctactgtcca cctttgtctc cagcagagac tggtaccctt ctgtgtgcca aggaataaag   12000
tggtaatggg aagattaaaa atgttttttc caaggagttt tttaatttaa tttttttaaa   12060
aaagaaaaaa ctcttagagg gaaaatgaa tatatgactt tgatgtatt gttccttagt   12120
aacttagtta taatttttact taaacctgag actcttgcta agtgaatgat tagaaatatt   12180
```

```
aggtggctgg ccagatggca aataggaaca gctgcagtct gcagctccca gagagatcaa   12240
tgcagaaggt gggtgatttc tgcatttcca actgaggtac cgggctcatc tcattgggac   12300
tggttagaca gtgggtgcag cccatggagg gtgagccaaa gcagggtgga gcattgcctc   12360
actcaggaag cgcaaggggt caggggaact ccctcccta gccaagggaa gccctgaggg    12420
actgtgccat gagggacagt gctatctggc ccagatacta cacatttcct acagtctttg   12480
cagccggcag accaggagat tcccttgggt gcctacacca ccagggccct gggtttcaag   12540
tacaaaactg ggtggccatt tgggcagaca cccagttagc tgcaggagtt ttttctcata   12600
ccccagtggc acctgaaatt ccagtgagac agaaccattc actcccccgg aaaggggctg   12660
aaggccaggc agccaagtga tctagctcag cagatcccac ccccatggag cacggcaagg   12720
taagatctgc tggttttgaaa ttctcactgc cagcacagct gcctgaagtc aacctgggat   12780
gctccagctt ggtcggggga ggggcatccg ccattactga ggcttgagta ggctgttttc   12840
ctctcacaat gtaaacaaag ccactgggaa gtttgaactg ggtggagcct accacagctc   12900
agcaaagccc ctgtagccag attgcctctc tagattctcc ctctctgggc agggcatctg   12960
ggaaagaaag gcagcagccc cagtcagggg cttatagata aaactcccat ctcatgggac   13020
agagcacctg ggagagggg tggctgtggg cccagcttca gcagacttaa atgttctttg    13080
cctgttggct gtgaagagag cagtggatct cccagcacag cacttgagct ctgctaaggg   13140
acagactgcc ttcttaagca ggtccctgac cctcgtgatt cctgagtggg agacacctcc   13200
cagcaggggt cgacagacac ttcatacagg agagctctgg ctggcatctg gtgggtgccc   13260
ctctgggaca aaccttccag aggaaggaac aggcagcagt ctttgctgtt ctgcagcttc   13320
tgctggtgat acccaggcaa acagggtctg gagtggacct ccaccaaatt ccagcagacc   13380
tgcagcagag gggcctgact gttagaagga aaactaacaa acaggaatag catcaacatc   13440
aacaaaaagg atgtccacac gaaaaccccg tacaaggtc gccaacatca aagatcaaac    13500
atagataaat ccacaaggat gaggaaaatc cagcacaaaa aggctgaaaa ttccaaaaac   13560
cagaatgcct cttctcctcc aagggagcac aactctttgc cagcaaggga caaaactgg    13620 atggagaatg agtttgatga attgacagaa gtatgcttca gaaagtgggt aaaaacagac   13680
tcctccaagc taaaggagca tgctctaacc caatgcaaag aagctaagaa ccttgaaaaa   13740
aggttggagg aattgctaac tagaataact agtttagaga agaacataaa tgacctaatg   13800
gagctgaaaa acacagcacg agaactctgt gaagcataca caagcttcaa taactgaatc   13860
gataaagcag aggaaaggat atcagagatt gaagatcaat ttaatgaaat aaagcatgaa   13920
gacaagatta gagaaaaaaa gaatgaaaag gaaggaacaa agcctccaag aaatgtggga   13980
ctatgtgaaa agaccaaacc tacatttcat tggtgtacct gaaagtggcg gggacaatgg   14040
aaccaagttg gaaaacactc cttaggatat tatccaggag aacttcccca aactagcaag   14100
acaagccaac attcaaattc aggaaataca gagaacacca caaagatacc cctcaagaag   14160
agcaaaccca agacatgtaa ttgtcagatt caccaaggtt gaaatgcagg aaaaaaagtt   14220
aagggcagcg agagagaaag gtcgggttac ccaaaaaggg aagcccatca gactaacagt   14280
ggatctctca gcagaaaccc tacaagccta caagccagaa gagagtgggg ccaatattc    14340 aacattctta agaaaagaa ttttcaaccc agaatttcat atccagccaa ctaagcttca    14400
gaagtgaagt agaaataaaa tcctttacag acgagcaaat gctgagagat tttgtcacca   14460
ccaggcatgc cttacaagag ctcctgaagg aagtactaaa taaggaaagg aaaaaccggt   14520
accagccact gcagaaacat accaaattgt aaagaccatt gaaactatga agaaactgca   14580
```

```
tcaactaatg ggcaaaataa ccagctaaca tcataatgac aggatcaaat tcacacataa    14640
caatattaac cttaaatata aatgggctaa atgccccaat taaaagacca cagactggca    14700
aattggataa agagtcaaga cccatcagtg tgctgtgttc tggagaccca tctcacatgc    14760
aaagacacac ataggctgaa aataaaggga tggaggaaga tctaccaagc aaatggaaag    14820
caaaaaaaaa gcaggggttg caatcctagt ctctgataaa acagacttta aaccaacaaa    14880
gatcaaaaga gacaaagaag gccattacat aatgataaag ggatcaattc aacaagaaga    14940
gctaactatc ctaaacatat atgcacccaa tacaggagca cccagattca taaagcaagt    15000
tcttagagac ccacaaagag accaagactc ccacacaata atagtgtgag actttaacac    15060
cccaatgtca atattaggtc aacgagacag aaaattaaca agcatattca ggatttgaac    15120
tcagctctgg acccagtgga actaatagac atctacagaa ctctccaccc catatcaaca    15180
gaatatacat tcttctcagc accacatcac acttattcta aaattgacca cataattgga    15240
agtaaaacac tcctcagcaa atgcaaaaga atggaaatca taacaaacag tctctcagac    15300
caaagtgcaa ttaaattaga actcaggatt aagaaactaa ctcaaaacca tacaactaca    15360
gtggaaactg aacaacctgc tcctgaatga ctactgagta aataacaaaa agaaggcaga    15420
aataaataca ttatttgaga ccaatgagaa taaagataca ataccaga atctctggga    15480 cacagctaaa acagtgttta ggggaaattc atagcaataa atgcccacag gagaaagcag    15540
gaaagagcta aaatcaacac tctaacatca caattaaagg aactagagaa gcaagagcaa    15600
acacattcaa aagctagcag aagacaagaa ataactaaga tcagcagaga actgaaggag    15660
attagagaca caaaaaaccc ttcaaaaaaa tcagtgaatc cagaagctgg ttttttgaaa    15720
agattaacaa aatagataga atgctagcca gattgataaa gaagaaaaga gagaagaatc    15780
aaatagacgc aataaaagat gataaagagg atatcaccac tgatcccaca aaaatacaat    15840
ctaccatcag agaacactat aaacacctct atgcaaataa actagaaaat ctagaagaaa    15900
tgaataaatt cctggacaca tacaccctcc taagactaaa ggaagaagtc aaattcctga    15960
atagaccaat aataagttct gaaatcgagg cagtaattaa cagcctacca accaaaaaaa    16020
gcccaggacc agacggattc acagctgaat tctaccagag gtacaagaa gagctggtac    16080 cattccttct gaaactattc caatcaatag aaaaggaggg aatcctccct aactcatttt    16140
atgagtccgg catcatcctg atacaaaaac ctggcagaga cacagcaaaa aaataaaatt    16200
gtaggccaat atccctgatg aacattgatg caaaaatctt caataaaaaa ctggtaaact    16260
gaatccagca gcacatcaaa aagcttatct accatgataa tttggcttca tccctgggat    16320
gcaaggctgg ttcaacatat gcaaatcaat aaagataatc catcacataa agagaaccaa    16380
tgacaaaaac cacatgatta tttcaataga tgcagaaaag gcctttcata aaattcaaca    16440
gcccttcatg ctaaaaactc tcaataaact aggtattgat ggaacatatc tcaaaataat    16500
aagagctatt tatgagaaac ccacagccaa tatcatactg aatgggcaaa agctggaagc    16560
attcatttga aaaccggcac aaaacaagga tgccctctgt caccactcct attcaacata    16620
gtattggacg ttctagccag ggcaatcagg caatagaaag aaataaagca tattcaaata    16680
ggaagagagg aagtcaaatt gtctctgttt gcagatgaca tgattgtata tttagaaaac    16740
cccatcatct cagcccaaaa tctccttaag ctgataagca acttcagcaa agtctcagga    16800
tacaaaatca atgtgcaaaa atcacgagca ttcctataca ccaataatga caacagcca    16860 agtcatgagt gaactcccat tcacaattgc tacaaagaga ataaaatgcc taggaataca    16920
```

```
acttacaagg gatgtgaagg acctctttaa agagaactac aaaccactgc tcaatgaaat    16980
aagagaggac acaaacaaat ggaagaacat tccattctca tggataggaa gaatcaatat    17040
cgtgaaaatg gccatactgc ccaaagtaat ttatagatcc aatgctatcc ccatcaagct    17100
accattgact ttcttcatag aattagaaaa aactacttta aatttcatat ggaaccaaaa    17160
aacagcccgt atagccaaga caatcctaag caaaatgaac aagctggagg catcatgcta    17220
cctgacttca aactatacta caaggctaca gtaaccaaaa catcatggta ctggtacata    17280
aacagataga tagaccaatg gaacagaaca gaggcctcag aaataacgcc acacatctac    17340
aaccatctga tctttgacaa acatgacaaa aacaagcaat gcagaaagga ttccctattt    17400
aataaatggt gtcgggaaaa ctggctagcc atttgcagaa aactgaaact ggaccccttc    17460
cttacacgtt atacaaaaat taactcaaga tggattaaag acttaaacat aaaacataaa    17520
accataaaaa ccctagaaga aacctaggc aataccattc aggacatagg catggcaaag    17580
acttcatgac taaaatacca aaagcaatgg caacaaaagc caaaattgac aaatgggatc    17640
taattaaact aaagagcttc tgcacagcaa aagaaactaa catcagagtg aacaggcaac    17700
cgacagaatg ggtgaaattt tttgcaacgt atccatctga caaaaggcta atatccagaa    17760
tctacaagga acctaaacaa gtttacaaga aaaaaaacaa ccccatcaaa aagtgggcga    17820
agggtatgaa cagatgcttc tcaaaagaag aaatttatgc tgccaacaaa catacgaaga    17880
aaagctcatc atcactggtc attagagaaa tgcaaatcaa aaccacagtg agataccatc    17940
ttatgccagt tagaatggcg atcattaaaa agtcaggaaa caacagatgc aggagaggat    18000
gtagagaaat aggaacactt ttacactgtt ggtgggagtg taaattagtt caaccattgt    18060
ggaagacagt gtggtgattc ctcaaggatc tagaaccaga aatatctttt gacccagcca    18120
tcccattact gggtatatac tcaaaggatt ataaatcatg ctactataaa gacacatgca    18180
catgtatgtt tattgtggca ctattcacaa tagcaaagac ttggaaccaa tccgaatgcc    18240
catcaatgat agactggata aagaaaatgt gacacacata caccatgaa tactatgcag    18300 ccataaaaaa ggatgagttc atgtcctttg cagggacatg gatgaagctg gaaaccatca    18360
ttcttggcaa ggtaacacag gaacagaaaa ccaaacacca catgttctca ctcataagtg    18420
ggagttgaac agtgagaaca catggacact gggaggagaa catcacacac tggggcctgt    18480
cagggtgtag gaggctaggg gagggatagc attaggagaa ataacctaatg tagatgacaa    18540 gttgatgagt gcagcaaacc accatggcat ctgtatacct aggtaacaaa cctgcacgtt    18600
ctgcacatgt accccagaac ttaaaagtat tattattatt attataataa taataataaa    18660
agaaatacaa taaatagaa tgcagcatac agcagtgatt ctcaaacaca ttcagcatca    18720
gaattaccct tgaatcttta aaatatatat acatatgaga tcttagtctc caagatttgt    18780
aagtttggta ttgggtccct gggcctatgt tgggtttaga aacttctaca gatggtttgg    18840
atgtatggga cagtttaaga atcgctgaac taaaatcaaa taaactgaat atcctgtgat    18900
ttagagagac ttatcgttta tttcactatc caagtacttg cattagagcg tggctagaag    18960
ggatttgcag ccttgtaaat aatcagaaat tcagacattt tgagatgaga gaactgctga    19020 agatttatt ctgacttgaa ataaattttc taattagaaa cttccaggtg agagcaaagg    19080
cctggaacaa tattcctgag ccagaggagg atcgagtttg actccaggcc taacacttac    19140
taggtctatg accttgggtc agtaatttaa attctctgta tctcaacctc tcaacagggt    19200
attggtaggg attaaatgtg ttagtgtctg tgaagtgctt agagcagtgc ttggcatagt    19260
aaatgcttaa tgaatttcag ccactgtttt tattttagt actttccagc tccccaaaa    19320
```

```
agatacttt  tttagacttg  tattaagaca  ataaaaagtt  taatcagcat  gcttcatacc   19380
taaatatgct  tcactttata  gcaaagttta  caagactaaa  actgttttgt  tgtaattctc   19440
tgagtctcat  gtgttatta   atgatttttt  ctgctgttta  ttcatctgaa  ttctactcat   19500
tcttcaagac  ctagctggaa  tcctgttcct  agaaagactc  ttgcccataa  taataaacct   19560
gccctatctg  agttcctagg  tggtctgtac  ctcataattt  ggtaattaat  tgtatatgca   19620
cttatataac  aaaacattat  tgtgtgtctt  tgctgtatca  gattctaggc  tggaagttgt   19680
agatatgatg  tttttgtcta  gaaaaatgtt  ctagaatgtc  ctactcagga  cagtctgttg   19740
actttaaaga  cacatttcct  aaacagacac  ttcatgaggc  agcccagcc   tgtacctgtg   19800
ttcctggacc  tgatgatcaa  gtttgattta  agcctcacca  cttactagct  ctgtgatttt   19860
gggcaagtta  cttgaattct  ctgtgtgtag  atagaacaat  gttgagggaa  atcccttcc    19920
cccatccttg  tgtttccaca  agggaacttg  cttcctaata  agtaacactt  tcagggaat    19980
attctaggcc  cttctcttat  ccccattact  tgttctttct  gtgaaaagag  gagaggttaa   20040
tctgatggat  gaaatcctta  atctttcatc  ttctggactg  tagagcctgt  gaaccaaagc   20100
aatggaccac  ttgcactgaa  attgaggctg  accctgtatt  ttgattctta  tttggcaact   20160
tatttctatt  ctgttcccaa  ttcaaaatcc  caaggggaga  aggaagataa  ttgattacca   20220
gaagtatgta  atggtggtag  gaagttgaat  aaatggtaac  ttttttaaaag  ttgcatgaga  20280
tatagtcctt  atcccagaga  agctaagttt  gcttttcttt  cctctcatgt  attttagtat   20340
tatttctaca  attagattgt  aaacccttta  aaagcaagaa  tatttctaca  ttttcttact   20400
cctgatagca  cacagtagac  tgctgggcac  atacatagta  ggtggctctg  taggtacttg   20460
ctaaatgatt  caacatgttt  ttccctcatg  gaaaagaaag  atttcagtat  tgttcttatc   20520
agctaggaag  gcactctgaa  taggaaatca  gttctaggca  ggtatccata  aatgggttat   20580
gatttccaac  ttacttgccc  cagaggctcg  ctaatgttga  actcttcatg  ggtactttgt   20640
cttgcttcat  gagctataca  tgctaagggg  ttagcagatc  atataatctt  ttgatctaca   20700
aaatatgatc  tttattgaac  aaaaacttgg  gccaaaggcc  tttctccttt  gccaccttcc   20760
tccctctttt  cattctcttt  tttgggaatg  ccctttgtgc  atgttagtta  cagcatgtac   20820
cacattgcac  tgtattgttg  gtttttgggt  ctaacccacc  cttaacactg  cagtccccaa   20880
gggcagaaat  tcagtctcat  tcattttgat  gtcctcagtg  cctgtgctca  gagaatatct   20940
attatttgaa  aaaatagtgc  aaaagtaaat  tttaggagac  tacatcacac  tcatctaaac   21000
tgcaagtttg  acaagttgac  atccaaaaga  aaggctctcc  taaataaacct  cgccacagaa  21060
atttgggtga  cctttgtagc  tctggagaaa  gcagaggcaa  aaatgaaacc  taaaaattat   21120
ttgtgggttt  ttaaaaaatg  ttttctcatg  gagtaaaggt  ctacagctga  gttcttttca   21180
tatgagggaa  tgacagaaac  acagctggtt  ctgactttca  gcttcaactg  agcgaccaga   21240
gctctgctgg  tgaaacagga  acttgtattg  tgcccctgac  gtgcaccttg  aaggtgtcag   21300
ctcattgtcc  cttttgttcac ataaatagtt  ttttaagaat  tgttttttgat cttgtgagcc   21360
tctaactaaa  tgattaacca  tgcaaagttg  gccatttggg  gtaatactga  agcacttctc   21420
ttgagggcta  ttgacaggtg  ggaatgtgcc  cacctccttg  ggtctctggt  tttcatgtca   21480
tacttgcaaa  tcagtgacag  tttaaacttg  gggcaatcac  ttagcaagtc  tattgagtta   21540
ccaagttaat  tattcccact  ttgcatgaag  caaccttgaa  aatgattttc  ctaaagcaaa   21600
gtacatccaa  actcagtacc  ttcttaataa  cctttgctga  atgaataaat  gactaattca   21660
```

```
taaaaaatgt aacatatctt taattcttac ttacgggcag tttaagcctc ttgtgtaaga    21720
ggaggcctcg gcttgagata acataggata gtaagcctcc tagagaaatt tctatatgga    21780
aacatggtct gctatgaagc tagaagtgag aggacattat atttgaccat tatatttggc    21840
ttcagagctt ctcaacatgg ggcccaaagt caaggtccct tgtttcatta agaggaggtc    21900
caggagtgca tgacacccat cagactactg agcccagct ggaactaggc accttgcaca     21960
ggggccttgc ctaatcaaaa tagttcttat tttttctgag ttccaagtaa ctagtttcct    22020
aacccagtgt ctggatagta gtgccaagtg ggagtacctt caatgaactt cctcatgagg    22080
ttatttctag cctattggaa tgtttcgttt taggagggtg aggaagggaa gtcttgaatt    22140
tttgtgctta gtttaatgtt gtgatacagc tttgaccatc cgtttaatgg agatctgtt     22200
ttccagatga ctatacatgt ggaaaggaga agttttttga gtgttttttt taacccctt     22260
taaagaatgg tttttcattt agtctctaca tttgggggta aaaggtcctc tagggagact    22320
tttcaaaagt atttgaagtt tgcatctgat ttcagaggtg agttggaggc ctatctgtgt    22380
atgacagaca catgtctcca acaactatat gttcacaagg actaagagcc atcctttgg     22440
gtccatcatt caacattgat ctcacattcg tgttcgtatc agtatcttta cagtgcgctc    22500
ccagttacat ctccctaatt tcccttagta ggcttcacag aatttgcagt gtatgcaatg    22560
gcagatgacc acatgtggag tcatttaacc acatcttcca ctgcaagtca gcccgctctt    22620
gatgtctgtt tatgtttaga ttccatcttt tggaagattt cattcctctg cactatctca    22680
gtatctcaga tgcttttgag actgggtcct tttcccctcc tatgtttggc catggccacc    22740
ccctcagggt tgtgttgtgt ttcacagctg ctgtttgtag ggttgacctt tacaatgtac    22800
aaagctcttt cccatatgtt gacaatccct ggtgtgatgc tgtgagttag gcagggtgtg    22860
tatacgtgtc ctcatcatat tacagtggta aggcaacagg gtttttgaat ttgatcaccc    22920
atgaatttgt ctaatttgtt ggtaaaaaat ggtcatgtat cagccgtttc acagggtcag    22980
cttaatagaa agtgggagtt aggcaggacc agaattcagg acttcagccc ccggtcccag    23040
ggactattct ctatacccaa ttgtcccacc ttgaatcagt ttcttctagg gaaatatctc    23100
caaaactgag atggcaccca caggacttct taattgtagt cattaccagg aaaaacaagc    23160
aaaggaactg gtgtaaatct ctgttttttgg tgattggtgg agatttggag attgtcttgt   23220
gtcaaaagta aagccactag attaaatgtt ttgttaataa attggttatt tttaatttaa    23280
ttatttgaca gttaatttac attattcaaa aatcaaaata aaatttaaaa gaagtttaca    23340
ctgaaaagtc ttgccccact tatacccctgc tcacctcagt atcccccaat acataccatc   23400
tataaggtga tcatttgtat tagtttcttg tgaatccttg atagtgtgtt ttatatagat    23460
acaggtaaat atgagtatgt actattattt cccccccacc ccaccctgtt ttttttttga    23520
gacggagtct cgctctgtcg cccaggctgg agtgcagtgg cacgatctcg gctcaccgca    23580
agctccacca ttttcccca ttttttaaaac aaaaggtagt agccatatat acactatttt    23640
acaccttgtt ttatcactta ctaatatata ccagagagct ttccatcatt ttgtacatat    23700
gcacctatat ctgtcaatta ttcccagaag tggaattgct gggtcagcag gaaaaatcat    23760
gtataatttt gataggtatt gcctaattgt cctgcacagg gcttgaattg tttgtactcc    23820
cacctttagt gtatgagaag acctgtttct ccatagcctc atcaaacaga gtgtgtgaga    23880
ttagatgaga aataggaggt gagcagtctt ttaccccatc cgtagtttgc agtgggaaca    23940
ctgcacagtt gcaagagctg gtgcaggtat cagattagtt ccagtggaaa cgctgcctca    24000
ccatggccat gggcttgcgc cagctctagt gacacacacg gaatggaccc acgttgccac    24060
```

```
ttgcagaatt tcctgtagca gaaagttgaa catgcattca ttattcatct aactagccat   24120
gctggatcta aagagcacaa cagtgttttt tagaaccaaa aagaaaattg tttcactaca   24180
acacactgtg tataaggctt tcaatgctct tttctcagct attaacatta ttttcaggac   24240
tgagttcaag agatgtatcc caaatcacag ggatgtcttg ctaagcttgg aactttcata   24300
ctcaagggat gcttttttga ggaatgattt tacacttact caacatttgt aattaaataa   24360
ttagtacttt ataagataaa tttaaactgt ccaagtacaa tataaacatt gaactatgat   24420
gcattattgc tagactttt ccttaaagtt gccaagtggt ttcctgcatt aggcaaatag     24480
gggatcatat aaaaatgcca tgatttacgg cctagataac atctccacca tttgagcagc   24540
atatattcca ggtcatcccc acataactcc ttaccattct cattagaaag gttgattctt   24600
agtcttattt ttctctgagg acagcaaaaa aaaaatccc cttcagttcc actgcataga    24660
aaagtgtggt aaatggagcc gggcacagtg gttatttaat ttaaatggac aatattttt    24720 atagaatttt gacagggcca ctgtataggg gaaagtcact cctcttcccc tttatagaag   24780
agttgcacct ggacagttgc attgatgact gtatccagtc tacacaagag gtcattcctg   24840
ggcataagaa tggactgcca aaatctagct gaaacaccat tgacaaatag acattttctt   24900
ttgttaataa tacctgtgaa ggctttcata acagacattt ccagttttgt tctcaggctc   24960
cttgcagctg ctcctctaaa agtgtgctct cttccaagag ctgacaatgg ccagaagcaa   25020
ggtgttctgt cttttgtgcc atcatcatct aacttgccac acacatttgg gatgtcagcc   25080
taggtatagg ttttgtatcc actcagtatg gcttgtgggt ctggttgcct ttgttattca   25140
tgctgagggc ctctgggcat cagtttggtg tgagagaacc cattccatga ccctccttcc   25200
tttggctgtt ttgactcgat ggctcttgtt ggcacagtct gtgagtgtct gatgctctat   25260
ccatgccgga ccatctgttc tgctgtctct gtggtctgaa gtcgttttct gaactattcc   25320
ttgataataa atttgagatg atcttgttct acctttcttt tcaagtcaca tcttagcccc   25380
ttagccacat tcccgaagaa catgacaaat ggatgggtca caagtcacgt agcataggt    25440 gtcagaccac gaggctttga agggattctg ttgggtgcta aaaagaaaga ttttgtgtca   25500
ccacgatttt tttttaaaggc atgttgacac ttaggcctta attgaaagcg ttcttactca  25560
agtagagttg acagaggagt atttggtagt cgcggttgct ggtctgaaga gcatgtggtt   25620
ctgtttcaat gcccaatgag atcttctcac gggaaaatgt tctgacatct caaacaaatg   25680
accttcatgc atagttttga caaaataccc tattaagtat gcatatatgg ttggtacctt   25740
gtggtaataa ttcaatactg gaaacagagt agcaacaaag aaacattagg gttatattta   25800
acctctgtgg aattagtgtg taaacaaact gcttatcaga aatgctcata tggggctttg   25860
tttaaataaa taagaaactg gcatatag gg tctgcaggat atttctgcca agtagacctc    25920
cctcacatta taagacacca catctatgtc tgaccccata tggaaagagg catagcaagc   25980
cagcactggt tcatattccc tctccaccac ataatgggta tgtgatctta gggaatccac   26040
cgaaactctc tgggcctcag tttcctcagc tataaatggt ggataatcaa attatttacc   26100
tcaccattaa taaatgttag ctattatttt ttatcaagtt taatacaaag agaaacattt   26160
tacttatttt tccagctatc cagagcatct tccaaaatcc tatcaccaac aaatactgta   26220
ttgtatttat tatagcaact atgtaaaaat ggagtccctg tcctatgctt agatgaaata   26280
tgttggtatt tgagtttgca tgtcttctat aggaatcagt gtttagtgaa aacgggtgga   26340
gataaacaga tgttttcaca gtcctgttgt tcacagtacc gccaaattga atgtttccat   26400
```

```
ataggtgcat tctaatggct taaatgatgc agatattttc tggccagcca tatggatctt   26460
ttgtcatcta agatgttaat attttcctta tattttatag tagttctgga gtacagccag   26520
tttcttgaat agggtccaca tggctcatta tgcacagggc ctggaaactg ccttactcgt   26580
gctgttgaaa tgaaccgtga cacttcagaa gagctgggag ctggggtaga gcagtggcta   26640
ggagaacata ttcaattata tttcctcctg cattaagcta caagtaatga gcactttcct   26700
gtgctttaca gttaagtaat taaagaaat tatagagtgg gatgcaaaaa taacccgaag   26760
gacaactgga tgtgtggagc caccagtttt ctccatgagt gcacaaggtt aatccttgtt   26820
actactcaga atgctgagtt tctacagaaa gggttgcagg tccacacatg ttttggcgtc   26880
tacccacacg cttctgtatg gcatgactgt gcatcccaga agaagggctg tgctgtgtac   26940
ctccacgttt cagtgaatt taacaaactg atccctgaaa atggtttcat aaaggtgagt   27000
aacagagagc taatagcctt ctcttgctaa ttttatcttt cccccaagat tcttgataa    27060 tagtttgaaa aggagtgtta ttctttggtc tctagaggca acttaccttt ccagtttctt   27120
ccatcacctg ttttcatctc tcttgttttt ttaaatttaa tgctgtatgt atttcagagg   27180
ataggatcta atctagtgcg gtcccttcat caggtgagaa ttattcatct cattttcatt   27240
ttagcccttc tgaattaatg acattgaagc ccggcagttt ggtcctaaga tgggtttaat   27300
tatgtacaga tactctttct ataatggaaa ttgctcagat aactaattaa ccacaagaat   27360
acactgtcta tggaaaattt caggagcacc gtctgtggaa aaactgggaa gggcatgctg   27420
tcaccacagc tctggggtct attaaaagtg tggttatgca gcactggtgt ctagtggggt   27480
gttggctctc aactgccaga attcccatag catttcatgg cagaaagtca aggtgtccag   27540
caatactctg aaagtgacct gttgattaaa gtcgtcaatt ctgaagaaag agactgaaat   27600
aagacaaatg ggtcttaact tttttctct ttctctctct tgtaaaaatg tgtgattgtt    27660
ctggcatgtt cccaatcccc acataatgcc aacatctttt cttaaagggg gattccsttt   27720
atccttggat ctgagaatta ttgcatgttc tccctttagg acaatgaat gcagttgcat    27780 caccccttgct tttttttttt ttttgtaca cagcatgctt attcttggat gcagggactt    27840
gaaagacaaa gccccacctg gctttcacaa catctcctat tagtaggtgt gccttgtgtg   27900
taatttgaag gaggcggtcc cttagctgtg tttacactgt acttttaaat gtggggctga   27960
aggtagaatc aaccatactt aagatgccac ctgggaaaat agggttctgt gtcatctcag   28020
ccccacccat ttgcaaatga cttaacagca gcactattag ggttcctagt gtgagtcatt   28080
tgcatttgga ctggtgaact tggtgacttc ttggtgtttg gaaacaaaca acctttgcag   28140
tctttcgtaa aaagcctgaa cagtggacca gtctccagtt ctacttgcaa agctgcccc    28200 atcaaatccc tcataatgtt caacttaaaa aatgttacac ttttctctgg aaatctaacc   28260
ttttttcctt ttttaaaagc catttaagt acttcagtct tgaatcaaat gatcccaaat    28320
attggacacc aacctagaaa ttgggttacc tcctgggaac tttatcgaag aagagagatt   28380
ttggttggag agggggtttt gatgtttgat acttatattt actattttaa tatttcattg   28440
ttgttgttgc tgctgctgct gtattatttt gcgagtttcg tttgtttaaa tttcatggta   28500
tttggtagga gagagctgga tctgttggtt tcaggacaag tctagaaata agaaatctgc   28560
cttgagtgag tgagttggtt ccctctgttg ctatttcacc attaaggacg aaaggaactc   28620
acaaggacca gagacatctg gctgaaagca atactagtgt gactggacat ctactacctg   28680
ccatagttgg tcatatcgtt tccagtatga ttctgattga gtgagtgata ttaggctatg   28740
ttcagggatc agggaggcta attatgctta tattgccttg tagcatttg gtaagaatta    28800
```

```
atgattgtgt agatgtccag atttaggtca gcaatattct aaaagttctc attgaactaa    28860
tcatgtttat aagtagcctg tactttctat cataataaca atagtggaaa agctagttga    28920
cataaaagga gcccagattt tacttaagta aaaacacaaa agcaaagata ttttcccaca    28980
taaattacaa aagcaaagat attttcccac ataaatgtcc ccataaaaca agttgaacca    29040
aagaggaaag atgacaggta accgtatgac acgctaagaa agtatcataa tacttaagtt    29100
aacttcaacc ttttatttcc ttatcctaag cagcctcttt tctctttatc atttagtcct    29160
gtgcttctca actttgataa gtaaaaaagt tattgcacta aataaatctt attgaaatgc    29220
aggatctgat tgagtgggtg gggtaggtgg aatgagggtg gggaagttga gattctgcat    29280
ttcttagaag tttctacttt atgttaaaat ggctaatcca tctcaacatt gagaagtaag    29340
gtttcactta atttcagcct gtgtaagttt atcccatatg tacatttcct aaaactctaa    29400
tctcaggccc caggaatttc tcctttagtt aaaatatttt taggaataaa tttgaattgc    29460
attaatacac aatttataaa tttaacacaa aaaattattt gaagtttgag actttaggtt    29520
gcatgaaatc aatttcatac ttgaaaattt tctataaatt caaaagtctg tgtatttaaa    29580
tacaattaa atacctgtgt tacagtgaca tttgtttttc tgtctctctc tccaccattt    29640
ccagagtcat catccctgta cagaaaaatt tttcccacat gatttcacca taaattcatt    29700
aaatatgatg cttacttgat aatttctcca ggttctttt tttttaatt atactttaag    29760
ttctagggta catgtgcaca acctgcaggt ttgttacata tgtatacatg tgccatgttg    29820
gtgtgctgca cccattaact cgtcatttac attaggtata tctcctaatg ctatccctcc    29880
cccctacccc tactccatga caggtcccag tgtgtgatgt tccccaccct gtgtccaagt    29940
gttctcattg ttcagttccc acctatgagt gagaacatgc ggtgtttggt tttctgtcct    30000
tgcgatagtt tgctcagaat gatgtccttg ctcactgatg gacatttggt tggctccaag    30060
tatttgctat tgtaaatagt gccgcaataa acatacgtgt gcatgtgtct ttatagtagc    30120
atgatttata atcctctggg tatataccca gtaatgggat ggctggctca aatggtattt    30180
ctagttctag atcctagagg aatcgccaca ctgtcttcca caatgtttga actagtttac    30240
agtcccatca acagtgtaaa agtgttccta tttctctaca tcctttccag cacctgttgt    30300
ttccggactt taatgatcgc cattctaact ggtgtgagat ggtatctcat tgtggttttg    30360
atttgcattt ctctgatggc cagtgatgat gagcattttt tcatgtgtct tttggctaca    30420
taaatgtctt cttttgagaa gtgtctgttc atatccttca cccactttt gatggggtca    30480
tttgattttt tcttgtaaat ttgttaagt tcttttagat tctggatatt agccctttgt    30540
cagatgggta gattgtaaaa attttctccc attccgtagg tttcctattc actctgatgg    30600
tagtttcttt tgctgtgcag aagctcttta gtttaattag atcccatttg tcaatttgg    30660
cttttgttgc cattgctttt ggtgttttag tcatgaagtc cttgtccatg cctatgtcct    30720
gaatggtatt gcctaggttt tcttctaggg tttttatggt tttaggtcta acgtgtaagt    30780
ctttaattca tcttgaatta atttttgtat aaggtgtaaa gaagggatcc agtttcagct    30840
ttctacatat ggctagccag ttttcccagc accatttatt aaatagagaa tcctttcccc    30900
atttcttgtt tttgtcaggt ttgtcaaaga tcagatggt gtagatgtgt ggtattgttt    30960
ctgagggctc tgttctgttc cattggtcta tatctctgtt ttggtaccag taccatgctg    31020
ttttggttac tgtagccttg taatatagtt tgaagtcagg tagcgtgatg cctccagctt    31080
tgttcttttg gtttaggatt gtcttggcga tgcgggctct ttttggttc catatgaact    31140
```

```
ttaaagtagt ttttttccaa ttctgtggag aaagtcattg gtagcttgat ggggatggca   31200
ttgaatctat aaattacctt gggtagtatg gccattttca tgatattgat tcttcctacc   31260
catgagaatg gaatgttctt ccatttgttt gcgtcctctt ttatttcctt gagcagtggt   31320
ttgtagttct ccttgaagag gtcttccaca tcccttgtaa gttggattcc taagtatttt   31380
attctctttg aaacaattgt gaatgggagt tcactcatga tttggctctc tgtttgtctg   31440
ttattggtgt ataggaatgc ttgtgatttt tgcacattga ttttgtatcc tgagactttg   31500
ctgaagttgc ttatcagctt aaggagattt tgggctgaga tgatggggtt ttctaaatat   31560
acaatcatgt catctgcaaa cagagacaat ttgacttcct ctcttcctat ttgaatatcc   31620
tttatttctt tctattgcct gattgccctg gctagaacgt ccaatactat gttgaatagg   31680
agtggtgaca gaggacatcc ttgttttgtg ccagttttca aagggaatgc ttccagcttt   31740
tgcccattca gtatgacatt ggctgtgggt ttgtcgtgaa tagctcttat tattttgaga   31800
tatgtcccat caatacctag tttatttaga gttttttagca caaaggctgt tgaattttgt   31860
caaaggcctt ttctgcatct attgagataa tcatggtttt tgtctttgat tctgtttata   31920
tgatggatta tatttattga tttgcatatg ttgaaccagc cttgcatccc agggatgaag   31980
ccaacttgat catggtggat aagcttttg atgttctgct ggattcggtt tgccagtatt   32040
ttactgagga ttttttccatc gatcttcatc agggatattg gcctgaaatt ctcttttttt   32100
gttgtgtctc tgtcaggctg tggtatcagg atgatgctgg cctcataaaa tgagttaggg   32160
aggattccct ctttttctat tgattagaat agtttcagaa tggtaccagc tcctccttat   32220
acctctggta gaattcagct gtgaatccat ctggtcctga tggattttt tggttggtag   32280
gctattaatt attgcctcaa tttcagagcc tgttattggt ctattaagag attcaacttc   32340
ttcctggttt agtcctggga gggtgtgtgt gtccaggaat ttataaattt cttttaggtt   32400
ttctagttta tttgcataga agtgtttata gtgttctctg atggtagttt gtatttctgt   32460
gggattggtg gtgatatccc ctttatcacc ttttattgca tctatttgat tcttttctct   32520
tttcttcttt attagtcttg ctagtgatct atcaattttg ttgatctttt taaaaaacca   32580
gctcctgggt tcattgattt tttgaaggag ttttttctgtc tctatctcct tcagttctac   32640
tctgatctta gttatttctt gtcttctgct agcttttgaa tgtgtttgct cttgcttctc   32700
taaattgtga tgttagggtg tcaattttag atctttcctg cttttctcttg tgggcattta   32760
gtgctataaa tttccctcta cacactgctt taaatgtgtc ccagagattc tggtatgttg   32820
tgtctttgtt ctcattggtt tcaaagaaca tctttatttc tgccttcact tcgttaagta   32880
cccagtagtc actcaggagc aggttgctca gtttccatgt agttgagtgg ttctgagtga   32940
gtttcttaat cctgagttct agtttgaaag cactgtagtc tgagaggcag tttgttataa   33000
tttctgttct tttacatttg ctgaggagtg ctttacttcc aactatgtag tcaattttg   33060
gaataagtgt gatgtggtgc cgagaagaat gtatattctg ttgatttgga gtggagagtt   33120
ctgtagatgt ctattaggtc cgcttggtgc agagctgagt tcaatttctg gatatctttg   33180
ttaattttct gtcttgttga tctgtctaat attgaccgtg gggtgataaa gtctcccatt   33240
attattgtgt gggagtctaa gtctcttttgt aggtctctaa ggacttgctt tgtgaatctg   33300
gtgctcctgt attaggtgca tatatttta ggatagttag ctcttcttgt tgaattgatc   33360
cctttatcat tatgtaatgg ccttcttttgt ctctttgat ctttgttggt ttaaagtctg   33420
ttttatcaga gactaggatt gcaactcctg ctttttttg ctttccattt ccttggtaga   33480
tcttcctcca tcccttatt ttgagcctat gtgcgtctct gcacatgaga tgggtctgct   33540
```

```
gaatacagca cactgatggg tcttgactct ttatccaatt tgccagtcca tgtcttttaa    33600
ctggagcatt tagcccattt acatttaagg ttaatattgt tatgtgtgaa tttgatcctg    33660
tcattatgat gttagctggt tattttgctc gttagttgat gcagtttctt cctagcctca    33720
atgatcttta caatttggca tgttttgca gtggctggta ctggttgttc ctttccatgt    33780
ttagtgcttc cttcaggagc tcttgtaagg caggcctggt ggtgacaaaa tctctcagca    33840
tttgcttgtc tgtaaaggat tttatttctc cttcacttat gaagcttagt ttggctggat    33900
atgaaattct gggttgaaaa ttcttttctt taagaatgtt gaatattggc ccccactctc    33960
ttctggcttg tagagtttct gccgaaagat gctgttagtc tgatggactt cccttttgtgg   34020
gtaacctgcc ctttctctct cgctgcactt aatgtttttt ccttcatttc aactttggtg    34080
aatctgacaa ttatgtgtct ttgagttact cttcttgagg agtatctttg cggcattctc    34140
tgtatttcct gaatttgaat gctggcctgc ctcactagat tggggaagtt ctcctggata    34200
atatcctgca gagcgttttc caacttggtt ccattctccc catcactttc aggtacacca    34260
atcagatgta gatttggtct tttcacatag tcccatattt cttggaggct ttgttcattt    34320
cttttttactc tttttttctct aaacttctct tcttgcttca tttcattcat ttgatcttca   34380
atcccttttct tccacttgat tgaatcagct actgaagctt gtgcatgtgt cacatagttc    34440
tcgtgccatg gttttcagct ccatcaggtc atttaaggtc ttctctatgc tgttttttct    34500
agttagccat tcgtctaatg tttttttcaag gttttttagct tcttttgctaa aaggttcaaa  34560
catcctcctt tagctcggag gagtttgtta ttactgatca tctgaagcct tcttctctca    34620
acttgtgaaa gtcattctct gtccagcttt gttccattgc tggcgaggag ctgcattcct    34680
ttggaggaga agacgtgctc tgattttttag aattttcagc ttctctgctc tggtttctcc    34740
ccatcttatt ggttttatct accttttggtc tttgatgatg gtgacgtaca gatggggttt    34800
tggtgtggat gttctttctc tttgttagtt ttccttctaa cagtcaggac cctcagctgc    34860
aggtctgttg gagtttgctg gaggtccact ccagaccctg tttgcttggg tatcaccagc    34920
agaggctgca gaacagcaaa tattgcagaa cggcaaatgt tgctccctga ttgttcctct    34980
ggaagcttcg tctcagaggg gcacctggcc gtatgaggtg tcagtcggcc cctactggga    35040
ggtgcctccc agttaggcta ctcaggggtc aggaacccac ttgaagaggc agactgtcca    35100
ttctcagata tcatattcca tgctgggagg accccctactc ttttcaaagc tgtcagacag    35160
ggacatttaa gtctgcagaa gtttctgctg tcttttgttc agctgtgccc tgcccctaga    35220
ggtggagtct acagaggcag gcaggcctcc ttgagctgcg gtgggctcca cccatttcga    35280
gcttcctggc tgctttgttt acctactcaa gtctcagcaa tggtggacac ccctccccca    35340
gcctcgctgc tgctttgcag ttcgatctca gactgctgtg ctagcagtga gccaggctcc    35400
gtgggcatgg gaccctccga gccaggcctg ggacataatc tcctggtgtg ccgtttgcta    35460
agaccattgg aaaagcacag tattagggtg gggagtgtcc tgattttcca ggtaccgtca    35520
gtcatggctt cccttggcta ggaaagggaa ttccccaacc ccttgtgctt cctgggtgag    35580
gtgatgcccc accctgcttt ggctcatgct ccgtggggttg tacccactgt ctgacaagcc    35640
ccagtgagat gaacccggta cctcagttgg aaatgcagaa atcacccgtc ttctgcatca    35700
ctcacgctgg gggctgtaga ctggagctgt tcatatttgg ccatcttgga acctcccttt    35760
ccaagttctt tattacagag tgggtcactg aaacttcatg gaacaaattg gaaattatct    35820
tcttaattaa tgtcactgtc taccatgtat gggaatttgg taaatattat atggtttcaa    35880
```

```
taacatagta gatagaacat tgtcaaatct aaacttcagt gaattgtaac agatcccacc    35940
tgaaattcta aagaaaacag aattctaatt gaagaggtta aacttttaca gggaatgtca    36000
actgccattt gggtcctgta aacaaaaaac tgttttttaa aaagtaaac tttaaaagta    36060 ttttcagatg acctcatttg ctatccaagt ggcttgagta tgcttgatgc taagacttct    36120
ttgttacaga ctggagatgt gtgctactgg ggcagtgttg ctctgtgaca aggaggcaga    36180
ggatgagggc aaggttcgat gtgactgtga attctgggtg gctctggcta tcgggagcct    36240
tcattgatta cagcaaaaca gttgctttcc tagggcaata gtgtctctgt cacccaggct    36300
ggagttcagt ggcatgatca atcgctcact gtagcctcaa cttcttagac tcaagtaatc    36360
ctcccacctc agcctcccaa gtagctgaaa ctacaggtgt gcaccaccac acctaatttt    36420
tttaattttt aagttttttgt agagacatgg tctcactgtg ttgcccaggt tgatctcgaa    36480
ttcctgggct ctagtgatcc tcccgcctcg gcctcccaaa gtgttgggat tacaaatgtg    36540
agccactgca cctggccctt tgcaaccttc ttgacaatgc attcctttat tccctaactg    36600
gaagtaactt ctttctcttt ataaaattgt atctgtacct tttctgggtc atttctacct    36660
ttatattcta gttacgtatg tcctacctcc ctcctaggga gggaggtaag taagactgga    36720
aagtagactt catgtgtgat gaatgaatga acaaaaggga gtctaacata tggatatagt    36780
caactggatg caaattaaaa atttttaaat attgatttgc aagatttcat taaggtcaac    36840
tcttaatagt ttgtatcata tatgttagga accaaatatt aataacttct tcagcattac    36900
cattatcttt ataggactgt ctaaaatgag cagccatatc tttaaactgt gttttctctg    36960
attacacgct cacaggtaaa acccaaaggg gctgggaaca aacaagactt ttttttttt    37020 ctgtatgcct gaattatctg tactgttgct tgttttccca cctttggcca tagaaactta    37080
gttctaacat gctacaattt ttgcagttct ttctcttaga aaaagaccac attgtctgaa    37140
atttcatcca tttaagtaat caagccttaa agttgaagga tcttggtcat gattaatcta    37200
gacctacaaa gtagtatctt aatggcactc cttttagaaa gttaggttcc aggacacaca    37260
tagctgcagt gtccacattt tgtaagctcc ttcgttgtca cagccactct cttctctgtg    37320
gctgatattc taaaactggc aacacatcct gatggtaaaa gcttggttca ggagacaggt    37380
gacctactag ctttatggca tttgacaggt tacctaacct ctctgacgca taattgcctc    37440
atctatataa tggggataat aatacccatc ctgtctcctt gtaaaaatca aattagatga    37500
cgcctgtgaa tgttctatag tctcttagac aaatgtaagt tatgactaca gcaagagtaa    37560
aagagcatgt tgttatggac attctttcag tgaaatgtct aagacttgtg agtcacactt    37620
aaagctaaac ttgatatcta cttcattgat tttcttttta gttctatgta ctatattgaa    37680
tttcctgaca gtggggctat gaaagccttc ctagcatttt atagatgtgg ttgaattaat    37740
ggctgtaagc cttaaagcag aattagacag catcaatgaa tttattaagt ataaataaat    37800
atataatctg cttagcaata ttacacagcc tctttatctt atgtgtgata aagagtcatc    37860
cgaaggttga aaatgaagaa ttgtcctgga agctcttact taatctttta ttatttccta    37920
atacagtata taaaattact cattgaaagc ttagcagaat aagaaacaag aagttaaaag    37980
gctgaaaact acaaattttg ctattattat tgttattact tcccaagtct cttattgatc    38040
tgttagaaat agagctacac aggaaattgt aggacagtta gtatgtggta gtgttatctg    38100 cttttttaatt attcaagtaa ggtttttattc cattagagga actcaagaag ttggtcatgg    38160
ctgataattg ctatctgtca aattccttag agcagggatc cgcaacaccc aggccatgga    38220
ttgttaccag tccctggcct gttaggaacc aggctgcaca gtaggaagtg agcggcgggt    38280
```

```
gagcaaacat tgccatctga gctctgtctc ctttcagatc agcagcagca ttagattctc    38340
atagaagcat gagccctgtt gtgaactgca catgcaaggg atctaggttg tgtgctcctt    38400
atgagaatcc aattccttat gataatttaa ctgatgatct aaggtggaac catttcatcc    38460
caaaaccatc caccctgcta ctcccagacc gtggaaaaat tgtcttccac aaaactggtt    38520
cctgctgcca aaaaggttgg gaccactgcc ttagagttta aatttgggg ttagcacagc    38580 ctatatttac ctgagaattt caatgggttc actgatcttt ccaaatgaaa aggcttctta    38640
cgaaaattat atccaaactg tcttttctct tagtttaata aacctatcag taagttttta    38700
ctgagtactg ctattacatt tttctctgtt aagcattatg ggggctcaga catgatccat    38760
tccctcaaag aacttaccttt tcagctgaag actgactaga atgagcaaat acggttaaca    38820
attaacaagt gagtaggcca gctcggccaa catggtgaaa ccctgtctct actaaaaata    38880
caaaaattag ccgggcatgg tggtgggcgc ctgtaatccc agctacctcc tgctgaggca    38940
ggagaattgc ttgaacccag gaggtggaga ttgcagtgag ccgagattgc accattgcac    39000
tccagcctgg gcgacagagc aagactctgt cttgggaaaa aaacaaaaca aaacaagtga    39060
gaagggaatc aagtactacg taagatgtaa tgtggaattt tagggaagga aggcagtgta    39120
tgctggagta attagagaaa ggggcatgca tgatttgatg cttgaactgg atcatgaagg    39180
ataagcaaga ttttggcagc aagtgagagg gagagaggag tttgtcagag gaatggaaca    39240
agtcaggagg cagtaatgtg tacggcactc caaggactct gtcctgatcg gagcagaagt    39300
gatgaagcat tgagtagttt gagaaagtta gctaagaagg gtgagggcag atgttggaga    39360
gagttgagta tcagagagaa gacattagat ttgagcagat agaacaaaaa tgccattgcc    39420 agttttttgtg taagagaata gtattagggt ggttacccag gaagtggtca tcagagttga    39480
atggagcaga aagagtgtct gatacagcat cgggacgttg tggtcacaaa atgaggtggt    39540
gagggctgag ccaagatggt ggcagtggga tggataaaaa gggatggcca ggacaaaatat   39600 tttaaaggaa aaattaacag gacatcttta ctgactggat tggaaggcta tgcaggaaat    39660
atattgtcaa acttgattcc aggatttcta tcctatgcct gggttgccca aaatatcagg    39720
gaaccattgt tagaaaaggt aggagatacc actgttccaa caaaaagtat tgagtttggt    39780
gttgcaccca cttaacttca aggccttaca agtgagtaga cagttagtta gaattgcaga    39840
agtgccactc agagagcagg gcttgcaatg tggggttgga ctttgtcacc attgtgttaa    39900
ttcctaattc tatgcagatg ctcagcttga ggaatacccca tgtttgggct tcagaatgaa    39960
agccaagtaa tatttactca gatgccaatt ttccctctga aatatttgct catggaactg    40020
agagaacaat atataaagca ttaattattt ttctcataaa gttattaata aaaagataag    40080
atcagtgaaa ggcagagtaa actagaagcc aagtatagaa aatggtatca ttcaaagact    40140
cattactgta gtggtgaaaa caaaacaatt ttccaacagc ttaagatgcc tcagtatttt    40200
ggaccatttt taagtagtta gtgtgggcac ttagtaaaata tgtattaaac tatagttcat    40260
taattctttt ttttttttt ttgagatgga gtttcactct ggtcacccag gctgcatttt    40320
tgctttctta gtgatatata aaatgtcgag tttcacaatg atggtatctt agatttgatt    40380
aaatatggta ttaaaaaata gctgatcaca gaaagtctct accagtgtga tgtagatggc    40440
taaagtattc cacatttgca aacttttatt gacctaaata agaggtgccc cttgggttgt    40500
ttttatttgg actgggaata ttaggagaaa gcttttttcat tcagtgtgta agtacaatct    40560
accagaaata gaaaccccca tggacgatct atttctttga tggtacagga ctcagaacat    40620
```

```
tcacaaagat ttagttgtta gcggaataga catctgtatt ttattcaaac caatttttccc    40680 ttcctaatct gagaacattg tgcaatctaa gcagttctaa gcatgtttgc tattcgtgca    40740
aagtgagagt aaatctaaaa gaaattttt tgtgtgttta gggatggtaa taaagtctct    40800
tagtggttga aaatgttatt tcttacaaaa gtggagaaca tttgcttttc aataccagag    40860
ttttcagcca tttctgcatt ctgacctatt gactggaggt aggttgcctt tgaattcagt    40920
aaaacttcat gggcagaaac acagttcctt ttcctactta tttggatatc atgatggcca    40980
ttgcatgtat gtgtcttttt gtaagtccat gcctcagaac tgagaagtag gaataaaatt    41040
agggtcaggg ctggggatgc tactctttgc tgctgagaaa cacaatgctt caggtaagtg    41100
attctgaagt ccttcaccac ctgacggtaa ccttgggttg gtccataggt atgttttcat    41160
tttgcttgtt catccatttt aattggcttc ctagagcatg cttgtagatg tagagccaaa    41220
tttagagtag agcaaccctc tggcaaacag gaagagatta attttgtggt atgcttttaa    41280
gggacttccc aggaaacttc aaaagcagaa aagaagcac tagctgccta ttccaaaatg    41340
tgtaaaacac cactcagctt tttaaaagta ggataaactc agagcgcgcg cacacgcgcg    41400
cgcgcacaca cacacacaca cacagagaga acatctctag taaaaagaaa agttgagctt    41460
tcttagctag atgtgtgtat tagccagaaa aagccaagga gtgaagggtt ttagagaact    41520
ggaggagata aagtggagtc tgcatatggg aggcatttga aatggactta aatgtctttt    41580
taatgctgac ttttttcagtt ttctccttac cagacacatt gttttcatga cattagcccc    41640
aggcatagac acatcattaa aatgaacatg tcaaaaaatg atttctgttt agaaataagc    41700
aaaacatttt cagttgtgac cacccaggtg tagaataaag aacagtggaa ttgggagccc    41760
tgagttctaa cataaacttt cttcatgaca taaggcaagt cttctatggc ctttggtttc    41820
cttacctgta aaacaggatg gctcaatgaa attatctttc ttctttgcta taatagagta    41880
tctctgtggg aagaggaaaa aaaaagtcaa tttaaaggct ccttatagtt ccccaactgc    41940
tgttttattg tgctattcat gcctagacat cacatagcta gaaaggccca tcagaccccct    42000 caggccactg ctgttcctgt cacacattcc tgcaaaggac catgttgcta acttgaaaaa    42060
aattactatt aattacactt gcagttgttg cttagtaaca tttatgattt tgtgtttctc    42120
gtgacagcat gagcagagat cattaaaaat taaacttaca aagctgctaa agtgggaaga    42180
aggagaactt gaagccacaa ttttttgcact tgcttagaag ccatctaatc tcaggttttat    42240 atgctagatc ttgggggaaa cactgcatgt ctctggttta tattaaacca catacagcac    42300
actactgaca ctgatttgtg tctggtgcag ctggagttta tcaccaagac ataaaaaaac    42360
cttgaccctg cagaatggcc tggaattaca atcagatggg ccacatggca tcccggtgaa    42420
agaaagccct aaccagtttt ctgtcttgtt tctgctttct ccctacagtt ccaccaggtg    42480
agaagagtga tgaccatcct tttccttact atggttattt catactttgg ttgcatgaag    42540
gctgccccca tgaaagaagc aaacatccga ggacaaggtg gcttggccta cccaggtgtg    42600
cggacccatg ggactctgga gagcgtgaat gggcccaagg caggttcaag aggcttgaca    42660
tcattggctg acactttcga acacgtgata gaagagctgt tggatgagga ccagaaagtt    42720
cggcccaatg aagaaacaa taaggacgca gacttgtaca cgtccagggt gatgctcagt    42780
agtcaagtgc ctttggagcc tcctcttctc tttctgctgg aggaatacaa aaattaccta    42840
gatgctgcaa acatgtccat gagggtccgg cgccactctg accctgcccg ccgagggggag    42900 ctgagcgtgt gtgacagtat tagtgagtgg gtaacggcag cagacaaaaa gactgcagtg    42960
gacatgtcgg gcgggacggt cacagtcctt gaaaaggtcc ctgtatcaaa aggccaactg    43020
```

```
aagcaatact tctacgagac caagtgcaat cccatgggtt acacaaaaga aggctgcagg   43080
ggcatagaca aaaggcattg gaactcccag tgccgaacta cccagtcgta cgtgcgggcc   43140
cttaccatgg atagcaaaaa gagaattggc tggcgattca taaggataga cacttcttgt   43200
gtatgtacat tgaccattaa aaggggaaga tagtggattt atgttgtata gattagatta   43260
tattgagaca aaaattatct atttgtatat atacataaca gggtaaatta ttcagttaag   43320
aaaaaaataa ttttatgaac tgcatgtata aatgaagttt atacagtaca gtggttctac   43380
aatctattta ttggacatgt ccatgaccag aagggaaaca gtcatttgcg cacaacttaa   43440
aaagtctgca ttcattcct tgataatgtt gtggtttgtt gccgttgcca agaactgaaa    43500
acataaaaag ttaaaaaaaa taataaattg catgctgctt taattgtgaa ttgataataa   43560
actgtcctct ttcagaaaac agaaaaaaaa cacacacaca cacaacaaaa atttgaacca   43620
aaacattccg tttacatttt agacagtaag tatcttcgtt cttgttagta ctatatctgt   43680
tttactgctt ttaacttctg atagcgttgg aattaaaaca atgtcaaggt gctgttgtca   43740
ttgctttact ggcttagggg atggggatg ggggtatat ttttgtttgt tttgtgtttt     43800
tttttcgttt gtttgttttg ttttttagtt cccacaggga gtagagatgg ggaaagaatt   43860
cctacaatat atattctggc tgataaaaga tacatttgta tgttgtgaag atgtttgcaa   43920
tatcgatcag atgactagaa agtgaataaa aattaaggca actgaacaaa aaaatgctca   43980
cactccacat cccgtgatgc acctcccagg ccccgctcat tctttgggcg ttggtcagag   44040
taagctgctt ttgacggaag gacctatgtt tgctcagaac acattctttc ccccctccc    44100 cctctggtct cctctttgtt ttgttttaag gaagaaaaat cagttgcgcg ttctgaaata   44160
ttttaccact gctgtgaaca agtgaacaca ttgtgtcaca tcatgacact cgtataagca   44220
tggagaacag tgatttttt ttagaacaga aaacaacaaa aaataacccc aaaatgaaga    44280 ttattttta tgaggagtga acatttgggt aaatcatggc taagcttaaa aaaaactcat    44340
ggtgaggctt aacaatgtct tgtaagcaaa aggtagagcc ctgtatcaac ccagaaacac   44400
ctagatcaga acaggaatcc acattgccag tgacatgaga ctgaacagcc aaatggaggc   44460
tatgtggagt tggcattgca tttaccggca gtgcgggagg aatttctgag tggccatccc   44520
aaggtctagg tggaggtggg gcatggtatt tgagacattc caaaacgaag gcctctgaag   44580
gacccttcag aggtggctct ggaatgacat gtgtcaagct gcttggacct cgtgctttaa   44640
gtgcctacat tatctaactg tgctcaagag gttctcgact ggaggaccac actcaagccg   44700
acttatgccc accatcccac ctctggataa ttttgcataa aattggatta gcctggagca   44760
ggttgggagc caaatgtggc atttgtgatc atgagattga tgcaatgaga tagaagatgt   44820
ttgctacctg aacacttatt gctttgaaac tagacttgag gaaaccaggg tttatctttt   44880
gagaactttt ggtaagggaa aagggaacag gaaaagaaac cccaaactca ggccgaatga   44940
tcaaggggac ccataggaaa tcttgtccag agacaagact tcgggaaggt gtctggacat   45000
tcagaacacc aagacttgaa ggtgccttgc tcaatggaag aggccaggac agagctgaca   45060
aaattttgct ccccagtgaa ggccacagca accttctgcc catcctgtct gttcatggag   45120
agggtccctg cctcacctct gccatttggg gttaggagaa gtcaagttgg gagcctgaaa   45180
tagtggttct tggaaaaatg gatccccagt gaaaactaga gctctaagcc cattcagccc   45240
atttcacacc tgaaaatgtt agtgatcacc acttggacca gcatccttaa gtatcagaaa   45300
gccccaagca attgctgcat cttagtaggg tgagggataa gcaaagagg atgttcacca    45360
```

```
taacccagga atgaagatac catcagcaaa gaatttcaat ttgttcagtc tttcatttag    45420
agctagtctt tcacagtacc atctgaatac ctctttgaaa gaaggaagac tttacgtagt    45480
gtagatttgt tttgtgttgt ttgaaaatat tatctttgta attattttta atatgtaagg    45540
aatgcttgga atatctgctg tatgtcaact ttatgcagct tccttttgag ggacaaattt    45600
aaaacaaaca acccccatc  acaaacttaa aggattgcaa gggccagatc tgttaagtgg    45660
tttcatagga gacacatcca gcaattgtgt ggtcagtggc tcttttaccc aataagatac    45720
atcacagtca catgcttgat ggtttatgtt gacctaagat ttattttgtt aaaatctctc    45780
tctgttgtgt tcgttcttgt tctgttttgt tttgttttt  aaagtcttgc tgtggtctct    45840
ttgtggcaga agtgtttcat gcatggcagc aggcctgttg cttttttatg gcgattccca    45900
ttgaaaatgt aagtaaatgt ctgtggcctt gttctctcta tggtaaagat attattcacc    45960
atgtaaaaca aaaaacaata tttattgtat tttagtatat ttatataatt atgttattga    46020
aaaaaattgg cattaaaact taaccgcatc agaagcctat tgtaaataca agttctattt    46080
aagtgtacta attaacatat aatatatgtt ttaaatatag aattttttaat gtttttaaat    46140 atattttcaa agtacataa                                                  46159
```

TREATMENT OF BRAIN DERIVED NEUROTROPHIC FACTOR (BDNF) RELATED DISEASES BY INHIBITION OF NATURAL ANTISENSE TRANSCRIPT TO BDNF

CROSS REFERENCE

This application claims the benefit of U.S. Provisional Application No. 61/152,132 filed Feb. 12, 2009, which application is incorporated herein by reference in its entirety.

FIELD OF THE INVENTION

Embodiments of the invention comprise oligonucleotides modulating expression and/or function of BDNF and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an BDNF polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 3175 of SEQ ID NO: 2 (FIG. 3) thereby modulating function and/or expression of the BDNF polynucleotide in patient cells or tissues in vivo or in vitro.

In another preferred embodiment, an oligonucleotide targets a natural antisense sequence of BDNF polynucleotides, for example, nucleotides set forth in SEQ ID NO: 2, and any variants, alleles, homologs, mutants, derivatives, fragments and complementary sequences thereto. Examples of antisense oligonucleotides are set forth as SEQ ID NOS: 3 to 8 (FIG. 4).

Another embodiment provides a method of modulating function and/or expression of an BDNF polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the BDNF polynucleotide; thereby modulating function and/or expression of the BDNF polynucleotide in patient cells or tissues in vivo or in vitro.

Another embodiment provides a method of modulating function and/or expression of an BDNF polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an BDNF antisense polynucleotide; thereby modulating function and/or expression of the BDNF polynucleotide in patient cells or tissues in vivo or in vitro.

In a preferred embodiment, a composition comprises one or more antisense oligonucleotides which bind to sense and/or antisense BDNF polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 1 C: is a graph of real time PCR results showing the fold change+standard deviation in BDNF mRNA after treatment of CHP212 cells with LNA gapmer-phosphorothioate oligonucleotides introduced using Lipofectamine 2000, as compared to control. Real time PCR results show that the levels of the BDNF mRNA in CHP212 cells are significantly increased 48 h after treatment with two of the LNA gapmers with fully phosphothioated backbone designed to BDNF antisense NM_4170735. Bars denoted as CUR-0071, CUR-0072, and CUR-0076 correspond to samples treated with SEQ ID NOS: 6, 8and 4, respectively.

FIG. 2 shows SEQ ID NO: 1: *Homo sapiens* brain-derived neurotrophic factor (BDNF), transcript variant 1, mRNA, (NCBI Accession No.: NM_170735) and SEQ ID NO: 11 shows the genomic sequence of BDNF (exons are shown in capital letters, introns in small).

FIG. 3 shows SEQ ID NO: 2: Natural BDNF antisense sequence (NR_002832.1) *Homo sapiens* BDNF opposite strand (non-protein coding) (BDNFOS), non-coding RNA.

FIG. 4 shows the antisense oligonucleotides. SEQ ID NOS: 3 to 8. * indicates phosphothioate bond and + indicates LNA modification.

FIG. 5 shows SEQ ID NOS: 9 and 10.

DETAILED DESCRIPTION

Figure 1A:
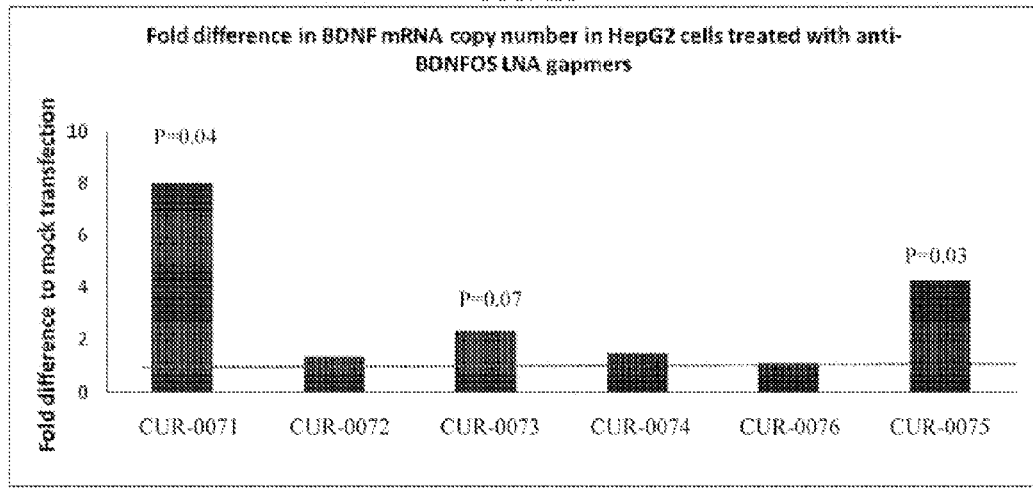
FIG. 1A is a graph of real time PCR results showing the fold change+standard deviation in BDNF mRNA after treatment of HepG2 cells with LNA gapmer phosphorothioate oligonucleotides introduced using Lipofectamine 2000, as compared to control. Real time PCR results show that the levels of the BDNF mRNA in HepG2 cells are significantly increased 48 h after treatment with two of the LNA gapmers with fully phosphothioated backbone designed to BDNF antisense NM_170735 (CUR-0071, P=0.04, CUR-0073, P=0.07, CUR-0075, P=0.03). Bars denoted as CUR-0071, CUR-0072, CUR-0073, CUR-0074, CUR-0075 and CUR-0076 correspond to samples treated with SEQ ID NOS: 6, 7, 8, 5, 4, 3 respectively.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced about one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) *Ann. Rev. Biochem.* 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Ho ögsteen or reverse Ho ögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "BDNF" and "Brain derived neurotrophic factor" are inclusive of all family members, mutants, alleles, fragments, species, coding and noncoding sequences, sense and antisense polynucleotide strands, etc.

As used herein, the words 'Brain derived neurotrophic factor', 'Brain-derived neurotrophic factor' and BDNF, are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N.J., et al. (2001) Proc. Natl. Acad. Sci. USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) Nature 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) Nature 409:363-366; Boutla, A., et al. (2001) Curr. Biol. 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) J. American. Med. Assoc. 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al. (1990) Cell, 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.,* 25(22), 4429-4443, Toulmé, J. J., (2001) *Nature Biotechnology* 19:17-18; Manoharan M., (1999) *Biochemica et Biophysica Acta* 1489:117-139; Freier S. M., (1997) *Nucleic Acid Research,* 25:4429-4443, Uhlman, E., (2000) *Drug Discovery & Development,* 3: 203-213, Herdewin P., (2000) *Antisense & Nucleic Acid Drug Dev.,* 10:297-310); 2'-O, 3'-C-linked [3.2.0]bicycloarabinonucleosides (see e.g. N. K Christiensen., et al, (1998) *J. Am. Chem. Soc.,* 120: 5458-5463; Prakash T P, Bhat B. (2007) *Curr Top Med. Chem.* 7(7):641-9; Cho E J, et al. (2009) *Annual Review of Analytical Chemistry,* 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) *J. Mol. Biol.*, 215, 403-410; Zhang and Madden, (1997) *Genome Res.*, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, the term "cancer" refers to any malignant tumor, particularly arising in the lung, kidney, or thyroid. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As noted above, the invention specifically permits differential diagnosis of lung, kidney, and thyroid tumors.

Polynucleotide and Oligonucleotide Compositions and Molecules

Targets: In one embodiment, the targets comprise nucleic acid sequences of Brain derived neurotrophic factor (BDNF), including without limitation sense and/or antisense noncoding and/or coding sequences associated with BDNF.

Neurotrophins are a class of structurally related growth factors that promote neural survival and differentiation. They stimulate neurite outgrowth, suggesting that they can promote regeneration of injured neurons, and act as target-derived neurotrophic factors to stimulate collateral sprouting in target tissues that produce the neurotrophin (Korsching., (1993) *J. Neurosci.*, 13: 2739). Brain-derived neurotrophic factor (BDNF) was initially characterized as a basic protein present in brain extracts and capable of increasing the survival of dorsal root ganglia (Leibrock., et al., (1989) *Nature,* 341:149). When axonal communication with the cell body is interrupted by injury, Schwann cells produce neurotrophic factors such as nerve growth factor (NGF) and BDNF. Neurotrophins are released from the Schwann cells and dispersed diffusely in gradient fashion around regenerating axons, which then extend distally along the neurotrophins' density gradient (Ide., (1996) *Neurosci. Res.,* 25:101). Local application of BDNF to transected nerves in neonatal rats has been shown to prevent massive death of motor neurons that follows axotomy (DiStefano., et al., (1992) *Neuron,* 8:983; Oppenheim., et al., (1992) *Nature,* 360:755; Yan., et al., (1992) *Nature,* 360:753). The mRNA titer of BDNF increases to several times the normal level four days after axotomy and reaches its maximum at 4 weeks (Meyer., et al., (1992) *J. Cell Biol.* 119:45). Moreover, BDNF has been reported to enhance the survival of cholinergic neurons in culture (Nonomura, et al., (1995) *Brain Res.* 683:129).

Exemplary Brain derived neurotrophic factor (BDNF) mediated diseases and disorders which can be treated with cell/tissues regenerated from stem cells obtained using the antisense compounds comprise: a disease or a disorder associated with defective neurogenesis; a neurodegenerative disease or disorder (e.g., Alzheimer's disease, Parkinson's disease, Huntington's disease, amyotrophic lateral sclerosis etc.); a neuropsychiatric disorder (depression, schizophrenia, schizofreniform disorder, schizoaffective disorder, and delusional disorder; anxiety disorders such as panic disorder, phobias (including agoraphobia), an obsessive-compulsive disorder, a posttraumatic stress disorder, a bipolar disorder, anorexia nervosa, bulimia nervosa, an autoimmune disorder (e.g., multiple sclerosis) of the central nervous system, memory loss, a long term or a short term memory disorder, benign forgetfulness, a childhood learning disorder, close head injury, an attention deficit disorder, neuronal reaction to viral infection, brain damage, narcolepsy, a sleep disorder (e.g., circadian rhythm disorders, insomnia and narcolepsy); severance of nerves or nerve damage, severance of cerebrospinal nerve cord (CNS) and a damage to brain or nerve cells, a neurological deficit associated with AIDS, a motor and tic disorder characterized by motor and/or vocal tics (e.g., Tourette's disorder, chronic motor or vocal tic disorder, transient tic disorder, and stereotypic movement disorder), a substance abuse disorder (e.g., substance dependence, substance abuse and the sequalae of substance abuse/dependence, such as substance-induced psychological disorder, substance withdrawal and substance-induced dementia or amnestic disorder), traumatic brain injury, tinnitus, neuralgia (e.g., trigeminal neuralgia) pain (e.g chronic pain, chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury, pain associated with drug intake and recurrent acute pain, neuropathic pain), inappropriate neuronal activity resulting in neurodysthesias in a disease such as diabetes, an MS and a motor neuron disease, ataxias, muscular rigidity (spasticity), temporomandibular joint dysfunction, Reward deficiency syndrome (RDS), neurotoxicity caused by alcohol or substance abuse (e.g., ecstacy, methamphetamine etc.), mental retardation or cognitive impairment (e.g., nonsyndromic X-linked mental retardation, fragile X syndrome, Down's syndrome, autism), aphasia, Bell's palsy, Creutzfeldt Jacob disease, encephalitis, age related macular degeneration, ondine syndrome, WAGR syndrome, hearing loss, Rett syndrome, epilepsy, spinal cord injury, stroke, hypoxia, ischemia, brain injury, optic nerve injury, diabetic neuropathy, peripheral neuropathy, nerve transplantation complications, motor neuron disease, peripheral nerve injury, obesity, a metabolic syndrome, cancer, asthma, an atopic disease, an allergic inflammation, eczema, a neuro-oncological disease or disorder, neuro-immunological disease or disorder and neuro-otological disease or disorder; and a disease or disorder associated with aging and senescence.

In a preferred embodiment, the oligonucleotides are specific for polynucleotides of BDNF, which includes, without limitation noncoding regions. The BDNF targets comprise variants of BDNF or BDNFOS; mutants of BDNF or BDNFOS, including SNPs; noncoding sequences of BDNF; alleles, fragments and the like. Preferably the oligonucleotide is an antisense RNA molecule.

In accordance with embodiments of the invention, the target nucleic acid molecule is not limited to BDNF polynucleotides alone but extends to any of the isoforms, receptors, homologs, non-coding regions and the like of BDNF.

In another preferred embodiment, an oligonucleotide targets a natural antisense sequence (natural antisense to the coding and non-coding regions) of BDNF targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of BDNF including without limitation, antisense sequences which are identified and expanded, using for example, PCR, hybridization etc., one or more of the sequences set forth as SEQ ID NO: 2, and the like, modulate the expression or function of BDNF. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 3 to 8 including antisense sequences which are identified and expanded, using for example, PCR, hybridization etc. These oligonucleotides can comprise one or more modified nucleotides, shorter or longer fragments, modified bonds and the like.

Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Brain derived neurotrophic factor (BDNF).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of Brain derived neurotrophic factor (BDNF) and modulate the expression and/or function of Brain derived neurotrophic factor (BDNF) (SEQ ID NO: 1). Examples of antisense sequences include SEQ ID NOS: 2 to 8.

In another preferred embodiment, the antisense oligonucleotides bind to one or more segments of Brain derived neurotrophic factor (BDNF) polynucleotides and modulate the expression and/or function of Brain derived neurotrophic factor (BDNF). The segments comprise at least five consecutive nucleotides of the Brain derived neurotrophic factor (BDNF) sense or antisense polynucleotides.

In another preferred embodiment, the antisense oligonucleotides are specific for natural antisense sequences of Brain derived neurotrophic factor (BDNF) wherein binding of the oligonucleotides to the natural antisense sequences of Brain derived neurotrophic factor (BDNF) modulate expression and/or function of Brain derived neurotrophic factor (BDNF).

In another preferred embodiment, oligonucleotide compounds comprise sequences set forth as SEQ ID NOS: 3 to 8, antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Brain derived neurotrophic factor (BDNF), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) *Science* 308 (5725), 1149-1154; Kapranov, P. et al. (2005). *Genome Res* 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Brain derived neurotrophic factor (BDNF) polynucleotides and encoded products thereof dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Brain derived neurotrophic factor (BDNF) polynucleotides. "Modulators" are those compounds that decrease or increase the expression of a nucleic acid molecule encoding Brain derived neurotrophic factor (BDNF) and which comprise at least a 5-nucleotide portion that is complementary to a preferred target segment. The screening method comprises the steps of contacting a preferred target segment of a nucleic acid molecule encoding sense or natural antisense polynucleotides of Brain derived neurotrophic factor (BDNF) with one or more candidate modulators, and selecting for one or more candidate modulators which decrease or increase the expression of a nucleic acid molecule encoding Brain derived neurotrophic factor (BDNF) polynucleotides, e.g. SEQ ID NOS: 3 to 8. Once it is shown that the candidate modulator or modulators are capable of modulating (e.g. either decreasing or increasing) the expression of a nucleic acid molecule encoding Brain derived neurotrophic factor (BDNF) polynucleotides, the modulator may then be employed in further investigative studies of the function of Brain derived neurotrophic factor (BDNF) polynucleotides, or for use as a research, diagnostic, or therapeutic agent in accordance with the present invention.

Targeting the natural antisense sequence preferably modulates the function of the target gene. For example, the BDNF gene (e.g. accession number NM_170735, FIG. 2). In a preferred embodiment, the target is an antisense polynucleotide of the BDNF gene. In a preferred embodiment, an antisense oligonucleotide targets sense and/or natural antisense sequences of Brain derived neurotrophic factor (BDNF) polynucleotides (e.g. accession number NM_170735, FIG. 2), variants, alleles, isoforms, homologs, mutants, derivatives, fragments and complementary sequences thereto. Preferably the oligonucleotide is an antisense molecule and the targets include coding and noncoding regions of antisense and/or sense BDNF polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., (1998) *Nature*, 391, 806-811; Timmons and Fire, (1998) *Nature*, 395, 854; Timmons et al., (2001) *Gene*, 263, 103-112; Tabara et al., (1998) *Science*, 282, 430-431; Montgomery et al., (1998) *Proc. Natl. Acad. Sci. USA*, 95, 15502-15507; Tuschl et al., (1999) *Genes Dev.*, 13, 3191-3197; Elbashir et al., (2001) *Nature*, 411, 494-498; Elbashir et al., (2001) *Genes Dev.* 15, 188-200). For example, such double-stranded moieties have been shown to inhibit the target by the classical hybridization of antisense strand of the duplex to the target, thereby triggering enzymatic degradation of the target (Tijsterman et al., (2002) *Science*, 295, 694-697).

In a preferred embodiment, an antisense oligonucleotide targets Brain derived neurotrophic factor (BDNF) polynucleotides (e.g. accession number NM_170735), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Brain derived neurotrophic factor (BDNF) alone but extends to any of the isoforms, receptors, homologs and the like of Brain derived neurotrophic factor (BDNF) molecules.

In another preferred embodiment, an oligonucleotide targets a natural antisense sequence of BDNF polynucleotides, for example, polynucleotides set forth as SEQ ID NO: 2, and any variants, alleles, homologs, mutants, derivatives, fragments and complementary sequences thereto. Examples of antisense oligonucleotides are set forth as SEQ ID NOS: 3 to 8.

In one embodiment, the oligonucleotides are complementary to or bind to nucleic acid sequences of Brain derived neurotrophic factor (BDNF) antisense, including without limitation noncoding sense and/or antisense sequences associated with Brain derived neurotrophic factor (BDNF) polynucleotides and modulate expression and/or function of Brain derived neurotrophic factor (BDNF) molecules.

In another preferred embodiment, the oligonucleotides are complementary to or bind to nucleic acid sequences of BDNF natural antisense, set forth as SEQ ID NO: 2 and modulate expression and/or function of BDNF molecules.

In a preferred embodiment, oligonucleotides comprise sequences of at least 5 consecutive nucleotides of SEQ ID NOS: 3 to 8 and modulate expression and/or function of Brain derived neurotrophic factor (BDNF) molecules.

The polynucleotide targets comprise BDNF, including family members thereof, variants of BDNF; mutants of BDNF, including SNPs; noncoding sequences of BDNF; alleles of BDNF; species variants, fragments and the like. Preferably the oligonucleotide is an antisense molecule.

In another preferred embodiment, the oligonucleotide targeting Brain derived neurotrophic factor (BDNF) polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of Brain derived neurotrophic factor (BDNF) polynucleotides, e.g. SEQ ID NO: 2, modulates the expression or function of these targets. In one embodiment, expression or function is up-regulated as compared to a control.

In another preferred embodiment, expression or function is down-regulated as compared to a control.

In another preferred embodiment, antisense compounds comprise sequences set forth as SEQ ID NOS: 3 to 8. These oligonucleotides can comprise one or more modified nucleotides, shorter or longer fragments, modified bonds and the like.

In another preferred embodiment, SEQ ID NOS: 3 to 8 comprise one or more LNA nucleotides.

Table 1 shows exemplary antisense oligonucleotides useful in the methods of the invention.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) *Proc. R. Soc. London*, B 205, 435) have been used to evolve new nucleic acid catalysts capable of catalyzing a variety of reactions, such as cleavage and ligation of phosphodiester linkages and amide linkages, (Joyce, (1989) *Gene*, 82, 83-87; Beaudry et al., (1992) *Science* 257, 635-641; Joyce, (1992) *Scientific American* 267, 90-97; Breaker et al., (1994) *TIBTECH* 12, 268; Bartel et al., (1993) *Science* 261:1411-1418; Szostak, (1993) *TIBS* 17, 89-93; Kumar et al., (1995) *FASEB J.*, 9, 1183; Breaker, (1996) *Curr. Op. Biotech.*, 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations

TABLE 1

| Sequence ID | Oligo Name | Sequence |
| --- | --- | --- |
| SEQ ID NO: 3 | CUR-0076 | C* + T* + T*G*A*A*T*T*G*T*T*T* + G* + T* + A |
| SEQ ID NO: 4 | CUR-0075 | A* + G* + T*T*G*C*A*A*G*A*G*T* + T* + G* + G |
| SEQ ID NO: 5 | CUR-0074 | A* + T* + C*T*G*T*T*C*T*G*C*T* + G* + T* + C |
| SEQ ID NO: 6 | CUR-0071 | C* + A* + T*A*T*T*C*T*T*G*G*A* + C* + G* + A |
| SEQ ID NO: 7 | CUR-0072 | T* + G* + T*G*C*T*G*T*T*G*T*A* + A* + G* + A |
| SEQ ID NO: 8 | CUR-0073 | T* + G* + A*C*A*G*A*G*G*A*G*T* + A* + T* + T |

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, *Nature* 429 1986; Cech, 260 *JAMA* 3030, 1988; and Jefferies et al., 17 *Nucleic Acids Research* 1371, 1989).

Because of their sequence-specificity, trans-cleaving enzymatic nucleic acid molecules show promise as therapeutic agents for human disease (Usman & McSwiggen, (1995) *Ann. Rep. Med. Chem.* 30, 285-294; Christoffersen and Marr, (1995) *J. Med. Chem.* 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) *Nature*, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) *Nature*, 334, 585; Walbot and Bruening, (1988) *Nature*, 334, 196; Uhlenbeck, O. C. (1987) *Nature*, 328: 596-600; Koizumi, M., et al. (1988) *FEBS Lett.*, 228: 228-230). This has allowed use of the catalytic RNA to cleave specific target sequences and indicates that catalytic RNAs designed according to the "hammerhead" model may possibly cleave specific substrate RNAs in vivo. (see Haseloff and Gerlach, (1988) *Nature*, 334, 585; Walbot and Bruening, (1988) *Nature*, 334, 196; Uhlenbeck, O. C. (1987) *Nature*, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) *Nat. Rev. Genet.*, 2, 110-119; Matzke et al., (2001) *Curr. Opin. Genet. Dev.*, 11, 221-227; Sharp, (2001) *Genes Dev.*, 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 2 to 8 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with BDNF and the sequences set forth as SEQ ID NOS: 1, 2. The oligonucleotides are also targeted to overlapping regions of SEQ ID NOS: 1, 2.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression.

RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) *Acc. Chem. Res.*, 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [known as a methylene(methylimino) or MMI backbone], CH2-O—N(CH3)-CH2, CH2-N (CH3)-N (CH3)-CH2 and O—N(CH3)-CH2-CH2 backbones, wherein the native phosphodiester backbone is represented as O—P—O—CH1). The amide backbones disclosed by De Mesmaeker et al. (1995) *Acc. Chem. Res.* 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen et al. (1991) *Science* 254, 1497). Oligonucleotides may also comprise one or more substituted sugar moieties. Preferred oligonucleotides comprise one of the following at the 2' position: OH, SH, SCH3, F, OCN, OCH3OCH3, OCH3O(CH2)n CH3, O(CH2)nNH2 or O(CH2)nCH3 where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2CH2OCH3, also known as 2'-O-(2-methoxyethyl)] (Martin et al., (1995) *Helv. Chim. Acta,* 78, 486). Other preferred modifications include 2'-methoxy (2'-O—CH3), 2'-propoxy (2'-OCH2CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp 75-77; Gebeyehu, G., (1987) et al. *Nucl. Acids Res.* 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., (1989) *Proc. Natl. Acad. Sci. USA* 86, 6553), cholic acid (Manoharan et al. (1994) *Bioorg. Med. Chem. Let.* 4, 1053), a thioether, e.g., hexyl-5-tritylthiol (Manoharan et al. (1992) *Ann. N.Y. Acad. Sci.* 660, 306; Manoharan et al. (1993) *Bioorg. Med. Chem. Let.* 3, 2765), a thiocholesterol (Oberhauser et al., (1992) *Nucl. Acids Res.* 20, 533), an aliphatic chain, e.g., dodecandiol or undecyl residues (Saison-Behmoaras et al. *EMBO J.* 1991, 10, 111; Kabanov et al. (1990) *FEBS Lett.* 259, 327; Svinarchuk et al. (1993) *Biochimie* 75, 49), a phospholipid, e.g., di-hexadecyl-rac-glycerol or triethylammonium 1,2-di-O-hexadecyl-rac-glycero-3-H-phosphonate (Manoharan et al. (1995) *Tetrahedron Lett.* 36, 3651; Shea et al. (1990) *Nucl. Acids Res.* 18, 3777), a polyamine or a polyethylene glycol chain (Manoharan et al. (1995) *Nucleosides & Nucleotides,* 14, 969), or adamantane acetic acid (Manoharan et al. (1995) *Tetrahedron Lett.* 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) *Current Opinions in Drug Discovery & Development* Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) Science 254, 1497-1500.

In another preferred embodiment of the invention the oligonucleotides with phosphorothioate backbones and oligonucleosides with heteroatom backbones, and in particular —CH2-NH—O—CH2-, —CH2-N(CH3)-O—CH2— known as a methylene (methylimino) or MMI backbone, —CH2-O—N(CH3)-CH2—, —CH2N(CH3)-N(CH3) CH2— and —O—N(CH3)-CH2—CH2— wherein the native phosphodiester backbone is represented as —O—P—O—CH2— of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S-or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are O(CH2) nOmCH3, O(CH2)n, OCH3, O(CH2)nNH2, O(CH2)nCH3, O(CH2)nONH2, and O(CH2nON(CH2)nCH3)2 where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) (Martin et al., (1995) Helv. Chim. Acta, 78, 486-504) i.e., an alkoxyalkoxy group. A further preferred modification comprises 2'-dimethylaminooxyethoxy, i.e., a O(CH2) 2ON(CH3)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other preferred modifications comprise 2'-methoxy (2'-OCH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N2, N-6 and O-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) *Proc. Natl. Acad. Sci. USA*, 86, 6553-6556), cholic acid (Manoharan et al., (1994) *Bioorg. Med. Chem. Let.*, 4, 1053-1060), a thioether, e.g., hexyl-S-tritylthiol (Manoharan et al., (1992) *Ann. N.Y. Acad. Sci.*, 660, 306-309; Manoharan et al., (1993) *Bioorg. Med. Chem. Let.*, 3, 2765-2770), a thiocholesterol (Oberhauser et al., (1992) *Nucl. Acids Res.*, 20, 533-538), an aliphatic chain, e.g., dodecandiol or undecyl residues (Kabanov et al., (1990) *FEBS Lett.*, 259, 327-330; Svinarchuk et al., (1993) *Biochimie* 75, 49-54), a phospholipid, e.g., di-hexadecyl-rac-glycerol or triethylammonium 1,2-di-O-hexadecyl-rac-glycero-3-H-phosphonate (Manoharan et al., (1995) *Tetrahedron Lett.*, 36, 3651-3654; Shea et al., (1990) *Nucl. Acids Res.*, 18, 3777-3783), a polyamine or a polyethylene glycol chain (Mancharan et al., (1995) *Nucleosides & Nucleotides*, 14, 969-973), or adamantane acetic acid (Manoharan et al., (1995) *Tetrahedron Lett.*, 36, 3651-3654), a palmityl moiety (Mishra et al., (1995) *Biochim. Biophys. Acta*, 1264, 229-237), or an octadecylamine or hexylaminocarbonyl-t oxycholesterol moiety (Crooke et al., (1996) *J. Pharmacol. Exp. Ther.*, 277, 923-937).

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and preferred target segments identified herein in drug discovery efforts to elucidate relationships that exist between Brain derived neurotrophic factor (BDNF) polynucleotides and a disease state, phenotype, or condition. These methods include detecting or modulating Brain derived neurotrophic factor (BDNF) polynucleotides comprising contacting a sample, tissue, cell, or organism with the compounds of the present invention, measuring the nucleic acid or protein level of Brain derived neurotrophic factor (BDNF) polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

BDNF protein and mRNA expression can be assayed using methods known to those of skill in the art and described elsewhere herein. For example, immunoassays such as the ELISA can be used to measure protein levels. BDNF ELISA kits are available commercially, e.g., from R&D Systems (Minneapolis, Minn.).

In embodiments, BDNF expression (e.g., mRNA or protein) in a sample (e.g., cells or tissues in vivo or in vitro) treated using an antisense oligonucleotide of the invention is evaluated by comparison with BDNF expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the BDNF protein or nucleic acid in a treated vs an untreated sample can be compared with the difference in expression of a different nucleic acid (including any standard deemed appropriate by the researcher, e.g., a housekeeping gene) in a treated sample vs an untreated sample.

Observed differences can be expressed as desired, e.g., in the form of a ratio or fraction, for use in a comparison with control. In embodiments, the level of BDNF mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of BDNF mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Brain derived neurotrophic factor (BDNF) genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.,* 480, 17-24; Celis, et al., (2000) *FEBS Lett.,* 480, 2-16), SAGE (serial analysis of gene expression) (Madden, et al., (2000) Drug. Discov. Today, 5, 415-425), READS (restriction enzyme amplification of digested cDNAs) (Prashar and Weissman, (1999) *Methods Enzymol.,* 303, 258-72), TOGA (total gene expression analysis) (Sutcliffe, et al., (2000) *Proc. Natl. Acad. Sci. U.S.A.,* 97, 1976-81), protein arrays and proteomics (Celis, et al., (2000) *FEBS Lett.,* 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., (2000) *Anal. Biochem.* 286, 91-98; Larson, et al., (2000) *Cytometry* 41, 203-208), subtractive cloning, differential display (DD) (Jurecic and Belmont, (2000) *Curr. Opin. Microbiol.* 3, 316-21), comparative genomic hybridization (Carulli, et al., (1998) *J. Cell Biochem. Suppl.,* 31, 286-96), FISH (fluorescent in situ hybridization) techniques (Going and Gusterson, (1999) *Eur. J. Cancer,* 35, 1895-904) and mass spectrometry methods (To, Comb. (2000) *Chem. High Throughput Screen,* 3, 235-41).

The compounds of the invention are useful for research and diagnostics, because these compounds hybridize to nucleic acids encoding Brain derived neurotrophic factor (BDNF). For example, oligonucleotides that hybridize with such efficiency and under such conditions as disclosed herein as to be effective Brain derived neurotrophic factor (BDNF) modulators are effective primers or probes under conditions favoring gene amplification or detection, respectively. These primers and probes are useful in methods requiring the specific detection of nucleic acid molecules encoding Brain derived neurotrophic factor (BDNF) and in the amplification of said nucleic acid molecules for detection or for use in further studies of Brain derived neurotrophic factor (BDNF). Hybridization of the antisense oligonucleotides, particularly the primers and probes, of the invention with a nucleic acid encoding Brain derived neurotrophic factor (BDNF) can be detected by means known in the art. Such means may include conjugation of an enzyme to the oligonucleotide, radiolabeling of the oligonucleotide, or any other suitable detection means. Kits using such detection means for detecting the level of Brain derived neurotrophic factor (BDNF) in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Brain derived neurotrophic factor (BDNF) polynucleotides is treated by administering antisense compounds in accordance with this invention. For example, in one non-limiting embodiment, the methods comprise the step of administering to the animal in need of treatment, a therapeutically effective amount of Brain derived neurotrophic factor (BDNF) modulator. The Brain derived neurotrophic factor (BDNF) modulators of the present invention effectively modulate the activity of the Brain derived neurotrophic factor (BDNF) or modulate the expression of the Brain derived neurotrophic factor (BDNF) protein. In one embodiment, the activity or expression of Brain derived neurotrophic factor (BDNF) in an animal is inhibited by about 10% as compared to a control. Preferably, the activity or expression of Brain derived neurotrophic factor (BDNF) in an animal is inhibited by about 30%. More preferably, the activity or expression of Brain derived neurotrophic factor (BDNF) in an animal is inhibited by 50% or more. Thus, the oligomeric compounds modulate expression of Brain derived neurotrophic factor (BDNF) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Brain derived neurotrophic factor (BDNF) and/or in an animal is increased by about 10% as compared to a control. Preferably, the activity or expression of Brain derived neurotrophic factor (BDNF) in an animal is increased by about 30%. More preferably, the activity or expression of Brain derived neurotrophic factor (BDNF) in an animal is increased by 50% or more. Thus, the oligomeric compounds modulate expression of Brain derived neurotrophic factor (BDNF) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Brain derived neurotrophic factor (BDNF) may be measured in serum, blood, adipose tissue, liver or any other body fluid, tissue or organ of the animal. Preferably, the cells contained within said fluids, tissues or organs being analyzed contain a nucleic acid molecule encoding Brain derived neurotrophic factor (BDNF) peptides and/or the Brain derived neurotrophic factor (BDNF) protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., dihexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 3 to 8) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., (1995) *J. Neurochem,* 64: 487; Lim, F., et al., in DNA Cloning: Mammalian Systems, D. Glover, Ed. (Oxford Univ. Press, Oxford England) (1995); Geller, A. I. et al., (1993) *Proc Natl. Acad. Sci.: U.S.A.:*90 7603; Geller, A. I., et al., (1990) *Proc Natl. Acad. Sci. USA:* 87:1149], Adenovirus Vectors (LeGal LaSalle et al., Science, 259:988 (1993); Davidson, et al., (1993) *Nat. Genet.* 3: 219; Yang, et al., (1995) *J. Virol.* 69: 2004) and Adeno-associated Virus Vectors (Kaplitt, M. G., et al., (1994) *Nat. Genet.* 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Brain derived neurotrophic factor (BDNF), and the second target may be a region from another nucleotide sequence. Alternatively, compositions of the invention may contain two or more antisense compounds targeted to different regions of the same Brain derived neurotrophic factor (BDNF) nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years. In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Design of Antisense Oligonucleotides Specific for a Nucleic Acid Molecule Antisense to a Brain Derived Neurotrophic Factor (BDNF) Polynucleotide and/or a Sense Strand of Brain Derived Neurotrophic Factor (BDNF) Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2

Modulation of BDNF Polynucleotides

Treatment of HepG2 Cells with Antisense Oligonucleotides:
HepG2 cells from ATCC (cat #HB-8065) were grown in growth media (MEM/EBSS (Hyclone cat #SH30024, or Mediatech cat #MT-10-0,0-CV)+10% FBS (Mediatech cat #MT35-0,1-CV)+penicillin/streptomycin (Mediatech cat #MT30-002-CI)) at 37° C. and 5% $CO_2$. One day before the experiment the cells were replated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with HepG2 cells. A Similar mixture including 2 µl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Detection Oligos for BDNF Antisense:

```
ABI assay ID Hs00417345_m1
                                  (SEQ ID No.: 9)
Context sequence GCACACCTGGAGATACTCTATTATA
```

Detection Oligos for BDNF:

```
ABI assay ID Hs00542425_s1
CCTGCAGAATGGCCTGGAATTACAA    (SEQ ID No.: 10)
```

Figure 1B:
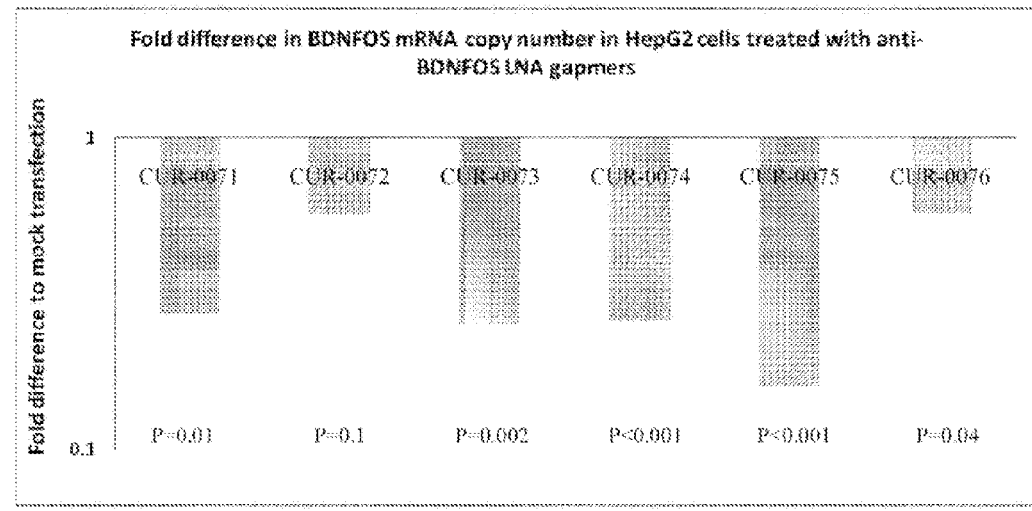
FIG. 1B is a graph of real time PCR results showing the fold change+standard deviation in BDNF mRNA after treatment of HepG2 cells with phosphorothioate oligonucleotides introduced using Lipofectamine 2000, as compared to control. Real time PCR results show that the levels of BDNF antisense were significantly decreased after treatment with all oligos except CUR-0072, which is possibly due to different oligos affecting different splice variants of BDNF and/or BDNF antisense NM_170735. Bars denoted as CUR-0071, CUR-0072, CUR-0073, CUR-0074, CUR-0075 and CUR-0076 correspond to samples treated with SEQ ID NOS: 6, 7, 8, 5, 4, 3, respectively.

Results:
Real time PCR results show that the levels of the BDNF mRNA in HepG2 cells are significantly increased 48 h after treatment with two of the LNA gapmers with fully phosphothioated backbone designed to BDNF antisense (CUR-71, P=0.04, CUR-73, P=0.07, CUR-76, P=0.03) (FIG. 1A). In the same samples the levels of BDNF antisense were significantly decreased after treatment with all oligos except CUR-72, which is possibly due to different oligos affecting different splice variants of BDNF and/or BDNF antisense (FIG. 1B).

Treatment of CHP212 Cells with Antisense Oligonucleotides:

CHP212 cells from ATCC (cat #CRL-2273) were grown in growth media (MEM/F12 (ATCC cat #30-2003 and Mediatech cat #10-080-CV)+10% FBS (Mediatech cat #MT35-0,1-CV)+penicillin/streptomycin (Mediatech cat #MT30-002-CI)) at 37° C. and 5% $CO_2$. One day before the experiment the cells were replated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with CHP212 cells. Similar mixture including 2 µl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00542425_s1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 1C:
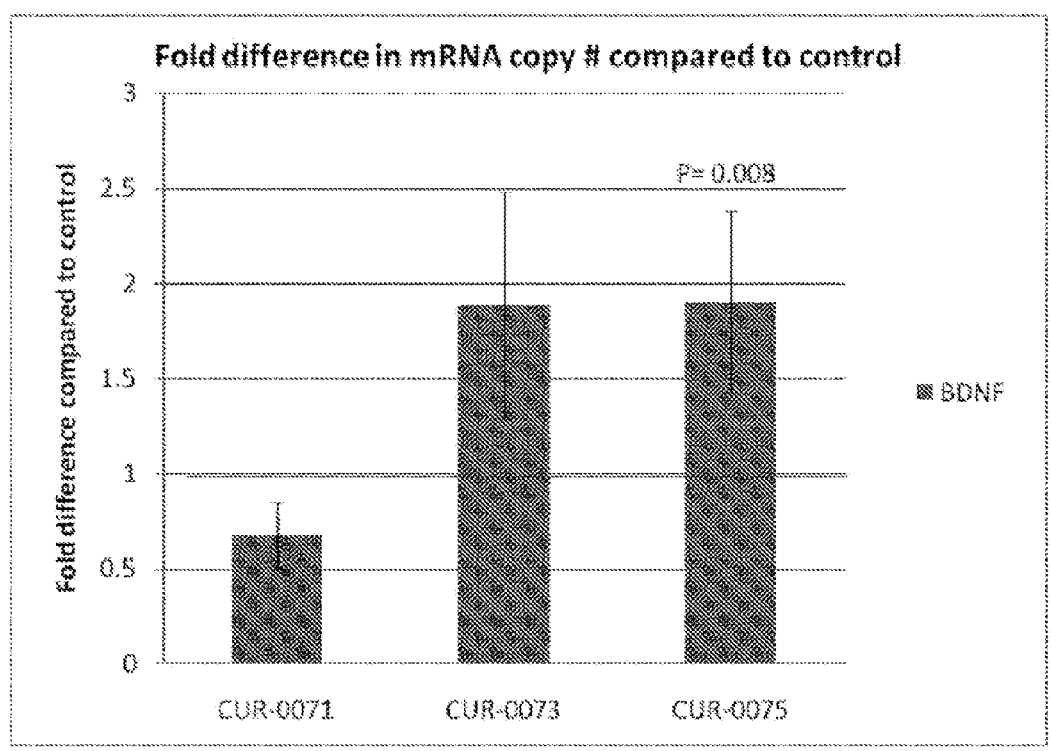
FIG. 1

Results:

Real time PCR results show that the levels of the BDNF mRNA in CHP212 cells are significantly increased 48 h after treatment with three of the oligos designed to BDNF antisense (FIG. 1C).

Example 3

Antisense Modulation of BDNF Polynucleotide and Protein Product and Effect on Memory and Learning in Amyloid-Transgenic Mice Antisense oligonucleotides specific for BDNF-AS (e.g., oligonucleotides identified by SEQ ID NOS 3-8) are administered to J20 mice, which express the human amyloid precursor protein (APP) transgene bearing both the Swedish and Indiana APP mutations. As described by, e.g., Nagahara, et al., 2009, "Neuroprotective effects of brain-derived neurotrophic factor in rodent and primate models of Alzheimer's disease," Nature Medicine 15(3): 331-337, incorporated herein by reference, these mice show cortical plaques and progressive cell loss in the entorhinal cortex beginning at age 2-3 months, and cognitive decline by 6-7 months. Pre-treatment blood samples are collected several days before dosing by collecting 4-7 drops from the tail vein. Each antisense oligonucleotide is dissolved in PBS and administered into a mouse by injection into the entorhinal cortex or the hippocampus at about 10 mg/kg. Control mice (age-matched WT littermates) are administered the same volume of PBS alone. One month later, spatial memory is tested in the Morris water maze in treated and control mice, and their performance compared. Restorative effects are also tested by measuring hippocampal-dependent and hippocampal-independent learning. After testing, the mice are sacrificed and brain tissues (entorhinal cortex and hippocampal dentate gyms) are collected for analysis of expression of BDNF protein and mRNA. Human BDNF protein concentration and secretion levels are determined using an enzyme linked immunosorbent assay (ELISA) kit (available commercially, e.g., Quantikine human BDNF, R&D Systems, Minneapolis, Minn.), according to the manufacturer's instructions. mRNA is assayed using RT-PCR, as described elsewhere herein.

Example 4

Antisense Modulation of BDNF Polynucleotide and Protein Product and Effect on Memory and Learning in SAM-P8 Mice The P8 strain of senescence accelerated mice (SAM), as described, e.g., in U.S. Pat. No. 6,310,048, "Antisense modulation of amyloid beta protein expression," incorporated herein by reference, show an age-related increase in impaired learning (acquisition) and memory (retention) as well as an age-related increase in the accumulation of amyloid precursor protein and AβP. SAM-P8 mice have a median life span of 17.2 months, as opposed to a normal life span of 24 months for standard R1 mice.

SAM-P8 mice are divided into seven groups of 10 mice each. At 11 months of age (4 weeks prior to training) one group is given 0.2 microliters of calf serum by intracerebral ventricular injection (ICV), while the other six groups are given one or two 0.2 microliter injections (each of 2 microliters and having 60 ng of oligonucleotide) ICV of antisense oligonucleotides of the present invention. Administration is performed by drilling a hole through the skull over the third ventricle (−0.5 relative to bregma; 0.5 mm right of central suture). The scalp is closed and the mice are returned to their cages. Two weeks after this first injection, one of the groups of treated mice and the group that had received serum are injected with the saline vehicle that is used as the carrier for the antisense oligonucleotides. At this same time (two weeks before training), each one of the oligonucleotides is administered in saline ICV to all of the mice in one group. Each administration contains 0.2 microliter (60 ng of oligonucleotide per injection).

Two weeks after the last injection, when the mice are 12 months of age, they are trained on footshock avoidance in a T-maze. The training and testing procedures are the same as described by Flood et al., Physiology & Behavior, 58:819-822 (1995); and Flood et al., Neurobiology of Aging, 14:159-166 (1993), and U.S. Pat. No. 6,310,048, all incorporated by reference herein. All mice are trained until they make their first avoidance response. Retention test scores when tested 1 hr after training and one week later are compared. One week after original training, retention for both 4 and 12 month-old mice is tested by continuing the training until each mouse makes 5 avoidances in 6 consecutive training trials. Results are expressed as means and with a standard error of the means. The trials to first avoidance, or to a criterion of 5 avoidances in 6 consecutive trials are analyzed in separate one way ANOVAs. Statistical differences between the means of the 12 month-old mice that received antisense oligonucleotides are compared to the means of the 12 month-old mice that received the saline solution vehicle using Dunnett's T-test.

Samples are recovered from the amygdala, hippocampal, and septum regions of the brains of each of four mice, two treated with the saline vehicle and the other two treated with the antisense oligonucleotides. The samples are tested for BDNF protein expression by ELISA or immuno-blotting against an antibody that specifically hybridizes to BDNF.

Example 5

Antisense Modulation of BDNF Polynucleotide and Protein Product and Effect on Disease Progression in Patients with Amyotrophic Lateral Sclerosis A pharmaceutical composition comprising an antisense oligonucleotide of the present invention (e.g., an oligonucleotide identified by any of SEQ ID NOS: 3-8) is administered to the cerebrospinal fluid of an individual suffering from familial ALS. A Medtronic SyncroMed II pump is used to deliver the composition to the cerebrospinal fluid. The pump is surgically implanted according to the manufacturer instructions. The pump reservoir is loaded with the pharmaceutical composition in phosphate-buffered saline. The pharmaceutical composition is administered at an amount that yields an infusion of 8 mg to 12 mg/day of the antisense oligonucleotide into the cerebrospinal fluid. Antisense oligonucleotide is infused, for at least 28 days. The drug is pumped at a programmed dose into a catheter that is surgically intrathecally implanted.

Disease progression is measured by methods routine in the art and described herein, for example, using indicators including ALSFSR-R, and measurements of $FEV_1$, FVC, and muscle strength. These methods are used by a physician to assess disease state at initiation of treatment, and to provide a baseline for disease state. Subsequent assessments are performed at intervals, as determined by the physician, during the delivery period. Expression of BDNF protein and mRNA in cerebrospinal fluid is assayed. Human BDNF protein concentration and secretion levels are determined using an enzyme linked immunosorbent assay (ELISA) kit (e.g., Quantikine human BDNF, R&D Systems, Minneapolis, Minn.), according to the manufacturer's instructions. mRNA is assayed using RT-PCR, as described elsewhere herein.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of upregulating a function of and/or the expression of a Brain derived neurotrophic factor (BDNF) polynucleotide having SEQ ID NO: 11 or expression product thereof in patient cells or tissues in vivo or in vitro comprising:
   contacting said cells or tissues with at least one single stranded antisense oligonucleotide of 10 to 30 nucleotides in length wherein said at least one oligonucleotide is specific for and specifically hybridizes to a natural antisense polynucleotide of BDNF having SEQ ID NO: 2 and has at least 80% sequence identity to a reverse complement of a polynucleotide comprising about 10 to about 30 consecutive nucleotides within nucleotides 1 to 3175 of SEQ ID NO: 2;
   thereby upregulating a function of and/or the expression of the Brain derived neurotrophic factor (BDNF) polynucleotide in patient cells or tissues in vivo or in vitro.

2. A method of upregulating a function of and/or the expression of a Brain derived neurotrophic factor (BDNF) polynucleotide having SEQ ID NO: 11 or expression product thereof in patient cells or tissues in vivo or in vitro comprising:
   contacting said cells or tissues with at least one single stranded antisense oligonucleotide of 10 to 30nucleotides in length wherein said at least one oligonucleotide specifically targets and specifically hybridizes to a natural antisense polynucleotide of a BDNF gene and has at least 80% sequence identity to a corresponding 10 to 30 nucleotide region within a reverse complement of said natural antisense polynucleotide of a Brain derived neurotrophic factor (BDNF) polynucleotide;
   thereby upregulating a function of and/or the expression of the Brain derived neurotrophic factor (BDNF) polynucleotide in patient cells or tissues in vivo or in vitro.

3. A method of upregulating a function of and/or the expression of a Brain derived neurotrophic factor (BDNF) polynucleotide having SEQ ID NO: 11 or expression product thereof in patient cells or tissues in vivo or in vitro comprising:
   contacting said cells or tissues with at least one single stranded antisense oligonucleotide of 12 to 30nucleotides in length that specifically targets and hybridizes to a 12 to 30 nucleotide region of a natural antisense polynucleotide of the Brain derived neurotrophic factor (BDNF) polynucleotide;
   thereby upregulating a function of and/or the expression of the Brain derived neurotrophic factor (BDNF) polynucleotide in patient cells or tissues in vivo or in vitro.

4. The method of claim 3, wherein a function of and/or the expression of the Brain derived neurotrophic factor (BDNF) is increased by 10% in vivo or in vitro with respect to a control.

5. The method of claim 3, wherein the at least one antisense oligonucleotide targets a natural antisense sequence of a Brain derived neurotrophic factor (BDNF) polynucleotide comprising SEQ ID NO: 2.

6. The method of claim 3, wherein the at least one antisense oligonucleotide targets a. natural antisense polynucleotide antisense to non-coding nucleic acid sequences of the Brain derived neurotrophic factor (BDNF) RNA polynucleotide transcribed from the BDNF gene.

7. The method of claim 3, wherein the at least one antisense oligonucleotide targets a natural antisense oligonucleotide having overlapping sequences with a Brain derived neurotrophic factor (BDNF) polynucleotide.

8. The method of claim 3, wherein the at least one antisense oligonucleotide comprises one or more modifications selected from, at least one modified sugar moiety, at least one modified internucleoside linkage, at least one modified nucleotide, and combinations thereof.

9. The method of claim 8, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

10. The method of claim 8, wherein the one or more modifications comprise at least one modified internucleoside linkage selected from: a phosphorothioate, alkylphosphonate, phosphorodithioate, alkylphosphonothioate, phosphoramidate, carbamate, carbonate, phosphate triester, acetamidate, carboxymethyl ester, and combinations thereof.

11. The method of claim 8, wherein the one or more modifications comprise at least one modified nucleotide selected from: a peptide nucleic acid (PNA), a locked nucleic acid (LNA), an arabino-nucleic acid (FANA), an analogue, a derivative, and combinations thereof.

12. The method of claim 1, wherein the at least one oligonucleotide comprises at least one of the oligonucleotide sequences set forth as SEQ ID NOS: 3 to 8.

13. A method of upregulating a function of and/or the expression of Brain derived neurotrophic factor (BDNF) having SEQ ID NO: 1 in mammalian cells or tissues in vivo or in vitro comprising:

contacting said cells or tissues with at least one single stranded antisense oligonucleotide of about 12to about 30 nucleotides in length specific for and specifically hybridizine to noncoding and/or coding sequences of a natural antisense strand of a Brain derived neurotrophic factor (BDNF) polynucleotide wherein said at least one antisense oligonucleotide has at least 90% sequence identity to at least one of the nucleic acid sequences set forth as SEQ ID Nos: 1 or an RNA polynucleotide encoded by the BDNF gene; and, upregulatinq the function and/or expression of the Brain derived neurotrophic factor BDNF) in mammalian cells or tissues in vivo or in vitro.

* * * * *